(12) United States Patent
Davis et al.

(10) Patent No.: US 9,267,943 B2
(45) Date of Patent: Feb. 23, 2016

(54) APPARATUS FOR MAGNETIC SEPARATION OF CELLS

(75) Inventors: Ronald W. Davis, Palo Alto, CA (US); Stefanie S. Jeffrey, Los Altos Hills, CA (US); Michael N. Mindrinos, Menlo Park, CA (US); R. Fabian Pease, Stanford, CA (US); Ashley Ann Powell, Mountain View, CA (US); AmirAli Hajhossein Talasaz, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1000 days.

(21) Appl. No.: 13/284,482

(22) Filed: Oct. 28, 2011

(65) Prior Publication Data

US 2012/0045828 A1 Feb. 23, 2012

Related U.S. Application Data

(62) Division of application No. 12/333,213, filed on Dec. 11, 2008, now Pat. No. 8,071,395.

(60) Provisional application No. 61/013,238, filed on Dec. 12, 2007.

(51) Int. Cl.
*G01N 33/543* (2006.01)
*B03C 1/01* (2006.01)
*B03C 1/28* (2006.01)

(52) U.S. Cl.
CPC ............ *G01N 33/54333* (2013.01); *B03C 1/01* (2013.01); *B03C 1/286* (2013.01); *B03C 2201/18* (2013.01); *B03C 2201/26* (2013.01)

(58) Field of Classification Search
CPC ...... B03C 1/01; B03C 1/286; B03C 2201/18; B03C 2201/26; G01N 33/54333
USPC ................................................. 436/518, 526
See application file for complete search history.

(56) References Cited

U.S. PATENT DOCUMENTS 2,517,325 A 8/1950 Lamb
3,970,518 A 7/1976 Giaever
(Continued)

FOREIGN PATENT DOCUMENTS

EP 0593480 B1 8/1991
EP 0593480 B1 4/1994
(Continued)

OTHER PUBLICATIONS

Allard, Jeffrey W., et al., "Tumor Cells Circulate in the Peripheral Blood of All Major Carcinomas but not in Healthy Subjects or Patients With Nonmalignant Diseases," Clinical Cancer Research, Oct. 15, 2004, vol. 10, 6897-6904.

(Continued)

*Primary Examiner* — Bao Thuy L Nguyen
*Assistant Examiner* — Pensee Do
(74) *Attorney, Agent, or Firm* — David J. Aston; Bozicevic, Field & Francis LLP

(57) ABSTRACT

Described here is an automated robotic device that isolates circulating tumor cells (CTCs) or other biological structures with extremely high purity. The device uses powerful magnetic rods covered in removable plastic sleeves. These rods sweep through blood samples, capturing, e.g., cancer cells labeled with antibodies linked to magnetically responsive particles such as superparamagnetic beads. Upon completion of the capturing protocol, the magnetic rods undergo several rounds of washing, thereby removing all contaminating blood cells. The captured target cells are released into a final capture solution by removing the magnetic rods from the sleeves. Additionally, cells captured by this device show no reduced viability when cultured after capture. Cells are captured in a state suitable for genetic analysis. Also disclosed are methods for single cell analysis. Being robotic allows the device to be operated with high throughput.

21 Claims, 23 Drawing Sheets

(56) References Cited

U.S. PATENT DOCUMENTS

| | | | |
|---|---|---|---|
| 5,186,827 | A | 2/1993 | Liberti et al. |
| 5,200,084 | A | 4/1993 | Liberti et al. |
| 5,215,926 | A | 6/1993 | Etchells, III et al. |
| 5,536,475 | A | 7/1996 | Moubayed et al. |
| 5,567,326 | A | 10/1996 | Ekenberg et al. |
| 5,597,531 | A | 1/1997 | Liberti et al. |
| 5,622,831 | A | 4/1997 | Liberti et al. |
| 5,646,001 | A | 7/1997 | Terstappen et al. |
| 5,837,144 | A | 11/1998 | Bienhaus et al. |
| 5,876,593 | A | 3/1999 | Liberti et al. |
| 5,942,124 | A | 8/1999 | Tuunanen |
| 5,972,721 | A | 10/1999 | Bruno et al. |
| 6,040,192 | A | 3/2000 | Tuunanen |
| 6,065,605 | A | 5/2000 | Korpela et al. |
| 6,184,043 | B1 | 2/2001 | Fodstad et al. |
| 6,190,870 | B1 | 2/2001 | Schmitz et al. |
| 6,207,463 | B1 | 3/2001 | Tuunanen |
| 6,365,362 | B1 | 4/2002 | Terstappen et al. |
| 6,403,038 | B1 | 6/2002 | Heermann |
| 6,409,925 | B1 | 6/2002 | Gombinsky et al. |
| 6,448,092 | B1 | 9/2002 | Tuunanen |
| 6,468,432 | B1 | 10/2002 | Miltenyi et al. |
| 6,468,810 | B1 | 10/2002 | Korpela |
| 6,500,343 | B2 | 12/2002 | Siddiqi |
| 6,551,843 | B1 | 4/2003 | Rao et al. |
| 6,596,162 | B2 | 7/2003 | Tuunanen |
| 6,649,419 | B1 | 11/2003 | Anderson |
| 6,730,217 | B2 | 5/2004 | Schaaf et al. |
| D502,450 | S | 3/2005 | Rundt et al. |
| 6,890,426 | B2 | 5/2005 | Terstappen et al. |
| 7,056,657 | B2 | 6/2006 | Terstappen et al. |
| 7,125,964 | B2 | 10/2006 | Luxembourg et al. |
| 7,138,269 | B2 | 11/2006 | Blankenstein |
| 7,282,350 | B2 | 10/2007 | Rao et al. |
| 7,332,288 | B2 | 2/2008 | Terstappen et al. |
| 2002/0172987 | A1* | 11/2002 | Terstappen et al. .......... 435/7.23 |
| 2002/0183692 | A1 | 12/2002 | Callister |
| 2003/0044832 | A1 | 3/2003 | Blankenstein |
| 2004/0072269 | A1 | 4/2004 | Rao et al. |
| 2006/0134599 | A1 | 6/2006 | Toner et al. |
| 2006/0194192 | A1 | 8/2006 | Rao et al. |
| 2006/0207944 | A1* | 9/2006 | Siddiqi .................... 210/695 |
| 2006/0257847 | A1 | 11/2006 | Scholtens et al. |
| 2006/0266130 | A1* | 11/2006 | Zobel et al. ............... 73/864.02 |
| 2007/0018764 | A1 | 1/2007 | Martinez Garcia et al. |
| 2007/0026417 | A1 | 2/2007 | Fuchs et al. |
| 2007/0037173 | A1 | 2/2007 | Allard et al. |
| 2007/0154960 | A1 | 7/2007 | Connelly et al. |
| 2007/0251885 | A1* | 11/2007 | Korpela et al. ............. 210/690 |
| 2008/0305473 | A1 | 12/2008 | Chowdary et al. |

FOREIGN PATENT DOCUMENTS

| | | |
|---|---|---|
| EP | 1058851 B1 | 2/1999 |
| EP | 1058851 B1 | 12/2000 |
| EP | 1425294 B1 | 8/2002 |
| EP | 1425294 B1 | 6/2004 |
| WO | 8705536 A1 | 9/1987 |
| WO | 96/09550 A1 | 3/1996 |
| WO | 9940444 A1 | 8/1999 |
| WO | 0206790 A1 | 1/2002 |
| WO | 03069421 A2 | 8/2003 |
| WO | 2004076643 A2 | 9/2004 |
| WO | 2005/028663 A2 | 3/2005 |
| WO | 2006/041453 A1 | 4/2006 |
| WO | 2006042005 A2 | 4/2006 |
| WO | 2006054991 A1 | 5/2006 |
| WO | 2006102233 A2 | 9/2006 |
| WO | 2006104474 A2 | 10/2006 |
| WO | 2006105319 A2 | 10/2006 |
| WO | 2007053142 A1 | 5/2007 |
| WO | 2007053245 A2 | 5/2007 |
| WO | 2007063174 A1 | 6/2007 |
| WO | 2007086047 A2 | 8/2007 |
| WO | 2007106523 A2 | 9/2007 |
| WO | 2008048027 A1 | 4/2008 |

OTHER PUBLICATIONS

Patrawalla, Lubna, et al., "Side Population Is Enriched in Tumorigenic, Stem-Like Cancer Cells, whereas ABCG2+ and ABCG2− Cancer Cells Are Similarly Tumorigenic," Cancer Research, Jul. 15, 2005, vol. 65, No. 14, 6207-621.

Tong, Xiadong, et al., "Application of Immunomagnetic Cell Enrichment in Combination with RT-PCR for the Detection of Rare Circulating Head and Neck Tumor Cells in Human Peripheral Blood," Clinical Cytometry, 2007, 72B:310-323.

Powell, Ashley A., et al., "MagSweeper: An Automated System for High Specificity Capture of Live Circulating Tumor Cells," Poster, Presented at San Antonio Breast Cancer Symposium, Dec. 12, 2007.

Talasaz, AH, et al., "Development of a New Device for High Throughput Isolation of Live Circulating Tumor Cells," Poster, Presented at San Antonio Breast Cancer Symposium, Dec. 16, 2006.

International Search Report and Written Opinion, Application No. PCT/US08/86486, Feb. 4, 2009, 9pp.

Liberti, et al., "Optimization of ferrofluids and protocols for the enrichment of breast tumor cells in blood", Journal of Magnetism and Magnetic Materials, 225 (2001) 301-307.

Riethdorf, et al., "Detection of circulating tumor cells in peripheral blood of patients with metastatic breast cancer: a validation study of the cellsearch system", Clin Cancer Res 2007;13(3) Feb. 1, 2007, pp. 920-928.

European Search Report, Application No. 08859615.0, Apr. 7, 2011.

* cited by examiner

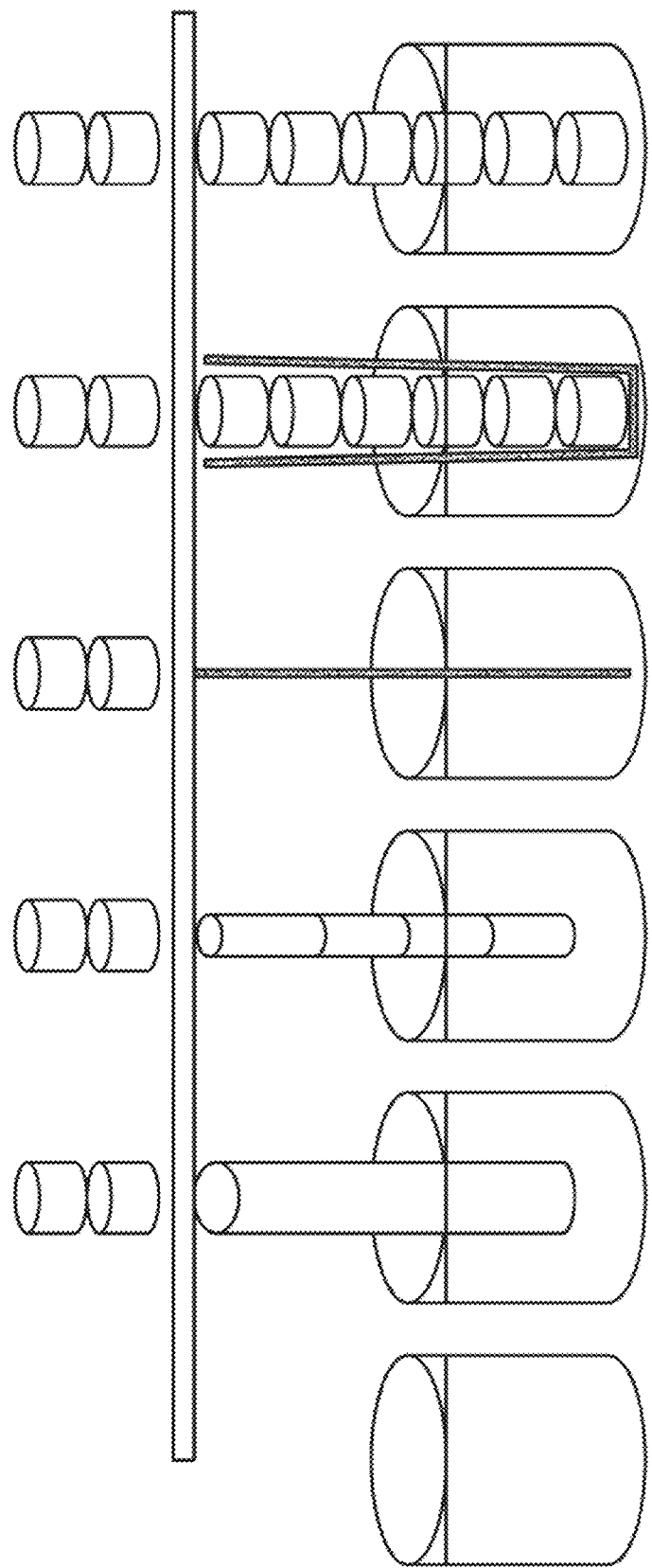

Capture

Wash

Release

APPARATUS FOR MAGNETIC SEPARATION OF CELLS

CROSS-REFERENCE TO RELATED APPLICATIONS

This application claims priority from U.S. patent application Ser. No. 12/333,213, filed on Dec. 11, 2008, and from U.S. Provisional Patent Application No. 61/013,238, filed on Dec. 12, 2007, both of which are hereby incorporated by reference in their entirety.

FEDERALLY-SPONSORED RESEARCH OR DEVELOPMENT

This invention was made with Government support under contract HG000205 awarded by the National Institutes of Health. The Government has certain rights in this invention.

REFERENCE TO SEQUENCE LISTING, COMPUTER PROGRAM, OR COMPACT DISK

None

BACKGROUND OF THE INVENTION

1. Field of the Invention

The present invention relates to the field of cell isolation, including the isolation of cells from peripheral circulation, labeling cells of interest magnetically, and using an automatable apparatus to immobilize and isolate viable labeled cells for further testing and culture.

2. Related Art

Background

Utilizing current technologies, it is possible to count the number of circulating tumor cells present in blood from breast cancer patients and predict disease outcome [1,2]. However, due to the lack of additional information about the population of circulating tumor cells, current methods do not offer insights into directing treatment or developing novel therapies. Current targeted treatments based on breast cancer subtypes, e.g., Her2/neu or estrogen receptor (ER) status, only focus on the subtype of the primary tumor [3,4,5]. Recent studies have shown that a portion of breast cancer metastases have different Her2 and ER status compared to the original primary tumors [6,7,8,9]. By analyzing the circulating tumor cells (CTCs) for their genetic characteristics, one can target treatment not only to the primary tumor, but also to cells that may contribute to and serve as surrogate markers of metastases, thus improving survival in women with metastatic disease.

CTCs can be collected through a relatively non-invasive blood draw. However, isolating, purifying, and characterizing these cells has proven challenging. Several current technologies allow for isolation and counting of circulating tumor cells from patient blood samples. Additionally, the expression of two or three biomarkers can also be assessed. However, while the CTCs are enriched during these protocols, they are often heavily contaminated with blood cells, may not be viable, or the RNA may be severely compromised, making it difficult to reliably measure gene expression or simultaneously measure the expression of large numbers of genes. Described below is a robotic device which allows one to obtain completely purified, living CTCs. In combination with multiplex qRT-PCR, genes from single CTCs isolated from the blood of patients with metastatic breast cancer were analyzed for expression levels. Thus, current techniques partially purify CTCs from blood, but there is still residual contamination with other blood cells. Some techniques also fix and permeabilize the CTCs, making them unsuitable for downstream microarray analysis or in vitro and in vivo biological studies.

CTC biology is still poorly defined because most studies assess only CTC burden. The characterization of CTCs is a nascent field; isolation of CTCs specifically for multigene molecular analyses, in contradistinction to counting, is challenging for multiple biological and technical reasons. The cells are fragile, likely a result of mechanical stresses on CTCs in the blood stream and chemical effects of cytotoxic chemotherapy. Moreover, CTCs are extremely rare. For example, 81% of metastatic breast cancer patients will have less than ten CTCs in a 7.5 cc tube of blood containing about $10^{10}$ blood cells. Technical factors that impede CTC gene expression analysis in currently available platforms include cell fixation and permeabilization, immobilization, and, most importantly, blood cell contamination. CTC fixation and permeabilization performed prior to fluorescent labeling of CTCs can structurally modify RNA and impact cell viability. CTC immobilization on substrates such as glass slides, filters, or microposts limit single cell manipulation. Finally, even after enrichment, CTCs may be contaminated by thousands of leukocytes (white blood cells, WBCs) that confound expression analysis, requiring bioinformatic techniques to subtract non-CTC gene expression. Thus, direct simultaneous analysis of many gene targets in single human CTCs has yet to be performed.

Certain commercial technologies use immunomagnetic enrichment. Commercial products include the CellTracks® AutoPrep® System and CellSearch™ Circulating Tumor Cell Kit (Immunicon Corporation, Huntingdon Valley, Pa.), MACS® separation technology (Miltenyi Corporation, Bergisch Gladbach, Germany), and the RoboSep® automated cell separator (StemCell Technologies, Vancouver, Canada). With these techniques, the epithelial cells in the blood are labeled with magnetic particles attached to an antibody targeted to an epithelial cell surface marker, usually EpCAM. The blood is processed and external magnets hold the epithelial cells at the side of the tube, while the other blood cells are diluted and pipetted out or eluted through a column. The remaining epithelial cells are then available for immunocytochemical analysis, again amidst 1000-10,000 WBCs. Because of heavy mononuclear cell contamination (whose nucleic acids or proteins would overwhelm any subsequent molecular analyses of the CTCs), most analyses stain and count cells, or limit characterization to one to two immunostains.

Specific Patents and Publications

U.S. Pat. No. 3,970,518 to Giaever, issued Jul. 20, 1976, entitled "Magnetic separation of biological particles," discloses a method and apparatus in which the particular cell population that is to be separated from a mixed population is contacted with small magnetic particles or spheres which are first provided with a monomolecular coating of antibody to this select population. As the metallic particles enter the field created by a coil at the bottom of the vessel, they are captured and immobilized while liquid is unaffected and leaves vessel.

U.S. Pat. No. 7,125,964 to Luxembourg, et al., issued Oct. 24, 2006, entitled "Purification of antigen-specific T cells," discloses a method to capture, purify and expand antigen-specific T lymphocytes, using magnetic beads coated with recombinant MHC class I molecules. The inventors used attachment of biotinylated MHC Class I molecules on Aaidin-coated magnetic beads.

U.S. Pat. No. 5,200,084 to Liberti, et al. Apr. 6, 1993, entitled "Apparatus and methods for magnetic separation," discloses a magnetic separation apparatus and methods for separating colloidal magnetic particles from a non-magnetic test medium in which the magnetic particles are suspended. The separator comprises a container holding the non-magnetic test medium, one or more magnetic wires disposed substantially within the test medium in the container and an external magnet (illustrated at 31 of FIG. 1 of the patent) for producing a magnetic field gradient within the test medium. According to the method of the invention, the container holding the test medium is positioned in the separator, producing a magnetic field gradient operative to cause the magnetic particles to be attracted to the areas surrounding the magnetized wires and to adhere to the wires.

U.S. Pat. No. 5,837,144 to Bienhaus, et al., issued Nov. 17, 1998, entitled "Method of magnetically separating liquid components," discloses Method of separating a component of a liquid from other components by immobilizing the component to suspended magnetic particles in a vessel, immersing a magnetic device into the vessel while the device is separated from the liquid by means of a protective sleeve made of a non-magnetic material. The protective sleeve is selected such that its outer surface is always spaced apart from the inner surface of the vessel by approximately the same distance.

U.S. Pat. No. 6,468,810 to Korpela, issued Oct. 22, 2002, entitled "Magnetic particle transfer device and method," discloses a pipette like device for transfer suitable for capturing and releasing microparticles binding an immobilized substance, which includes a magnet as well as either an extendable membrane, shapable membrane or magnet's coating such that the membrane or coating pressing tightly against the magnet's surface separates the magnet from the microparticles but does not substantially weaken the magnetic field directed at the microparticles (See FIGS. 1D and 1E of the patent).

US 20070251885 by Korpela et al., published Nov. 1, 2007, entitled "Method and a Device for Treating Microparticles," disclose a method for handling microparticles in such a manner, that at least two treatment steps are performed for microparticles in the same vessel without moving the particles to another vessel. This can be brought about by moving the magnet inside the ferromagnetic tube in such a manner, that it can be completely inside the tube, whereupon the efficiency of the magnet is insignificant or nonexistent, or it can be partially or completely outside the tube, whereupon the efficiency and the collecting area of the magnet are in relation to the protruding part of the magnet.

BRIEF SUMMARY OF THE INVENTION

The following brief summary is not intended to include all features and aspects of the present invention, nor does it imply that the invention must include all features and aspects discussed in this summary.

In certain aspects, the present invention comprises a method for capturing and isolation of cells comprising: (a) mixing a sample comprising rare target cells and contaminant cells with magnetically responsive particles having an affinity to the rare target cells to produce a solution having magnetically responsive particles bound to rare target cells; (b) contacting a magnetic member having a non-adherent sleeve with the solution; (c) producing a continuous relative motion between the magnetic member and the solution while the magnetic member produces a magnetic field across the non-adherent sleeve, such that the magnetically responsive particles bound to rare target cells are selectively captured onto the non-adherent sleeve; (d) contacting the magnetic member having the captured rare target cells with a recovery solution; (e) substantially removing the magnetic field produced by the member across the non-adherent sleeve such that the magnetically responsive particles bound to rare target cells are released into the recovery fluid.

In certain aspects, the present invention comprises a device for capture and isolation of target cells from a mixed cell population wherein the target cells are labeled with magnetically responsive material to form labeled target cells, where the device comprises (a) magnetic member having a tip and another end connected to an actuator; (b) a sleeve between the magnetic member and the mixed cell population to prevent direct contact of cells with the magnetic member, said sleeve being nonmagnetic and nonadherent to cells in the mixed cell population; (c) said sleeve being separable from the magnetic member by the actuator, which causes movement between the magnetic member and the sleeve, whereby the magnetic member is moved more or less into the sleeve; and (d) said actuator being constructed and arranged for causing in the device (i) relative stirring movement between the magnetic member and the mixed cell population to contact the magnetic member with a majority of cells in the mixed cell population, and (ii) causing movement of the magnetic member into and out of the container to retrieve target cells from the mixed cell population. The term "sleeve" as used here, refers to a covering that can be fitted to and closed to completely cover a region of the magnetic member that is in contact with the cells. The relative stifling movement, movement into and out of the sleeve and into and out of container(s) is preferably accomplished by mounting the actuator on a robotic mechanism for x-y-z movement, such robotic actuators being known in the art for other purposes.

The magnetic member in (a) may be a rod having a diameter of at least 4 mm to produce a high magnetic field strength and having a tapered tip for producing a high magnetic gradient. The magnetic gradient at the tip may be used to concentrate the magnetic field in a smaller area near the tip, which is on the container in use and contacting the target cells. It has been found that the magnetic member may advantageously have a tapered tip. This may be rounded or of a compound shape. In further aspects, the magnetic member possesses a field strength at the tip of at least 0.2 to 1 Tesla, or about 0.5 Tesla. Measured another way, the magnetic member may have a pull strength of at least 70 pounds. In certain aspects, the device comprises the use of a rare earth magnet. The magnetic member may thus comprise neodymium, iron and boron (NIB magnet). The sleeve material is nonadherent, and may consist essentially of a material selected from the group consisting of vinyl polymer, paramagnetic metal, ceramic material, and polyHEMA. The vinyl polymer may be medical grade PVC. To accomplish efficient sweeping, the actuator may cause orbital movement to contact the magnetic member with a majority of cells. Orbital movement may be, for example, outwardly expanding concentric circles, expanding outward until near the wall(s) of the container. The device may comprise (and in use may use) one or more containers for holding the sample, for holding a wash solution and for holding target cells after isolation from the mixed cell population. In certain embodiments, there are separate containers for holding sample, wash solution and target cells. Like the sleeve, the container may be designed to comprise a material which is non-adherent to target cells. Rather than a container that closely approaches the magnetic member, the container may define an open pool for holding the sample. The pool will have a surface area considerably larger than the cross sectional area of the magnetic member and will have no external means for movement of the sample during sweeping. This facilitates the stifling, or sweeping. The actuator may comprise a component which causes the magnetic member to sweep through the pool in concentric circles. There may be, in certain embodiments, only one magnetic member, or an array, with one magnetic member in each container. The device may comprise multiple magnetic members controlled by a single actuator.

The device may further comprise apparatus for further processing purified target cells left in the wash solution. The device may comprise a probe for extracting a single target cell from a collection of target cells isolated after removal of contaminant cells. The further processing apparatus may comprise a computer programmed with image recognition software and controlling the probe. The probe may be directed towards a concentration of target cells obtained when a magnet is used to concentrate the cells in a recovery or wash container.

In certain aspects, the present invention comprises a method. It comprises a method for capture and isolation of intact, rare target cells in a sample having a mixed cell population of target cells and contaminant cells, wherein the target cells are labeled with magnetically responsive material to form labeled target cells, comprising: (a) labeling the sample with a label specific for target cells, said label being magnetically responsive, to form a labeled sample; (b) contacting the labeled sample with a member extending into the sample and comprising a strong magnet covered by a nonmagnetic, non-adherent sleeve; (c) sweeping the member through the sample to cause cells to attach to the sleeve; (d) washing the sleeve with cells attached to remove unlabeled cells; (e) separating the magnet from the sleeve, whereby labeled cells are removed from the sleeve; and (f) collecting labeled cells to form a composition comprising beads and labeled cells. The term "washing" may include either or both of simply immersing the bound cells on the rod into a cell free solution, or a step of moving the cells attached to the sleeve into a cell free solution, releasing the bound cells and recapturing them. The release and recapture step has been used in the presently exemplified methods.

The present methods may further include further processing of an isolated cell (e.g., CTC). They may include the step of isolating a single labeled cell from the beads (or a single bead). The methods may include the use of certain cell surface markers, such as an HLA marker (e.g., HLA-A2), an epithelial cell surface marker, such as EpCAM, or a stem cell marker such as CD44 or CD96.

As described below, the method does not require pre-processing and may be carried out. It may, in certain method embodiments, the sample is human peripheral blood which has only been minimally treated, such as by dilution and anticoagulation. As discussed below, the target cells may be rare cells such as CTCs. The method of the present invention may comprise in certain aspects, multiple washing steps as recited in step (d). The method of the present invention may comprise in certain aspects, the step of extracting intact genetic material from isolated target cells. This may further comprise the step of testing for expression of certain genes in extracted genetic material. The analysis of the genetic material may be useful in the study of individual CTCs from a given patient. The genes to be analyzed for expression level may include GAPDH, beta actin, big ribosome protein (RPLPO) (the foregoing being housekeeping genes), CRYAB, EGFR, FOXA1, CD44, ESR1 (ER) PGR (PR), and mutated forms of Myc, Ras, BRCA1, BRCA2, APC, and p53. The method of the present invention may comprise in certain aspects, testing for the expression level of the vimentin gene, where increased expression of vimentin indicates a putative mesenchymal CTC. The present device and methods enable the preparation of a relatively large number of purified CTCs. In certain aspects, the present invention may comprise an isolated population of viable CTCs having at least 10 cells of at least 90% purity of CTCs. For example, in a population of 100 cells, about at least 90 of them will be CTCs. As noted, the CTCs of the present isolation method are viable and do not have altered gene expression patterns. The presently exemplified compositions are CTCs which are breast cancer cells. It has also been found that the presently prepared compositions comprise a putative MSC (mesenchymal-like cancer stem cell).

One aspect of the invention comprises a method for capturing and isolating cells comprising: (a) mixing a sample comprising rare target cells and contaminant cells with magnetically responsive particles having an affinity to the rare target cells to produce a sample solution having magnetically responsive particles bound to rare target cells; (b) contacting a magnetic member having a non-adherent sleeve with the sample solution; (c) producing a continuous relative motion between the magnetic member and the sample solution while the magnetic member produces a magnetic field across the non-adherent sleeve, such that the magnetically responsive particles bound to rare target cells are selectively captured onto the non-adherent sleeve; (d) contacting the magnetic member having the captured rare target cells with a recovery solution; (e) substantially removing the magnetic field produced by the member across the non-adherent sleeve whereby the magnetically responsive particles bound to rare target cells are released into the recovery fluid.

In some embodiments, the non-adherent sleeve comprises a sleeve over the magnetic member, and step (e) of substantially removing magnetic field across the non-adherent sleeve comprises removing the magnetic member from at least a portion of the sleeve.

In some embodiments, the magnetic member comprises an electromagnet, and step (e) of substantially removing the magnetic field across the non-adherent sleeve comprises demagnetizing the electromagnet.

In some, alternative, embodiments, the magnetic member is held stationary in a fluid flow channel and the continuous relative motion between the magnetic member and the sample solution is produced by flowing the sample solution past the magnetic member.

In certain aspects of the invention, the continuous relative motion between the magnetic member and the sample solution produces a velocity in the non-turbulent flow regime. In some embodiments, the continuous relative motion between the magnetic member and the sample solution has a Reynolds number of 0.1 to 100. In some embodiments, the continuous relative motion between the magnetic member and the sample solution has velocity of 0.1 mm/sec to 1 mm/sec. In some embodiments, the magnetic member has a surface field strength of 0.2 Tesla to 1 Tesla. In some embodiments, the magnetic member has a surface field strength of 0.2 Tesla to 1 Tesla and the continuous relative motion between the magnetic member and the sample solution has velocity of 0.1 mm/sec to 1 mm/sec.

In some embodiments, the continuous relative motion is applied such that a majority of the sample solution has access to the magnetic member.

In some embodiments, the non-adherent sleeve comprises a polymer selected from the group consisting of vinyl, chlorofluorocarbon polymers and silicone. In some embodiments, the non-adherent sleeve comprises polyvinyl chloride (PVC).

In some embodiments, the method further comprises contacting the magnetic member having the captured rare target cells with a wash fluid after step (c).

One aspect of the invention comprises a method for capturing and isolation of cells comprising: (a) contacting a magnetic member having a non-adherent sleeve with a sample solution comprising rare target cells and contaminant cells wherein the rare cells constitute less that 0.1% of the cells in the sample and wherein some or all of the rare target cells are bound to magnetically responsive particles; (b) moving the magnetic member relative to the sample solution to capture rare target cells bound to magnetically responsive particles; and (c) releasing the rare target cells from the non-adherent sleeve into a recovery solution, whereby the capture rate is greater 35%, and the purity is greater than 99%.

In some embodiments, the sample solution is blood and the rare cells are present in the sample solution at less than 1 in 50 million, and the capture rate is greater than 75% and the purity is greater than 90%. In some embodiments, the sample solution is blood and the rare cells are present in the sample solution at less than 1 in 500 million, and the capture rate is greater than 35% and the purity is greater than 25%. In some embodiments, greater than 80% of the recovered rare target cells are intact. In some embodiments, greater than 80% of the recovered rare target cells are viable.

One aspect of the invention comprises a device for capturing and isolating cells comprising: (a) a sample vessel for holding a sample solution comprising rare target cells and contaminant cells wherein some or all of the rare target cells are bound to magnetically responsive particles; (b) a magnetic member having a non-adherent sleeve; (c) a recovery vessel for holding a recovery solution; (d) an actuator for causing continuous relative movement of the magnetic member (i) between containers, (ii) into and out of the vessels, and (iii) at least two directions within the sample vessel to provide continuous relative motion between the magnetic member and the sample solution to provide selective capture of magnetically responsive particles having bound rare cells; and (e) a mechanism for producing a magnetic field across the non-adherent sleeve while the magnetic member is in the sample solution, and for substantially removing the magnetic field across the non-adherent sleeve while the non-adherent sleeve is in the recovery solution. The sample vessel may be configured to hold the sample as a pool, as described above.

In some embodiments, the non-adherent sleeve comprises a sleeve over the magnetic member, and the mechanism for substantially removing the magnetic field across the non-adherent sleeve comprises moving the magnetic member out of at least a portion of the sleeve.

In some embodiments, the magnetic member comprises an electromagnet, and the mechanism for substantially removing the magnetic field across the non-adherent sleeve comprises demagnetizing the magnetic member.

One aspect of the invention comprises a device for capture and isolation of target cells from a mixed cell population wherein the target cells are labeled with magnetically responsive material to form labeled target cells, comprising: (a) a magnetic member having a tip and another end connected to an actuator; (b) a sleeve between the magnetic member and the mixed cell population to prevent direct contact of cells with the magnetic member, said sleeve being nonmagnetic and non-adherent to cells in the mixed cell population; (c) said sleeve being separable from the magnetic member by the actuator, which causes movement between the magnetic member and the sleeve, whereby the magnetic member is moved more or less into the sleeve; and (d) said actuator being constructed and arranged for causing in the device (i) relative stirring movement between the magnetic member and the mixed cell population to contact the magnetic member with a majority of cells in the mixed cell population, and (ii) causing movement of the magnetic member into and out of the container to retrieve target cells from the mixed cell population.

In some embodiments, the magnetic member is a rod having a diameter of 1 mm to 10 mm to produce a high magnetic field strength and having a tapered tip for producing a high magnetic gradient. In some embodiments, the magnetic member has a tapered tip. In some embodiments, the magnetic member possesses a field strength at the tip of at least 0.5 Tesla. In some embodiments, the magnetic member is a rare earth magnet. In some embodiments, the magnetic member has a pull strength of at least 70 pounds. In some embodiments, the magnetic member has a surface field strength of 0.2 to 1 Tesla. In some embodiments, the magnetic member comprises neodymium, iron and boron.

In some embodiments, the sleeve consists essentially of a material selected from the group consisting of vinyl polymer, paramagnetic metal, ceramic material, and polyHEMA.

In some embodiments, the magnetic member consists essentially of neodymium, iron and boron alloy.

In some embodiments, the actuator causes orbital movement to contact the magnetic member with a majority of cells.

In some embodiments, the device further comprises one or more containers for holding the sample, for holding a wash solution and for holding target cells after isolation from the mixed cell population. In some embodiments, there are separate containers for holding sample, wash solution and target cells. In some embodiments, the container comprises a material which is non-adherent to target cells.

One aspect of the invention comprises a device for capture and isolation of target cells in a sample having a mixed cell population of target cells and contaminant cells, wherein the target cells are labeled with magnetically responsive material to form labeled target cells, comprising: (a) a container for holding the sample; (b) a magnetic member having a tip; (c) a sleeve between the magnetic member and the mixed cell population to prevent direct contact of cells with the magnetic member, said sleeve being nonmagnetic and non-adherent to cells in the mixed cell population; (d) said sleeve being separable from the magnetic member by an that actuator causes movement between the magnetic member and the sleeve whereby the magnetic member is moved more or less into the sleeve; and (e) said actuator being constructed and arranged for causing (i) relative stifling movement in the container between the magnetic member and the mixed cell population to contact the magnetic member with a majority of cells in the mixed cell population, and (ii) causing movement of the magnetic member into and out of the container to retrieve target cells from the mixed cell population.

In some embodiments, the device further comprises a container which comprises a portion having a magnet opposite the magnetic member, for attracting isolated labeled target cells from the magnetic member in forming an isolated population. In some embodiments, the container defines an open pool for holding the sample. In some embodiments, the actuator comprises a component which causes the magnetic member to sweep through the pool in concentric circles. In some embodiments, the device comprises only one magnetic member in one container. In some embodiments, the device comprises multiple magnetic members controlled by a single actuator.

In some embodiments, the device further comprises a probe for extracting a single target cell from a collection of target cells isolated after removal of contaminant cells. In some embodiments, the device comprises a computer programmed with image recognition software and controlling the probe. In some embodiments, device further comprises a magnet for removing target cells from the sleeve.

One aspect of the invention comprises a method for capture and isolation of intact, rare target cells in a sample having a mixed cell population of target cells and contaminant cells, wherein the target cells are labeled with magnetically responsive material to form labeled target cells, comprising: (a) labeling the sample with a label specific for target cells, said label being magnetically responsive, to form a labeled sample; (b) contacting the labeled sample with a member extending into the sample and comprising a strong magnet covered by a nonmagnetic, non-adherent sleeve; (c) sweeping the member through the sample to cause cells to attach to the sleeve; (d) washing the sleeve with cells attached to remove unlabeled cells; (e) separating the magnet from the sleeve, whereby labeled cells are removed from the sleeve; and (f) collecting labeled cells to form a composition comprising beads and labeled cells.

In some embodiments, the method further comprises the step of isolating a single labeled cell from the beads. In some embodiments, the label is an antibody against an cell surface marker selected from the group consisting of HLA, EpCAM, CD44 and CD46. In some embodiments, the sample is human peripheral blood. In some embodiments, the target cells are CTCs.

In some embodiments, a strong magnet is a rare earth magnet having an axial dipole whereby magnetic particles are concentrated at one elongated end of the magnet. In some embodiments, the non-adherent sleeve is a polymer. In some embodiments, the polymer is a polymer selected from the group consisting of vinyl, chlorofluorocarbon polymers or silicone.

In some embodiments, the method further comprises the step of applying a magnetic field opposite the sleeve after the magnet has been removed to assist in removing labeled cells from the sleeve.

In some embodiments, the method further comprises multiple washing steps as recited in step (d) above.

In some embodiments, the method further comprises the step of extracting intact genetic material from isolated target cells. In some embodiments, method further comprises the step of testing for expression of certain genes in extracted genetic material.

In some embodiments, genes are selected from the group consisting of GAPDH, Beta Actin, Big ribosome protein (RPLPO), CRYAB, EGFR, FOXA1, CD44, ESR1 (ER), PGR (PR), and mutated forms of Myc, Ras, BRCA1, BRCA2, APC, and p53.

In some embodiments, the method comprises the testing for the expression of vimentin, where increased expression of vimentin indicates a mesenchymal CTC.

One aspect of the invention comprises a composition comprising an isolated population of viable CTCs having at least 1 cells of at least 25% purity of CTCs. In some embodiments, the CTCs are breast cancer cells. In some embodiments, composition further comprises an MSC or putative MSC.

BRIEF DESCRIPTION OF THE DRAWINGS

FIG. 4A shows brightfield, and 4B shows a fluorescent image of the same cells. Numerous beads surrounding two cells can be seen in FIG. 4A.

FIG. 5A is aSM014 cell 7, 5B SUBL017 cell 18, and 5C SUBL017 cell 23. FIG. 5 shows numerous beads attached to target cells.

FIG. 6B a single MCF7 cultured cell; FIG. 6C SM014 cell number 7; FIG. 6D SUBL017 cell 18; and FIG. 6E SUBL017 cell 23.

FIG. 8A-F is a series of sketches showing various magnet designs, shown from right to left as FIG. 8A, no magnet; FIG. 8B a single rod below the support plate; FIG. 8C, four sections below the plate; FIG. 8D, narrow single rod below the plate; FIG. 8E, six sections in a casing; and FIG. 8F six sections without a casing. All magnets in these figures have two short sections above the support plate.

FIGS. 10A, B, C, D and E are 5 representative photomicrographs of CTCs isolated from Patients A, B, D, E, and F, respectively.

DETAILED DESCRIPTION OF THE PREFERRED EMBODIMENT

Figure 1A:
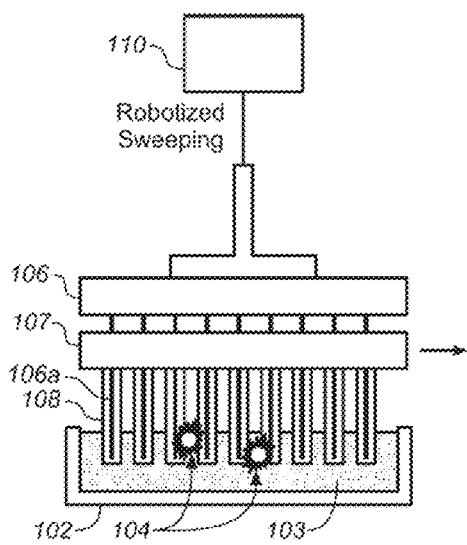
FIG. 1A-D are a series of four illustrations representing a schematic diagram of one embodiment of a device according to the present invention, where magnetic members in the form of wires are used, where 1A shows sweeping to pick up cells; 1B shows lifting of attached cells from the medium; 1C shows deposition of removed cells from 1B into a different medium, and 1D shows separation of the cells from the wires.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification.

Overview of Magnetic Separation Devices and Methods

The devices described below allow one to isolate and purify rare cells such as CTCs by labeling them with magnetically responsive particles and then uses one or more permanently magnetized or magnetizable members such as wires or rods with non-adherent sleeves such as removable sleeves for several rounds of capture-and-release of cells. Analysis and preparation of isolated CTCs is therefore enabled. Throughout the process, cell viability may be maintained (no fixation or permeabilization steps), and all contaminating blood cells are removed. Thus this technology can isolate living circulating tumor cells (CTCs) from patients with metastatic disease for further studies, as well as isolating other rare cell populations. Rare cells generally are those comprising less than about 0.1% of a heterogeneous cell population.

The device may be used for capture and isolation of intact, rare and viable target cells (which may, in certain embodiments, include subcellular components or particles) in a sample having a mixed cell population of target cells and contaminant cells. The target cells may be rare, comprising a very small fraction of the cellular population. For example, rare tumor or fetal or stem cells may be found in adult human peripheral blood. The method and device are also applicable to animals, or other biological tissues, or cell cultures. The target cells are labeled with magnetically responsive material, which may be a ferromagnetic or paramagnetic bead, or an iron or gold nanoparticle, or the like. A paramagnetic material includes, e.g., such as aluminum, magnesium, and platinum, and, as is known, refers to a material which is not ferromagnetic, but is only weakly pulled towards a strong magnet. Ferromagnetic materials such as nickel, cobalt, pure iron, iron alloys, certain rare earths such as gadolinium, dysprosium) etc. are strongly attracted to magnets and are preferred materials for the magnetically responsive particles.

The magnetically responsive particles (e.g., beads) are linked to a ligand specific to the target cell, generally an antibody, but the ligand may also comprise another cell specific ligand, such as a protein or lipid. The choice of ligand can depend on the target cell to be isolated. The devices of the present invention are intended to be automated and perform certain preprogrammed steps automatically and repeatedly. In some embodiments, the technology comprises or is used with one or more containers, as the device carries out certain steps involving thorough sample contact, washing off of contaminating cells, and collection of an enriched target cell population. The containers are designed in certain respects to allow sweeping through a relatively still pool of sample, said sweeping covering a majority, or substantially all, of the surface of the pool. The device comprises a magnetic member constructed, for example, to obtain high magnetic strength. This may be a rare earth magnet or may be a material that is magnetizable, provided that the required field strengths can be obtained. It may be an electromagnet that is capable of being magnetized for capture and de-magnetized for release. The magnetic member has, on its outer surface, in the portion that will contact the liquid, a non-adherent sleeve. In some embodiments, the magnet member is adapted to fit closely into an thin, self-supporting sleeve surrounding the magnetic member to prevent direct contact of sample cells with the magnetic member, said sleeve being tightly fitted to, yet separable from, the magnetic member, said sleeve further being constructed of a material which is non-adherent to cells in the mixed cell population.

By "nonadherent" it is generally meant that the cells (at least 90%, preferably at least 99%) will easily wash off or fall off of the sleeve. The level of adherence of cells to a material such as a plastic can be measured by methods well known in the art. Generally, a material is exposed to a sample containing cells, then the material are exposed to fresh solution, and the number of cells that adhere to the material is determined. For instance, plastic pieces can be incubated in whole blood at room temperature, for example for 30 minutes. The pieces are then washed with phosphate buffer solution (PBS). The number of cells adhered after washing is determined to determine the adherence of the cells. Materials that are non-adherent generally have fewer than 1,000 cells per square millimeter. Particularly useful materials will have even fewer cells, for example less than 100 cells/mm$^2$ or less than 100 cells/mm$^2$. We have found that polyvinylchloride, in particular biological grade polyvinylchloride has less than 100 cells/mm$^2$.

Figure 18:
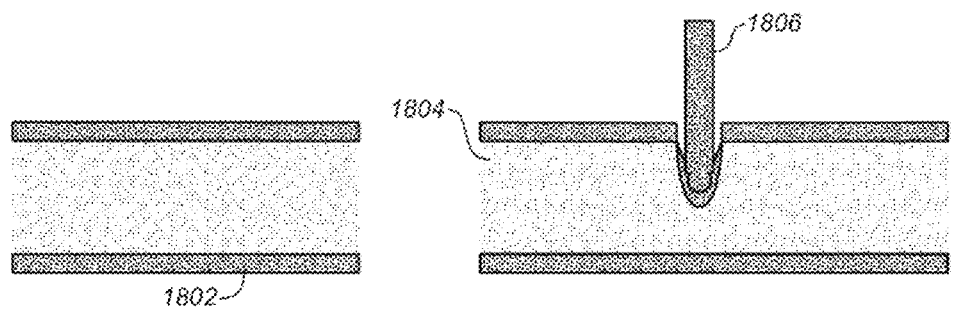
FIG. 18 is a schematic drawing showing a magnetic member inserted into a fluidic channel.

In an alternative embodiment the non-adherent sleeve is not removed, but the magnetic member is demagnetized in order to remove the magnetic field across the non-adherent sleeve to allow release of the cells. In some embodiments, a second magnet is used to facilitate cell removal from the non-adherent sleeve. The second magnet can be, for example, a magnet disposed below the recovery vessel. The magnetically responsive particles, now released from the field of the magnetic member will be attracted to the second magnet, facilitating recovery of the particles. One preferred non-adherent material that can be used as a sleeve is biological grade PVC, which has been found to be surprisingly non-adherent. The non-adherent sleeve is generally nonmagnetic, and "magnetically transmissive," meaning that it is of a material (such as the exemplified organic polymer) and also of a dimension which allows the magnetic force of the magnet to pass through the sleeve with little impedance. To this end, the sleeves are generally constructed to be thin. It is generally contemplated that the sleeve will be on the order of 1 to 1000 μm, in some embodiments, 10-300 μm thick, and in some embodiments, about 10-30 μm thick. The sleeve may be deformable so that it changes shape to accommodate an inserted magnetic member, e.g., as shown in FIG. 18. When the magnet member (or members, there being the possibility of numerous, parallel members having individual non-adherent sleeves) has been immersed in and swept through the sample to thoroughly attract the rare cells, e.g., "stirred" through the sample, in some embodiments, a wash step is used in order to wash off the contaminated cells. The wash step can be performed by spraying or rinsing the magnetic member with a wash solution. The wash step can also be performed by immersing the magnetic member into a container having a wash solution. To this end, there is provided a wash vessel or wash container for holding an immersing wash solution for removing contaminant cells while target cells remain bound to the sleeve. The wash vessel generally holds a volume of liquid sample which is sized for high fluid throughput. To this end, the container may be many times the cross sectional area of the magnet. That is, the magnet may be 0.6 cm diameter, while the container(s) may be on the order of 20 to 50 times larger diameter. After one or more washings, there is provided in the device a recovery vessel or recovery container for holding target cells isolated after removal of contaminant cells. To accomplish the above movements, and the fluid movement, in some embodiments, there is provided an actuator for moving the magnetic member between containers and into and out of containers, whereby the magnetic member is immersed within the mixed cell population; into and out of the sleeve; and in at least two directions within the sample for sweeping the sleeved member through the sample.

The method and device described here can be used to isolate circulating tumor cells (CTCs), and may be used in any case where rare cells or other biological structures can be magnetically labeled for later separation and isolation. The presently constructed device can process, for example, 9 ml blood/1 hr and captures more than 50% of CTCs as measured in spiking experiments. The below-described devices, including an exemplified embodiment known as a MagSweeper, gently enrich target cells such as CTCs by $10^8$-fold from blood. Purified cells can then be individually selected for biochemical analysis. To this end, a device for probing cell clusters washed from a magnetic member is provided. The technology described herein is capable of obtaining capture rates and levels of purity of rare cells obtained from mixed cell populations well above those of other technologies. Capture rate generally refers to the percentage of target rare cells that are captured relative to the target rare cells in the sample. Purity generally refers to the percentage of rare cells over the total number of cells in the final recovered solution, i.e., (number of rare cells)/(number of rare cells plus number of contaminant cells) in the recovered solution. In some embodiments, the technology can achieve 99.9%, 99.99% or 100% purity from a sample with a mixed cell population, e.g., a blood cell population of about 1 in 5 million or greater. In some embodiments, the technology can achieve 90%, 99% or 99.9% purity from a sample with a mixed cell population, e.g., a blood cell population of about 1 in 50 million or greater. In some embodiments, the technology can achieve 90%, 99% or 99.9% purity from a sample with a mixed cell population, e.g., a blood cell population of about 1 in 50 million or greater. In some embodiments, the technology can achieve 25%, 90% or 98% purity from a sample with a mixed cell population, e.g., a blood cell population of about 1 in 500 million or greater.

In some embodiments, the technology can achieve capture rates of 35%, from a sample with a mixed cell population, e.g., a blood cell population of about 1 in 5 million, about 1 in 50 million, or about 1 in 500 million. In some embodiments, the technology can achieve capture rates of 75%, from a sample with a mixed cell population, e.g., a blood cell population of about 1 in 5 million, about 1 in 50 million, or about 1 in 500 million. In some embodiments, the technology can achieve capture rates of 90%, from a sample with a mixed cell population, e.g., a blood cell population of about 1 in 5 million, about 1 in 50 million, or about 1 in 500 million.

In some embodiments, the technology can achieve a combination of capture rate and purity above what is achieved with current methods. In some embodiments, the technology can achieve a 35% capture rate and 99.9%, 99.99% or 100% purity from a sample with a mixed cell population, e.g., a blood cell population of about 1 in 5 million or greater. In some embodiments, the technology can achieve a 35% capture rate and 90%, 99% or 99.9% purity from a sample with a mixed cell population, e.g., a blood cell population of about 1 in 50 million or greater. In some embodiments, the technology can achieve can achieve a 35% capture rate and 90%, 99% or 99.9% purity from a sample with a mixed cell population, e.g., a blood cell population of about 1 in 50 million or greater. In some embodiments, the technology can achieve can achieve a 35% capture rate and 25%, 90% or 98% purity from a sample with a mixed cell population, e.g., a blood cell population of about 1 in 500 million or greater.

In some embodiments, the technology can achieve a combination of capture rate and purity above what is achieved with current methods. In some embodiments, the technology can achieve a 75% capture rate and 99.9%, 99.99% or 100% purity from a sample with a mixed cell population, e.g., a blood cell population of about 1 in 5 million or greater. In some embodiments, the technology can achieve a 75% capture rate and 90%, 99% or 99.9% purity from a sample with a mixed cell population, e.g., a blood cell population of about 1 in 50 million or greater. In some embodiments, the technology can achieve can achieve a 75% capture rate and 90%, 99% or 99.9% purity from a sample with a mixed cell population, e.g., a blood cell population of about 1 in 50 million or greater. In some embodiments, the technology can achieve can achieve a 75% capture rate and 25%, 90% or 98% purity from a sample with a mixed cell population, e.g., a blood cell population of about 1 in 500 million or greater.

In some embodiments, the technology can achieve a combination of capture rate and purity above what is achieved with current methods. In some embodiments, the technology can achieve a 90% capture rate and 99.9%, 99.99% or 100% purity from a sample with a mixed cell population, e.g., a blood cell population of about 1 in 5 million or greater. In some embodiments, the technology can achieve a 90% capture rate and 90%, 99% or 99.9% purity from a sample with a mixed cell population, e.g., a blood cell population of about 1 in 50 million or greater. In some embodiments, the technology can achieve can achieve a 90% capture rate and 90%, 99% or 99.9% purity from a sample with a mixed cell population, e.g., a blood cell population of about 1 in 50 million or greater. In some embodiments, the technology can achieve can achieve a 90% capture rate and 25%, 90% or 98% purity from a sample with a mixed cell population, e.g., a blood cell population of about 1 in 500 million or greater.

As described elsewhere herein, one embodiment of the MagSweeper comprises a round-bottom neodymium magnetic rod covered with an thin (25 µm) non-adherent plastic sheath. The plastic material reduces the non-specific binding of contaminant cells and does not impair magnetic binding. An exemplified member was constructed as a rod about 6 mm in diameter with a magnetic flux density of about 0.7 Tesla at the rod end. The magnet with the non-adherent sleeve sweeps the entire well in a continuous motion to maximize the capture efficiency of magnetically-labeled cells. That is, a relatively large volume containing the mixed cell population can be contained in a well, which has a relatively shallow depth compared to a relatively larger diameter or width. In one embodiment a sleeved rod is robotically driven in a preprogrammed pattern to sweep through the well containing the sample in a pattern of overlapping concentric circular loops that cover the essentially the entire well area without scraping the walls of the well. It has been found that the choice of the velocity of the magnetic member relative to the solution (the sweep velocity) during the continuous relative motion is important for to maximize (i) cell capture efficiency; (ii) application of sufficient shear force to detach adsorbed non-magnetically-labeled cells; and (iii) prevention of damage to the rare target cells. The optimum sweep velocity can also depend on the magnetic strength of the A sweep velocity of about 2 mm/sec has been found to provide efficient capture.

The relative movement or motion between the magnetic member and the sample solution is generally a continuous relative movement. It is not sufficient to have the motion supplied by placing the magnetic member into and out of the solution. The movement must generally be a continuous motion creating a shear across the magnetic member for a time sufficient for the magnetic member to contact a significant portion of the sample solution. The continuous motion is generally a gentle motion in the range of non-turbulent flow. The continuous motion is sufficient where it provides for the selective capture of rare target cells as compared to contaminant cells in the sample solution.

We have found that the continuous relative movement having a velocity between the magnetic member and the solution of about 0.5 mm/sec to about 5 mm/sec provides high capture efficiency. In some embodiments, a range of velocities between 1 mm/sec and 4 mm/sec is used. In some embodiments, the velocity between the magnetic member and the solution range of about 0.5 mm/sec to about 5 mm/sec when the surface magnetic field is in the range of between 0.1 Tesla and 1 Tesla. In some embodiments, the velocity between the magnetic member and the solution range of about 0.5 mm/sec to about 5 mm/sec when the surface magnetic field is in the range of between 0.1 Tesla and 1 Tesla. In some embodiments, these levels of velocity and magnetic field are used for a magnetic rod between 2 mm and 10 mm in diameter, for example with a neodymium magnet.

We have found that continuous relative motion should produce a velocity between the magnetic member and the solution which generally should be a velocity such that the system is in the non-turbulent flow regime. A non-turbulent flow regime is a regime in which the flow of the solution in the region of interest flows without creating turbulence. In some cases this can be the laminar flow regime. It is well known in the field of chemical engineering the factors that can be controlled in order to maintain a non-turbulent flow regime. The factors include solution viscosity, rate of flow, and geometrical factors. While not bound by theory, it is believed that by maintaining a flow rate, i.e., relative motion between the magnetic member and the sample liquid, which provides a non-turbulent flow regime, sufficient shear is provides in order to wash off contaminant cells, but the flow is not so violent as to damage the rare target cells, resulting in intact and/or viable cells after capture and release.

The appropriate velocity between the magnetic member and the solution can also be expressed in terms of Reynolds number. The Reynolds number is a well known parameter in chemical engineering. We have found that a Reynolds number between 0.1 and 100 can provide high capture efficiency of intact or viable cells. In some embodiments, a Reynolds number of between 0.5 and 50 is used. In some embodiments, a Reynolds number of between 1 and 20 is used. In some embodiments, the Reynolds number is between 0.5 and 50 and the magnetic field is in the range of between 0.1 Tesla and 1 Tesla. In some embodiments, the Reynolds number is between 1 and 20 and the magnetic field is in the range of between 0.1 Tesla and 1 Tesla. In some embodiments, these levels of Reynolds number and magnetic field are used for a magnetic rod between 2 mm and 10 mm in diameter, for example with a neodymium magnet.

The continuous relative motion between the magnetic member and the sample solution is also useful for ensuring that a significant portion of the sample has access to the magnetic member, or a significant portion of the sample experiences the magnetic field from the magnetic member sufficient to capture the magnetic particles in the solution. In some cases it is desirable that a significant portion of the sample, a majority of the sample, or substantially all of the sample has access to the magnetic member.

For example, in 1 ml of blood there are typically about 5 billion total cells and 10 million white blood cells. This sample of blood may contain different quantities of target cells as noted below and these cells are isolated with the devices and methods of the invention with the following purity levels:

Circulating Rare cells (e.g., fetal cells or circulating tumor cells). Typically 5 to 1,000 cells per ml of blood. Typical purity ranges from 50%-99.9% upon isolation with device depending on starting quantity.

Stem cells (e.g., cancer stem cells). Typically ~100,000 cells per ml of blood. Typical purity ranges from 98%-100% after isolation with device.

Neutrophils (e.g., neonatal immune response). Typically million to 5 million cells per ml of blood. Typical purity ranges from 99%-100% after isolation with device.

Sequential rounds of capture-wash-release-recapture can be used to reduce or eliminate background contaminant cells that are not specifically labeled with magnetic particles. In some cases, a second or third round will improve the purity by but will do so at some cost to the capture efficiency. Subsequent rounds are used for situations where the ratio of the rare target cells to the contaminant cells is high, for example greater than 1 to 50 million.

Figure 9:
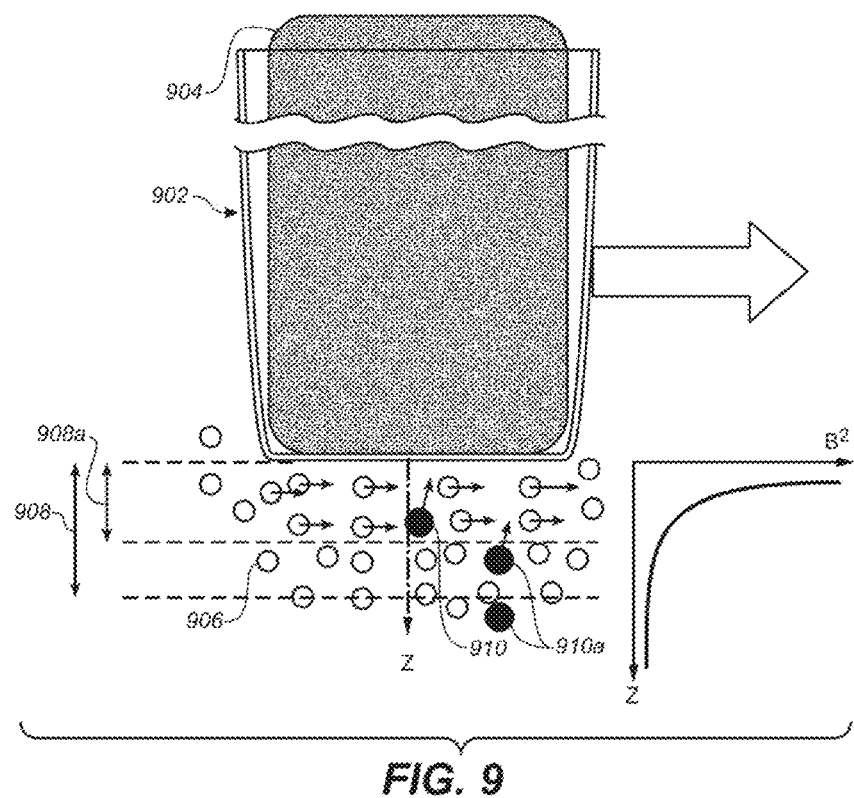
FIG. 9 is a drawing showing the magnetic profile of a magnetic rod in a plastic sleeve. On cells with attached magnetic beads (black circles), the magnetic rod produces a magnetic force in z proportional to the non uniformity ($dB^2/dz$) of the magnetic field, thus imparting momentum in a z direction proportional to ($dB^2/dz$) and to a dwell time that depends both on the sweep speed and on the velocity distribution across the boundary layer that extends into the fluid from the surface of the sleeve. On cells with no beads (open circles) only a transverse force in the direction of sweeping (large arrow) acts on the cell. To capture a labeled cell, the transverse momentum must be sufficient to overcome the drag of the fluid on the cell so that it reaches the sleeve surface within the dwell time. Magnetic strength and sweep speed were controlled for these parameters to obtain high capture efficiency at the tip of the magnetic member.

Cell trajectories for the devices and methods of the invention under the influence of magnetic force and the fluid drag force were modeled. Not to be bound by theory, these models indicate that cell capture occurs when the accelerated labeled cell through the magnetic force overcomes the sweeping velocity and the corresponding viscous drag force of fluid flowing around the magnet. To find the capture zone around the magnet, numerical models that simulated the magnetic field, fluid flow, and trajectories of labeled cells as a function of the sweeping parameters were developed. By calculating the magnetic field using a finite element model of the magnetic rod, it was found the magnetic flux is appreciable (>0.1 T) only near the rounded tip of the magnet and drops off rapidly away from the magnet. This result emphasizes the importance of employing thin non-adherent sleeves in order to minimize the attenuation of the magnetic field from the magnetic member and, consequently, improve the overall capture rate. In addition, it was found that the magnet with the rounded tip has an increased (50%) surface magnetic flux density compared with the unmodified (blunt tip) magnet. To estimate the magnetic force applied to the beads, a variable magnetic susceptibility for the beads was used, based on the manufacturer's bulk magnetization data. The travel velocity of labeled cells was calculated by adding the magnetic force-driven velocity, which was determined by Stoke's drag law, to the fluid velocity, assuming a 10 μm diameter cell labeled with a single 4.5 μm diameter magnetic bead. The resulting 3-D fluid motion has a significant impact on the particle capture. As illustrated in FIG. 9, there exists a capture plane beneath the magnet indicated by dotted lines between arrow 908. There was a gap in the annular capture zone, even though the magnet has completed one full orbit. This is a consequence of the "stifling" of the fluid by the magnetic member (rod), which pushes particles ahead of the magnet. At the higher z-planes, where magnetic fields are weak, there is a dramatic reduction in capture area. Here, particles mostly travel around the magnet and through the wake without being captured. The device is therefore optimally designed to cover at least one circuit through the entire well, and may advantageously be swept through the well multiple times.

For scale, the maximum plotted velocity vector of the magnetic velocity field is 7.8 mm/sec (at r=2 mm, z=−2.5 mm). The true maximum occurs adjacent to the magnet surface at the tip (~12 mm/sec). (c) Lateral trapping boundaries for an idealized fluid-porous magnet as a function of magnet sweeping velocity. (d) xy-trapping boundary 1.5 mm below the magnet tip (z=−4.68 mm) for the idealized flow. (e) Fluid velocity within the well calculated for a magnet velocity of 2 mm/sec and orbit radius of 6 mm. The vectors indicate the instantaneous flow velocity in the xy-plane near the top of the curved section of the magnet (z=−0.2 mm) and the color gives the flow magnitude. The fluid velocity field was used to calculate particle trajectories and capture times. (f) Cell trapping profiles in the xy-plane located beneath the magnet (z=−4.8 mm). (g) Cell trapping profiles at the fluid surface (z=3.5 mm). (h) Superimposed capture boundaries for one full orbit period (18.85 sec).

In some embodiments of the invention, no sample processing of blood is required prior to MagSweeper use, which decreases operator hands-on time and risk for perturbing the CTCs. The MagSweeper can process 9 ml blood/hr with 3-5 minutes total hands-on time, and capture more than 50% of CTCs as measured in spiking experiments without significant change to the captured cell gene expression. Another advantage of MagSweeper is the flexibility in the starting sample volume and the process scalability. As a result, the throughput of the device can be increased by sweeping an array of sheathed magnetic rods through multiple samples in parallel with a single motion-controlled system. The device has successfully purified 1-1.5 million neutrophils/ml of whole blood (data not shown), which suggests that the MagSweeper is capable of purifying a wide dynamic range of cell counts.

In regions of high magnetic field gradient (e.g., near the rounded tip of the magnet), labeled cells are efficiently captured, resulting in a large sweep area. As noted above, the main influence of the fluid motion in this region is the presence of a small gap of uncaptured particles left following a single orbit. A simple first alternative is the extension of the sweep to overlap a portion of the circumference (~10%), thus capturing the remaining particles. The effect of fluid motion is strong in regions of low magnetic-field gradient, leading to a significant reduction in capture cross-section. This is addressed with small steps (1 mm) in orbit radius.

This device has the demonstrated ability to efficiently capture living epithelial cells from a sample, such as a blood sample (e.g., peripheral blood) while removing all contaminating cells. This exemplified device comprises magnetized members covered with non-magnetic, non-adherent, e.g., plastic, sleeves that can be robotically controlled to sweep or be swept through a blood sample that has been pretreated with a label, such as Epithelial Cell Adhesion Molecule (EpCAM) antibodies linked to magnetic particles. An EpCAM antibody is commercially available from Abcam. It recognizes a 40 kD transmembrane epithelial glycoprotein (EGP40), also identified as human epithelial specific antigen (ESA) or epithelial cellular adhesion molecule (EpCAM). Cells or other labeled structures are gently captured in the living state but at much higher capture and purity rates than any currently available commercial technology.

In some embodiment the devices of the invention utilize a "sweeping" effect to provide a continuous relative motion which causes the sample to flow gently past the sleeved magnet. The sweeping effect can be accomplished in a number of ways. In some embodiments, the magnetic members immersed in the sample are moved in a predetermined pattern through the while the container holding the sample is held stationary. Alternatively, the device may be constructed to move the containers relative to the magnets. In other embodiments, the magnetic member with the non-adherent sleeve can be held stationary while various solutions are passed by the magnetic member. The present method and device can use a continuous movement through a substantial portion of the container holding the sample, which movement causes at least a majority of the sample volume, in some cases, substantially all of the sample volume, to contact the sleeved magnetic member. In other words, the movement pattern is designed to trace a pattern that traverses all or nearly all of the container area. The movement may be defined in an x-y horizontal axis representing length and width (or, r representing a radius) with a z dimension representing vertical. Movement will be primarily in an x-y or r direction, with different depths optimally provided along a z axis. The container may be a simple well-like container for holding an unobstructed pool of sample. The present method and device does not require the use of containers which comprise flow channels or a particular fluid flow path; the sample is merely present in an open pool where it can be acted upon when the sleeved magnetic rod is inserted into the pool. Target cell attachment to a side of the container is to be minimized. The present method also does not require (but may employ) a pre-selection step based on cell size; the sample need not be pre-treated but may simply be diluted in buffer for convenience (e.g., to prevent clotting) and extracted as-is. The present methods also do not require a chemical processing step, as does other methods, in which the CTCs are fixed and permeabilized, so the present method may result in viable, intact cells. The present device further employs a controllable robotic movement device for reproducible, predetermined, continuous patterned movement of the magnetic members relative to the sample.

In one embodiment, the magnetic members are alternatively magnetizable and de-magnetizable by contact with an electric field a magnet, or the like. In FIG. 1, the magnetic members 106a are magnetized, for example, through contact with a magnet contained in assembly 106. This is accomplished by making the members 106a out of magnetizable material. Magnetization occurs not just in materials having permanent magnetic moments but also in any magnetizable material in a field which can induce a magnetic moment in its constituent atoms. In the special case of Neodymium Magnet $M=\chi H$ A m$^{-1}$.

Where M is magnetization and H is magnetic field strength, given in amperes per meter (A m$^{-1}$).

Thus, certain materials may be magnetized and demagnetized. The present magnetic member possesses high field strength in order to capture a significant fraction of magnetically labeled cells.

The term "high field strength" as used herein generally means a field strength that is capable of attracting and capturing the magnetically responsive particles. In some cases the field strength comprises a magnetic flux density of at least 0.3 Tesla, preferably at least 0.5 Tesla, generally up to about 1 to 1.2 Tesla. In some embodiments, the magnetic flux density is measured at the point on the magnetic member outside the non-adherent sleeve that is the point of highest magnetic flux density. In the case of a rod, the magnetic flux density is measured at the tip of the rod. Magnetic field strength maybe measured as supplied by the magnet manufacturer, or by a gauss meter. The field strength required, the high field strength, is also measured in practical terms, such as by pull strength. The pull force may be tested by placing the magnet between two 1" thick flat ground plates of alloy steel. One plate is attached to a digital force gauge which records the tensile force on the magnet. The plates are pulled apart until the magnet disconnects from one of the plates. The peak value is recorded as the "pull force". The present high field strength magnets will have a pull strength of at least about 30 pounds, preferably at least about 70 pounds. Effective high field strengths may be obtained, for example from neodymium magnets.

Cell Surface Markers

Many different cell surface markers can be targeted with specific ligands, and the ligands may be made magnetically responsive by a number of reagents. For further information, see, for example, *Stem Cells*, Vol. 25 No. 3 Mar. 2007, pp. 646-654, which discloses that human first-trimester fetal blood, liver, and bone marrow MSC but not adult MSC express the pluripotent stem cell markers CD44, CD96, Nanog, Rex-1, SSEA-3, SSEA-4, Tra-1-60, and Tra-1-81. This enables the isolation of rare fetal blood cells from maternal blood cells by the use of ligands (e.g., antibodies) to these cell surface markers. Also, patient specific stem cells may be isolated by the present method. Fetal nucleated red blood cells may be isolated, although rare, from maternal blood cells using anti CD71. For further information on isolation of fetal nucleated blood cells, see Pittenger et al. (1999) *Science*, 284: 143-147 [3462].

Described below are findings from isolated single CTCs that were recognized using antibodies to human EpCAM (epithelial cell adhesion molecule). There are many cloned antibodies to EpCAM (formally called TACSTD1 and also known as ESA). One of many monoclonal antibodies to EpCAM is HEA 125. For a list of others, see www(dot)abcam.com/index.html?t=6920&pt=1&c=612.

Epithelial cell isolation techniques exemplified here can be applied to other sarcomas, adenosarcomas or carcinomas (epithelial malignancy), including prostate, breast, colon, colorectal and lung cancers. (See for further information on applicable malignancies, *Clinical Cancer Research*, Vol. 5, 4158-4163, December 1999. A more detailed listing of carcinomas is set forth in Allard et al., "Tumor Cells Circulate in the Peripheral Blood of All Major Carcinomas but not in Healthy Subjects or Patients With Nonmalignant Diseases," *Clinical Cancer Research*, Vol. 10, 6897-6904, Oct. 15, 2004, cited for further information. Carcinoma cells are known to express the human Epithelial Antigen (recognized by the monoclonal antibody HAE125). Other human carcinoma antigens (HCA) are known, as described e.g., in U.S. Pat. No. 5,693,763 to Codington, et al., issued Dec. 2, 1997, entitled "Antibodies to human carcinoma antigen," which is cited for further information.

As another example, fetal cells may be isolated from maternal cells in a mixed blood sample using an antibody to CD 34 (See US 20080254460). Also, a variety of cell surface markers are known to which antibodies or other labeling agents may be or have been made. These markers include the above-mentioned CD 34, as well as CCR7, CD38, CD43, CD48, CD90, CD105, CD117/c-kit, CD123, CD135/Flk2, CD144 (VE-cadherin), CD150, CD2338/ABCG2, c-Met, Nanog, Notch-1, SSEA-1, SSEA3, SSEA-4, Tra1-60 (podocalyxin) and Tra1-81 (podocalyxin).

Another stem cell marker is described in Bhatie, "AC133 expression in human stem cells," *Nature*, 15:1685-1688 (2001), which is cited for further information, which reports that AC133+ cells are present in the peripheral circulation of mobilized and non-mobilized adults, and in the bone marrow compartment. These cells may be isolated and cultured according to the methods described here. According to the present methods, magnetic beads may be prepared having one maker, then cells isolated using this marker may be further separated with a different marker, so that the resultant population comprises only cells expressing both markers.

Bacteria and viruses may also be isolated even though present in small numbers in a cell population. For example, HIV present in low copy number in a blood sample may be detected and isolated for further culture and genetic study by use of a specific monoclonal antibody such as the monoclonal antibodies described in U.S. Pat. No. 6,818,392.

Removal of Cells

The captured cells are released from the covered magnetized members into a recovery solution, such as a capturing buffer by removing the magnetic field across the non-adherent sleeve. To ensure removal of all contaminating cells, the device may go through multiple rounds of capture, and release. In addition, wash steps are generally employed between capture and release steps. The cells released from the sleeve have been shown to be viable and unaltered. The beads may be removed from the isolated cells through the use of a cleavable linker between the beads and the bound antibody for example. Chemically cleavable moieties that may be incorporated into the linker include: dialkoxysilane, β-cyano ether, amino carbamate, dithoacetal, disulfide, and the like. Also, nucleic acid linkers can be used, with restriction enzyme or other endonuclease recognition sites built in to the sequence. For a further description of cleavable linkers, see U.S. Pat. No. 6,664,079 to Ju, et al., issued Dec. 16, 2003, entitled "Massive parallel method for decoding DNA and RNA."

Magnet Arrangements

Preferred embodiments of the device comprise a collection of axially magnetized rods of larger diameter compared to the above-described wires. These may be 1 to 10 mm, 2.5 to 7 mm in diameter, or 4-6 mm in diameter, and are significantly higher in magnetic field strength than the needle configuration. The rods can be attached to a 5 function/3 axis robot for moving the rods in a predetermined motion in a sample well that is of much greater cross sectional size than the magnetic rod. Upon activation of the robot, the magnetic rod is inserted into an thin, tightly fitting plastic sleeve and lowered into a liquid sample (e.g., human blood) that has been previously mixed with magnetic beads attached to antibodies specific for a target biomarker (e.g., cancer cells labeled with immunomagnetic beads). The robotic arm then sweeps the magnetic rod through the liquid to capture the magnetically labeled targets (e.g., cancer cells). The robotic arm lifts the magnetic rod and captured biologics and then moves in a linear direction to the next station, where it lowers into a washing solution. The rod agitates/sweeps within the wash solution, during which time contaminants fall off the magnetic rod. The wash solution may be drained and refilled multiple times to ensure complete removal of contaminants. The robot then moves the magnetic rod to a final release station. Here the magnetic rod is lifted out of the plastic sleeve, removing the magnetic field across the non-adherent sleeve, leaving the plastic sleeve in the release fluid. The robot may shake the release fluid and cells or biologics on the plastic sleeve fall into the release fluid for further analysis. Any of the capture, wash, or release steps may be repeated for complete capture and purity. In some embodiments, a second magnet is used during the release step to assist in releasing the beads from the non-adherent sleeve.

Non-Adherent Sleeves

The surface area and the geometry of the magnet design and the type of non-adherent sleeve, such as a plastic sleeve, can be adjusted to reduce nonspecific adherence of contaminating cells and captured cells to the plastic. The robot permits control over the number and stringency of washes to ensure complete clearance of contamination.

A variety of materials which are non-adherent to red or white blood cells may be used.

U.S. Pat. No. 3,723,754, French patent publication 2,089, 788 and Japanese application Ser. No. 45/75116, disclose a device for blood storage and for dynamic flow of blood there through. As described there, polyvinylidene fluoride has desirable properties which may be employed in the present device. A preferred material, PVC (polyvinyl chloride), may be flexible, i.e., mixed with plasticizers. Plasticizers such as Di-2-ethylhexyl phthalate (DEHP) may be used to form up to 40% of the dry weight of flexible plastic used. Generally, little or no plasticizer is needed because the non-adherent sleeve is thin and in some cases is self supporting.

Polyurea-polyurethane sleeves may also be used, and prepared as coatings of U.S. Pat. No. 5,169,720 are prepared from high molecular weight isocyanate end-capped prepolymers substantially or exclusively comprised of ethylene oxide units. At least 75%, preferably at least 90%, of the prepolymer units are oxyethylene-based diols or polyols having molecular weights of about 7000-30,000, with essentially all of the hydroxyl groups capped with polyisocyanate prior to formation of the hydrated polymer coating.

In addition, ceramic materials have been described as compatible with blood. See, U.S. Pat. No. 6,158,984 describing ceramic materials. polyHEMA (hydrophilic hydrogel poly(2-hydroxyethyl methacrylate) is also known to reduce cell adherence and may be used alone or in combination with other materials.

Non-adherent materials are also described in U.S. Pat. No. 6,663,584. One may therefore, according to the present teachings, adapt non-adherent, physiologically inert, liquid-repellent polymer such as fluorocarbon, including the chlorofluorocarbon, polymers or silicone polymers for use here.

In one aspect, it is important that the device employ a thin sleeve, which can still be fitted on to and removed from the magnetic member. By thin it is generally contemplated that the sleeve will be on the order of 1 to 1000 µm, preferably 10-300 µm thick, preferably about 10-30 µm thick. The thinness or thickness may be adjusted to control the degree to which the magnetic field is transmitted through the sleeve and the strength of the sleeve material. The sleeve will generally be self-supporting, in that the magnetic member will be fully applied (e.g., inserted), and at least partially removed (e.g., withdrawn) or wholly removed repeatedly during operation, requiring a certain degree of structural integrity in the sleeve. It is not strictly required that the sleeve be rigid or immobile when the magnetic member is removed. In order to facilitate release of the beads, the sleeve should generally not contain or retain a magnetic field, although it may be paramagnetic.

Where a sleeve is used as the non-adherent sleeve, the sleeve is generally designed to form a surface on the outside of the magnetic member which allows the magnetic field from the magnetic member to either pass through the sleeve or which is temporarily magnetized itself when and only when the magnetic member is in close proximity to the sleeve. It is preferred that the rods and sleeves will be cylindrical to facilitate application and removal of the sleeves, but other configurations, such as curvilinear, can be designed given the present teachings.

Magnetically Responsive Particles

Various types of magnetic beads can be used for attachment to the cells to be isolated, in addition to the exemplified CELLECTED Dynabeads®, which are available from Dynal. Dynebeads are Dynabeads® are superparamagnetic, monosized polymer particles. The kit contains 5 ml "CELLection"™ Dynabeads" (4.5 m) coated with the monoclonal antibody against the human epithelial antigen EpCAM and DNase Releasing Buffer.

Streptavidin-coated paramagnetic beads (2.8 µm diameter, M-280) beads may be obtained from Dynal Corp. in Lake Success, N.Y. Streptavidin-coated colloidal ferrofluid magnetic particles, or "MACS", beads may be obtained from Miltenyi Biotec Corp. in Auburn, Calif. By using streptavidin-coated beads, one may specifically attach these beads to biotin-labeled antibodies or other cell type specific proteins. As an example of this implementation, one may refer to the presently marketed BD IMag™ Cell Separation System. This system utilizes magnetic bead technology for enrichment or depletion of specific cell populations in a prepared sample. BD Biosciences Pharmingen provides antibody-labeled magnetic particles for enrichment or depletion of leukocyte subpopulations. Similar particles may be prepared for stem cell markers. BD IMag particles range in size between 0.1 and 0.45 µm and are coated with BD Pharmingen monoclonal antibodies.

Magnetically responsive particles as used here may be magnetic, superparamagnetic or paramagnetic. Magnetically responsive particles are further described in U.S. Pat. No. 5,628,407 to Gilbert, et al., issued May 13, 1997, entitled "Method and apparatus for separation of magnetically responsive spheres."

In one aspect, the present invention comprises the use of large magnetic beads. The term "large magnetic beads" means magnetic beads (>1 microns to about 10 microns) in size. This is distinguishable from small (0.7-1.5 microns), or colloidal (<200 nm) magnetic particles, which are also referred to as nanoparticles.

Cell Isolation and Study

The method described here also comprises a use of the present device which permits the isolation of intact, viable cells, especially CTCs. By way of comparison, an FDA-approved device was used with increased stringency of the approved wash step to improve purity, but the captured cells were "beat up" in the process and not suitable for further multiplex molecular analysis. Cell membranes were torn off the captured cell with spillage of the cell's nuclear material that was intended for analysis. The present device is used with specified sweeping conditions and wash conditions that greatly improve the recovery of viable CTCs.

The present methods do not rely on detecting a specific nucleic acid sequence in a malignant cell in order to identify a cell as a CTC. They enable the isolation of an intact cell for study of multiple gene expression. As described below, the present method may comprise further steps, once CTCs have been isolated in an essentially pure composition, of studying expression in one or more of those isolated cells of standard breast cancer biomarkers, such as ER (estrogen receptor, further defined at *PNAS*, Aug. 29, 2006 vol. 103 no. 35 13162-13167), PR (progesterone receptor, further defined in *Molecular Endocrinology*, 12 (9): 1334-1342) and HER2 (human epidermal growth factor receptor 2, also called HER2/neu or c-erb2, further defined in *Proc. Natl. Acad. Sci. USA*, 1999 Sep. 14; 96(19): 10869-10874). In work described below, it was determined that ER positive primary tumors may contain ER negative CTCs. Also, a HER2 positive primary tumor may result in HER2 negative CTCs. Of further interest, it is demonstrated below that the CTCs are heterogeneous—one CTC from patient B expressed HER2, while three others did not. It was also determined using the present cell separation method that metastatic breast cancer CTCs frequently express vimentin and CD44. Thus, the present method enables CTC study which may be used for further diagnostic purposes, such as in metastatic breast cancer. If a therapeutic target is present or absent, such as EGFR, HER2, ER or PR, will determine whether or not such a targeted therapy is appropriate. Also, in that disease, one may use analysis of CTCs to classify them as representing mesenchymal-like cancer stem cells (MSC) or partially differentiated epithelial cells (PDEs), where the presence of less differentiated CTCs represents a hallmark of progressive metastatic disease.

Cancer-derived stem-like cancer cells obtained by the side population technique are described in Patrawela et al., "Side Population Is Enriched in Tumorigenic, Stem-Like Cancer Cells, whereas ABCG2+ and ABCG2− Cancer Cells Are Similarly Tumorigenic," *Cancer Research*, 65:6207-6219 (Jul. 15, 2005). Some of these cells were characterized as mesenchymal. Thus, using the present teachings, one may isolate CTCs and study those isolated cells further, which will lead to the isolation of a putative mesenchymal-like cancer stem cell (MSC) which may be identified as less differentiated mesenchymal cells, or according to traits identified in the literature as involving the epithelial to mesenchymal transition, or by gene expression studies as described below. Further guidance on identifying MSCs is given in Mani et al. "The Epithelial-Mesenchymal Transition Generates Cells with Properties of Stem Cells," *Cell*, 133:704-715 (May 16, 2008). Further guidance on identifying MSCs is given below under the heading "Isolation of CTCs from metastatic breast cancer patients," where it is explained that the present methods include the detection of increased vimentin expression in CTCs, where vimentin is a mesenchymal cell marker.

Another aspect of the present device and method involves multiple gene analysis from a single cell, where a cell is isolated, and a number of genes (exemplified as 15-48 genes) are analyzed for expression level in a single cell. The analysis may involve steps where the cell's RNA is pre-amplified with a reverse transcriptase PCR method and then tested by amplification simultaneously in multiple chambers of a microfluidic device. Alternative target genes to those specifically exemplified here are contemplated. For example, pAkt/mTOR and p4E-BP1, may be analyzed in CTCs obtained by the present method, see Akcakanat et al., "Comparison of Akt/mTOR signaling in primary breast tumors and matched distant metastases," *Cancer*, 112:2352-2358 (2008).

An exemplary panel of genes suitable for CTC characterization is presented below, where the full name, taxonomy and sequence may be obtained from NCBI under the GeneID given. GeneID. The Entrez Gene GeneID is unique across all taxa. One can therefore convert any GeneID into its current names by using the definitions provided in the file available as ftp: ftp.ncbi.nlm.nih.gov/gene/DATA/gene_info.gz.

TABLE 1

| PTEN | IGF-1R | HER2 (ERBB2) | EGFR | c-MYC | PI3K |
|---|---|---|---|---|---|
| Gene ID 5728 | Gene ID 3480 | Gene ID 30300 | Gene ID 1956 | Gene ID 4609 | (Phosphoinositide-3-kinase) Gene ID5294 |
| AKT | mTOR | MAPK | ER | PR | GSTP1 |
| Gene ID 207 (this is AKT1 | (FRAP1) Gene ID 2475 | (MAPKSP1) Gene ID 8649 | Gene ID 2099 | Gene ID 5241 | Gene ID 2950 |
| BCAR1 | ALDH1 | CD44 | Vimentin | Notch 1 | Galectin 1 |
| Gene ID 9564 | Gene ID 216 | Gene ID 960 | Gene ID7431 | Gene ID 4851 | Gene ID 3956 |
| HSP70 | Glut 1 | LOX | VEGF | VEGF-R | BCL2 |
| Gene ID 3308 | Gene ID 6513 | Gene ID 4015 | Gene ID7422 | (FLT1) Gene ID 2321 | Gene ID596 |
| BAX | Caspase 4 | Cyclin B2 | P63 | Osteopontin | MDR 1 |
| Gene ID 581 | Gene ID837 | Gene ID 9133 | Gene ID 8626 | Gene ID 6696 | Gene ID 5243 |
| beta-ACTIN | GAPDH | RPLPO | GUS | TFRC | G6PD |
| Gene ID 60 | Gene ID 2597 | Gene ID 6175 | Gene ID- none-beta glucuronidase reported gene | Gene ID 7037 | Gene ID 2539 |

TABLE 1-continued

Additional Genes Used in Figs

| Ep-CAM Gene ID 4072 | CK19 Gene ID 3880 | CRYAB Gene ID 1410 | FOXA1 Gene ID 3169 | VIM Gene ID 7431 | FoxC1 Gene ID 2296 |
|---|---|---|---|---|---|
| CD24 Gene ID 100133941 | | | | | |

The profile set should include standard markers, such as, for breast cancer, ER, PR, HER2, and a proliferation marker such as cyclin B2. In addition, markers can be chosen from biologically relevant processes such as signal transduction pathways involved in tyrosine kinase receptor activity, markers of hypoxia, markers of cancer stem cells, genes involved in oxidative stress, drug resistance, apoptosis, and epithelial-mesenchymal transition. Although a housekeeping/reference gene is not supposed to vary in different cell samples, many do. For example, GAPDH has been recently shown to vary when cells shift to a pentose phosphate pathway during hypoxia, and G6PD levels can vary in different tissues. As an initial product, one should choose the housekeeping genes listed in the bottom row of the table above, as five of these are used as reference genes in the FDA-approved 21-gene Oncotype DX RT-PCR tissue assay from Genomic Health.

The methods exemplified below use the MagSweeper technology to capture and purify CTCs for multiplex expression analysis at the single cell level, as well as determining single cell CTC heterogeneity in some patients which may reflect heterogeneity among multiple metastatic sites. To perform single cell analysis, the exemplified method manually identifies and extracts each individual CTC in a post-processing step following CTC capture and purification.

II. Magnetic Coupling and Wire Embodiment ("MagBrush")

In this embodiment, the rods or magnetic members are not themselves magnetic, but are made magnetic through coupling to a strong magnet, or, alternatively, made with an electromagnet.

Figure 1B:
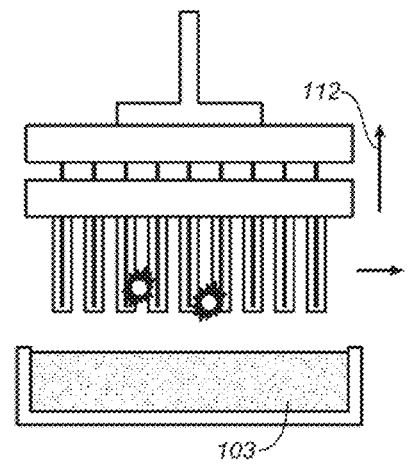
Figure 1C:
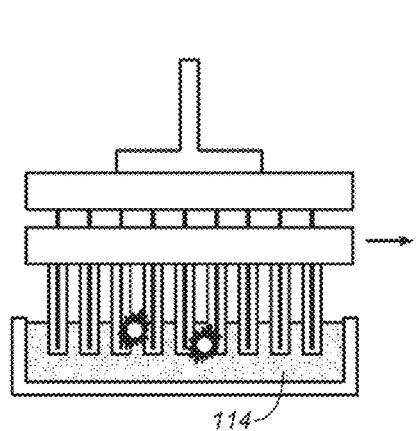
Figure 1D:
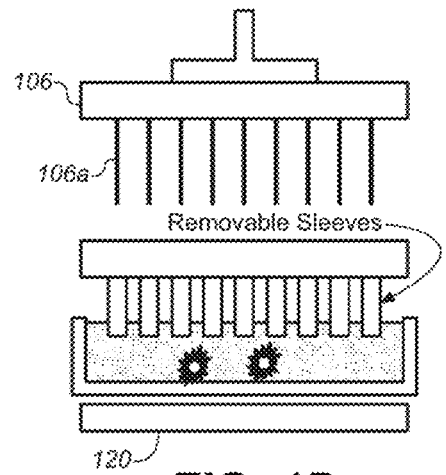

Referring now to FIG. 1A-D, a container 102 holds a sample fluid 103, such as blood, which contains a small population of cells 104 (e.g., CTLs) containing a magnetically responsive label. A magnetic support 106 comprises a magnetic or electromagnetic portion which imparts a magnetic field to a number of magnetizable wires 106a which are attached to the support and inserted into a sleeve array containing a matching number of sleeves 108 held on a sleeve support 107. Thus the wires 106a, each covered by an individual sleeve 108 surrounding the distal portion of the wire is inserted in to the sample fluid 103. This motion is controlled by an automatable controller 110, which moves supports 106 and 107 either together or separately, depending on the process step involved. As shown in FIG. 1A, the controller 110 inserts the sleeve covered wires into the sample fluid 103 and then carries out a predetermined robotized sweeping in order to contact the cells 104 and allow them to gently become attached to the sleeves 108. Then, as shown in FIG. 1B, the cells 104, bound to the sleeves 108, are removed from the sample fluid. Next, as shown in FIG. 1C, the cells bound to the sleeves are inserted into a wash or recovery fluid 114, and as shown in Figure D, the wires 106a are retracted from the sleeves 108 by an upward movement relative thereto, controlled by robotic controller 110.

The device of FIG. 1 (termed the "Magbrush") was constructed from wires attached to a permanent strong magnet. The sleeves were 0.5 mm thick polypropylene plastic. Cells were labeled with EpCAM antibodies and magnetic nanoparticles from Stem Cell Technologies using the EasySep Human EpCam Positive Selection Kit following manufacturer's directions. The breast cancer cell line MCF7 and the promyelocytic leukemic cell line HL60 used in the experiments were purchased from ATCC. EpCAM/nanoparticle labeled MCF7 cells and HL60 cells were mixed in various numbers and then used the MagBrush to capture the epithelial cells. We mixed several thousand HL60 cells with either 1200, 100 or 50 MCF7 cells.

Figure 2A:
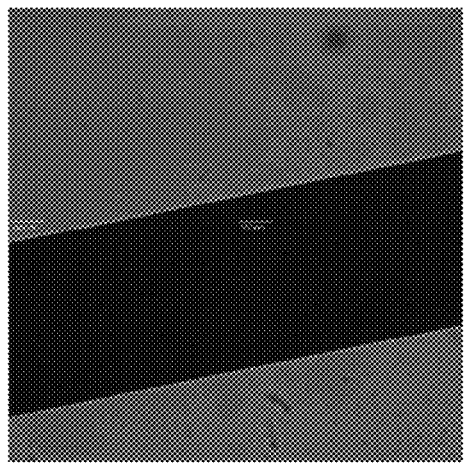
FIG. 2A-D is a series of four photographs showing a device without a sleeve (2A) after the wire has been inserted into a cell containing medium and allowed to incubate and then removed (2B), cell capture with a sleeve-covered wire (2C) and a wire removed from a sleeve (2D), showing that the cells have fallen off; the white size bar in FIGS. 2A and 2B is 100 microns (μM)
Figure 2B:
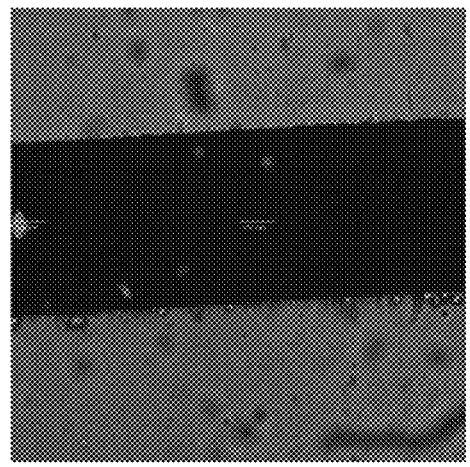

For testing, the known tumor cell line MCF7 cells, with labeled EpCAM beads, were used first. A well of a 96 well plate was filled with 250 µl of buffered saline and a known number of MCF7 breast cancer cells labeled with the magnetic nano-particles were added to the well. A single wire prototype MagBrush without plastic sleeves (FIG. 2A, showing a detail of the wire) was then inserted into the well and allowed to incubate for 15 minutes before it was removed (FIG. 2B, showing cells attached to the wire). For a high starting number of cells (1,200) 93% of the cells were cleared, for the medium cell number (100) 96% of the cells were cleared, and when starting with 50 cells, all of the cells from the well were cleared.

Figure 2C:
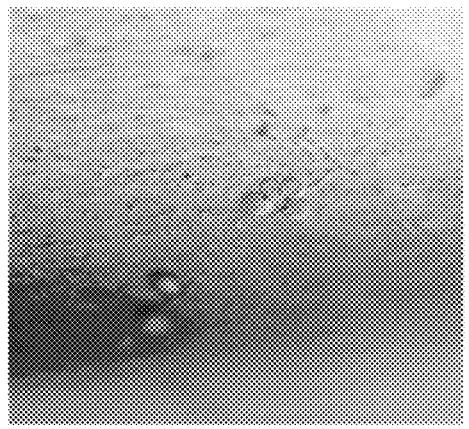
Figure 2D:
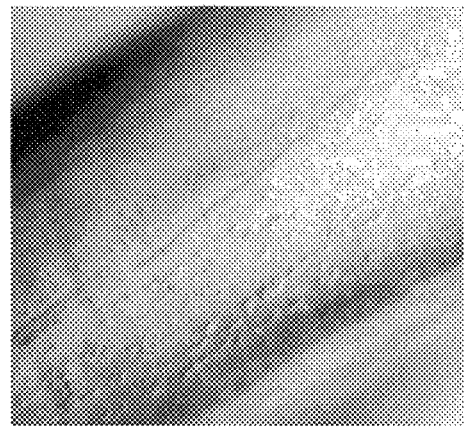

Because the wire was permanently magnetized, it was not found possible to release the cells from this experiment. The MagBrush was fitted with the PVC sleeves and capture and release experiments were repeated. Capture of the cells was done with the same efficiency as in the above experiment (FIG. 2C, showing a wire in a sleeve), but by removing the wire from the sleeve, the cells would fall off the plastic sleeve with ease (FIG. 2D, showing the sleeve without cells).

Finally, cellular isolation was done with sleeve coated wires with a mixture of MCF7 and HL60 cells. The HL60 cells do not express the EpCAM surface antigen. It was again possible to isolate similar percentages of the MCF7 cells, but also, inadvertently, some of the HL60 cells were captured. To rectify this contamination, multiple rounds of capture and release were used and allowed for a pure isolation of the MCF7 cells. After capturing the MCF7 cells with the MagBrush, the cells were released into a tissue culture dish with growth media and allowed to grow for several days. The cells were able to attach and grow, showing that viability was not affected by the labeling, capture and release protocol.

Thus it can be seen that the MagBrush isolates purified and living epithelial cells with high efficiency from a mixture of epithelial and non-epithelial cells. This device has the ability to purify living CTCs from whole blood and should facilitate subsequent biological analysis. In addition, this high-throughput assay should result in a faster and less costly isolation of CTCs than current methods.

III. Permanent Magnetic Rod Embodiment ("MagSweeper")

Figure 7A:
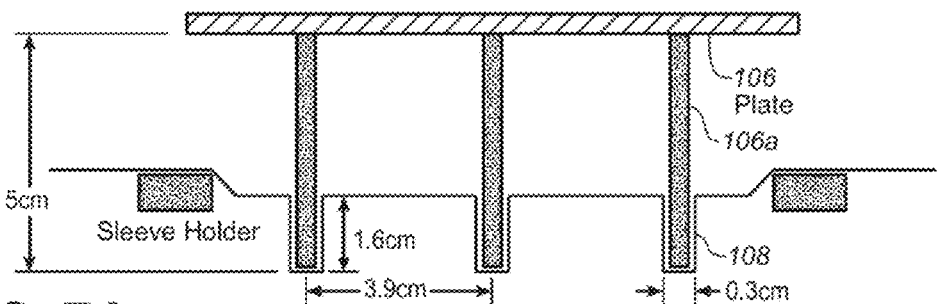
FIGS. 7A and B comprise drawing showing the design of an embodiment of the present device using magnetic rods and a plastic sleeve, where there are six rods and six sleeves, and the sleeves are collectively joined to a sleeve holder, as shown in side view, FIG. 7A. As seen in top view (FIG. 7B), the sleeves and rods are arrayed so that each can be manipulated and placed into a different sample container.
Figure 7B:
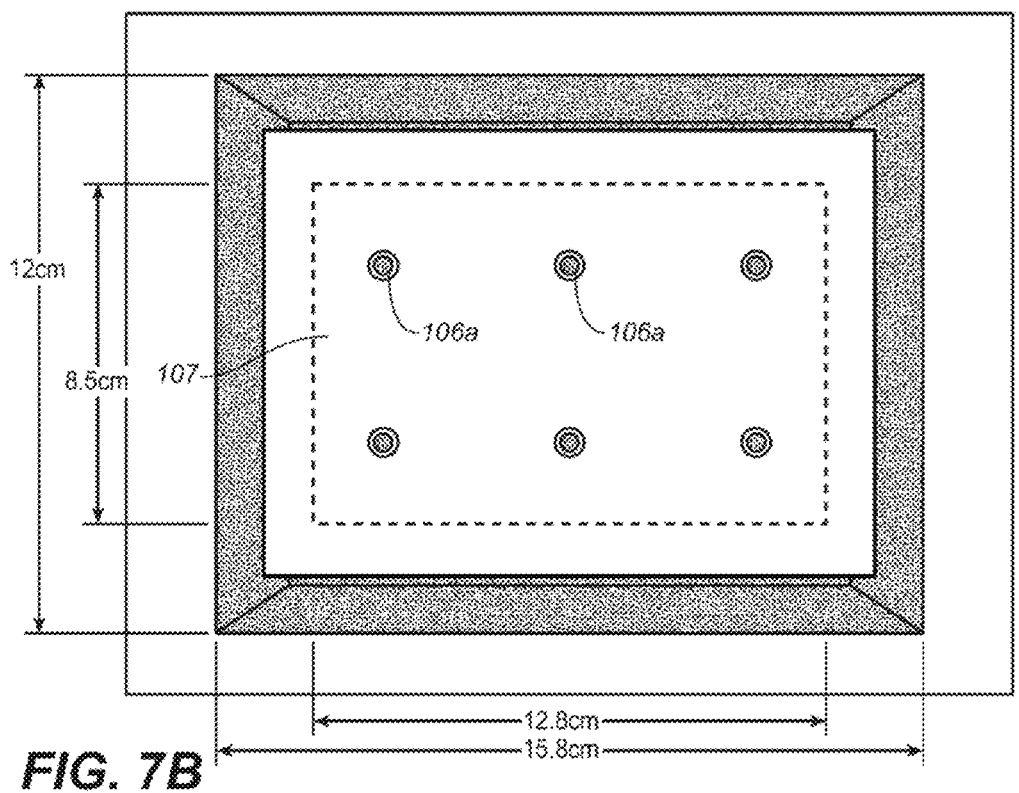

This embodiment uses a powerful permanent magnetic rod illustrated in FIG. 3, as well as in FIGS. 7-9. The rod has a substantial diameter, as opposed to a wire, and is magnetized longitudinally to form a dipole with one end where the beads are shown as attaching to the bottom of the rod. The magnet has a very high pull force (e.g., ~0.99 lbs) and may be on the order of ⅛ inch in diameter. The preferred magnetic rod is a rare earth magnet. Neodymium magnets are a member of the Rare Earth magnet family and are the most powerful permanent magnets in the world. They are also referred to as NdFeB magnets, or NIB, because they are composed mainly of Neodymium (Nd), Iron (Fe) and Boron (B). The magnets used in the exemplified device were obtained from K&J Magnets, as model D2X0, with the following specifications: Dimensions: ⅛" dia.×1" thick; Tolerances: ±0.001"×±0.002"; Material: NdFeB, Grade N42; Plating/Coating: Ni—Cu—Ni (Nickel); Magnetization Direction: Axial (Poles on Flat Ends); Weight: 0.0532 oz. (1.51 g); Pull Force: 0.99 lbs; Surface Field: 4175 Gauss; Brmax: 13,200 Gauss; BHmax: 42 MGOe.

Figure 3A:
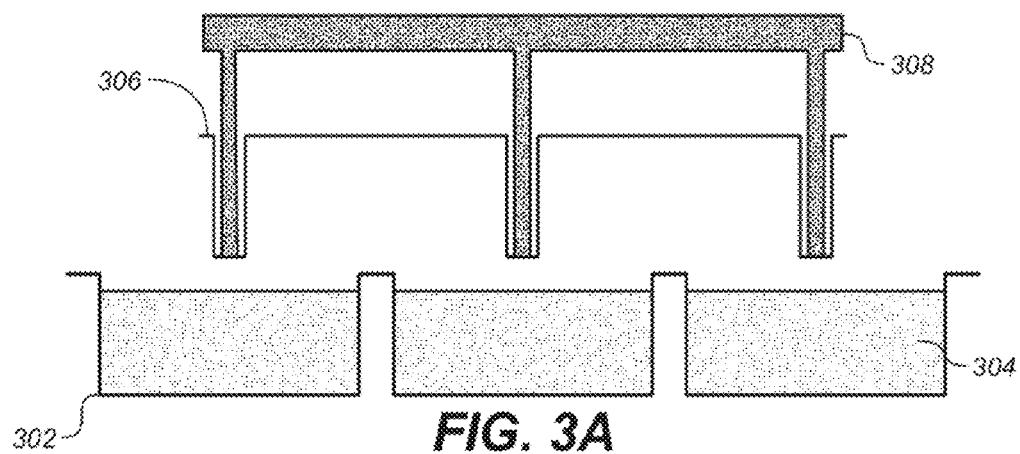
FIG. 3A-F is a series of six drawings which illustrate a schematic representation of one embodiment of a device according to the present invention.
Figure 3B:
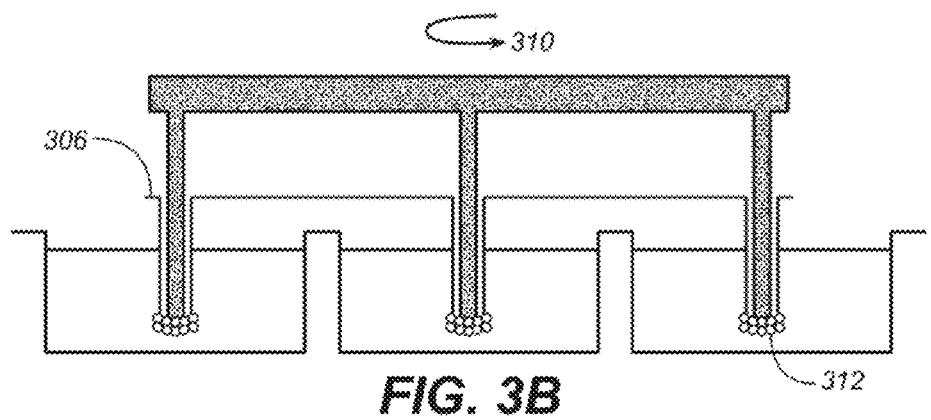
Figure 3C:
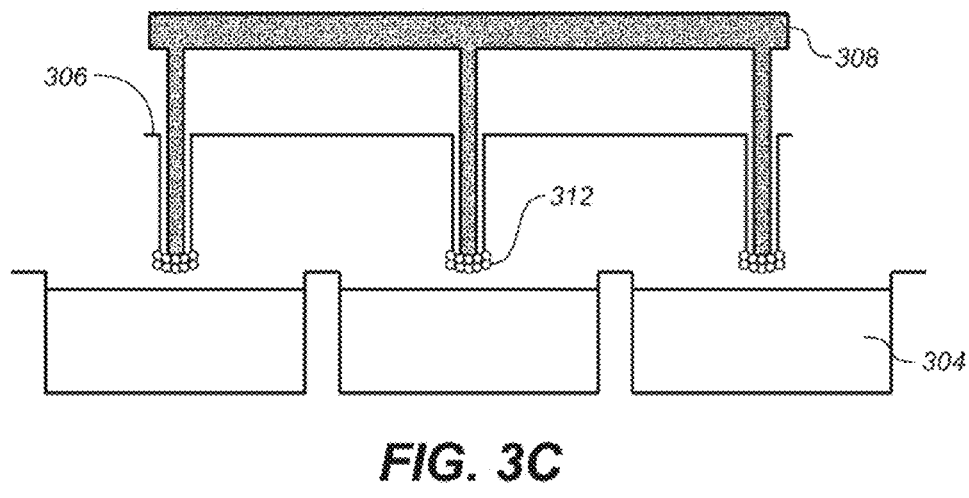
Figure 3D:
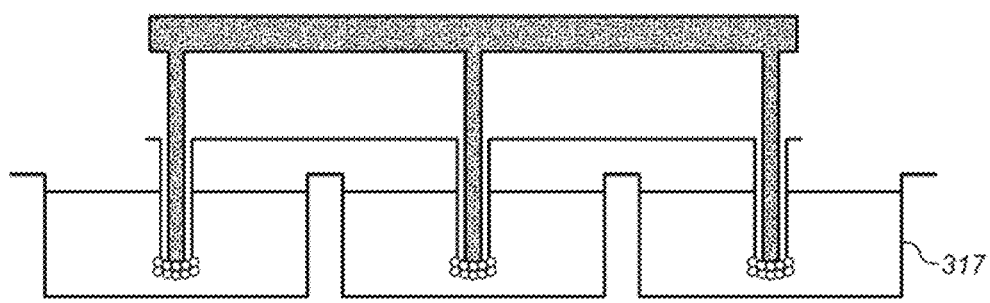
Figure 3E:
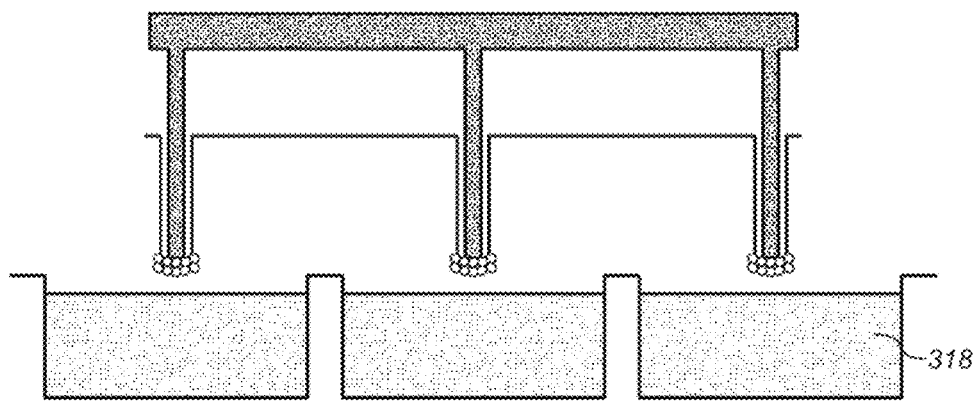
Figure 3F:
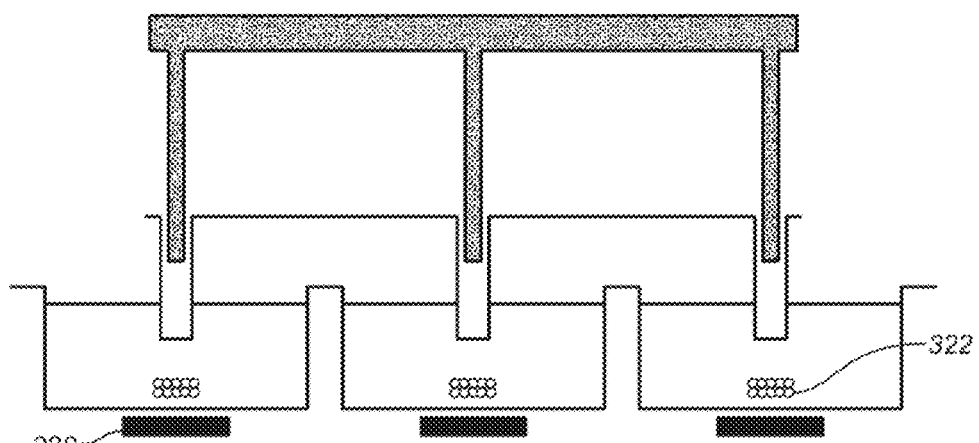
Figure 4A:
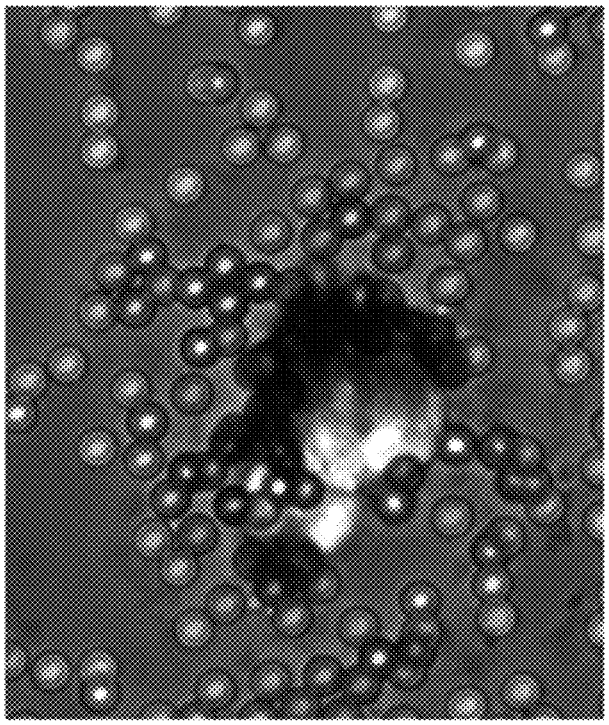
FIGS. 4A and 4B are photographs showing 40× magnification of MCF7 cells (expressing GFP) added to donor blood, labeled with Dynabeads® and captured with the device.
Figure 4B:
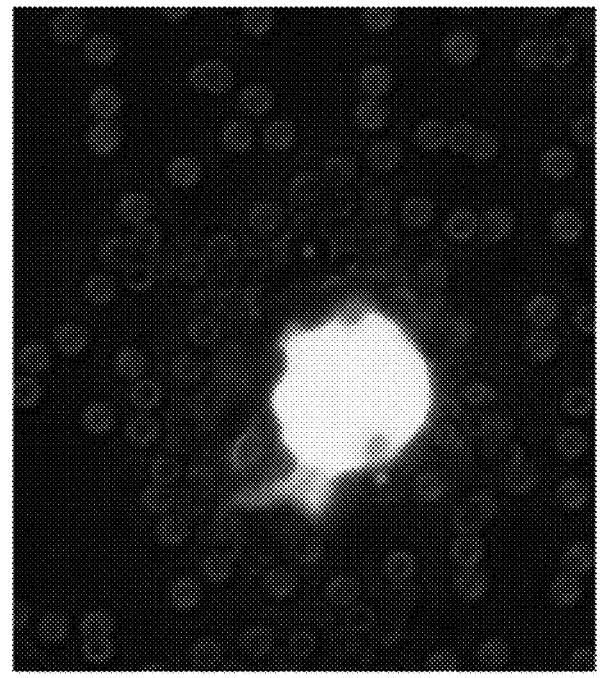
Figure 5A:
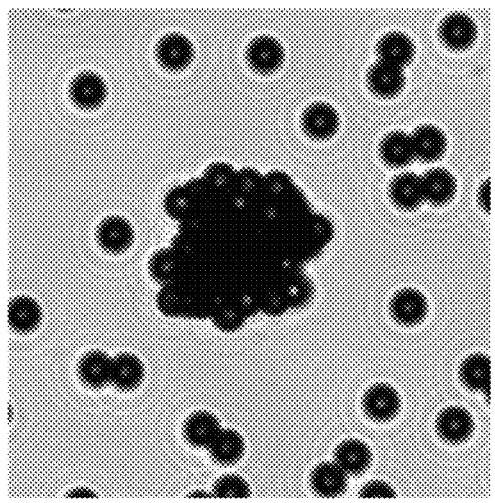
FIG. 5A-C are photographs showing 40× magnification of a selection of CTCs, labeled with Dynabead® beads and isolated using the device, the CTCs being from two patients (SM014 and SUBL018).
Figure 5B:
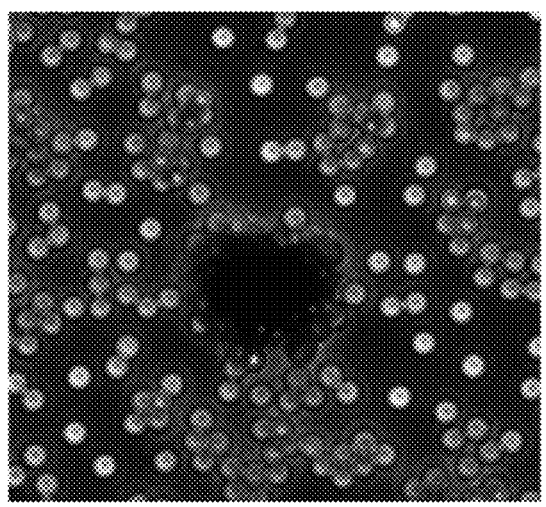
Figure 5C:
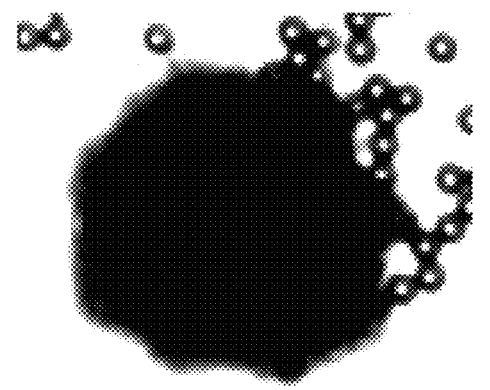
Figure 6A:
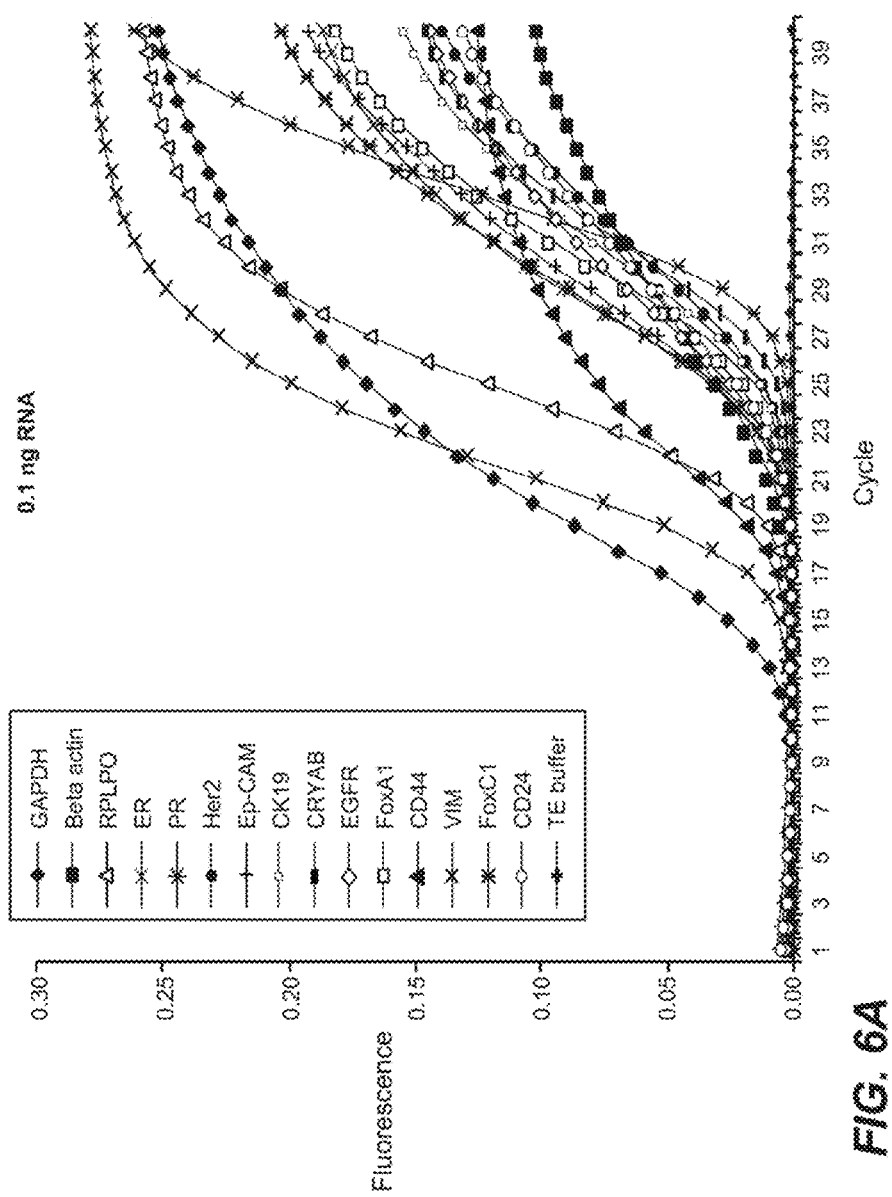
FIG. 6A-E is a series of five graphs showing amplification plots showing the integrity of cells isolated with the present device, with 15 different genes as indicated, in samples containing (FIG. 6A), 0.1 ng of human reference RNA.
Figure 6B:
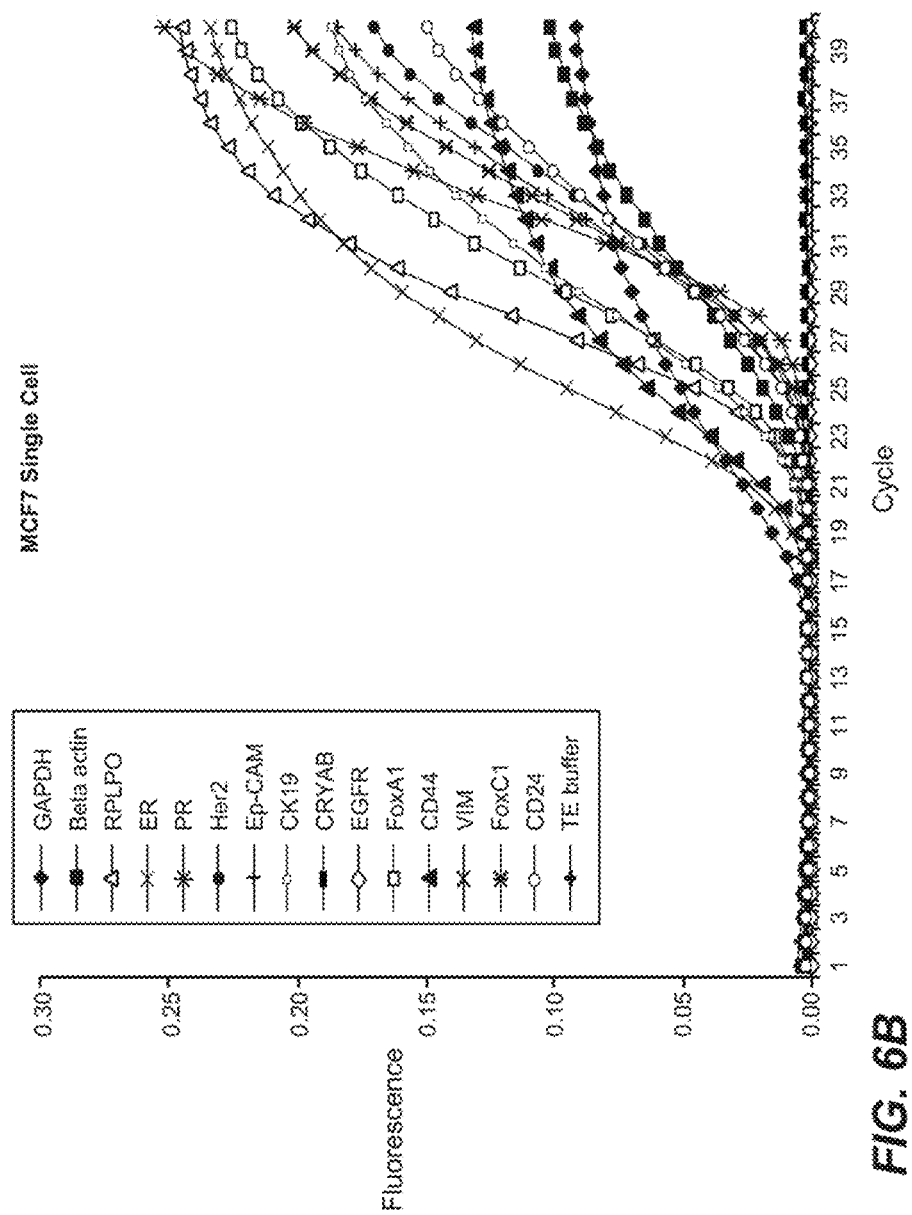
Figure 6C:
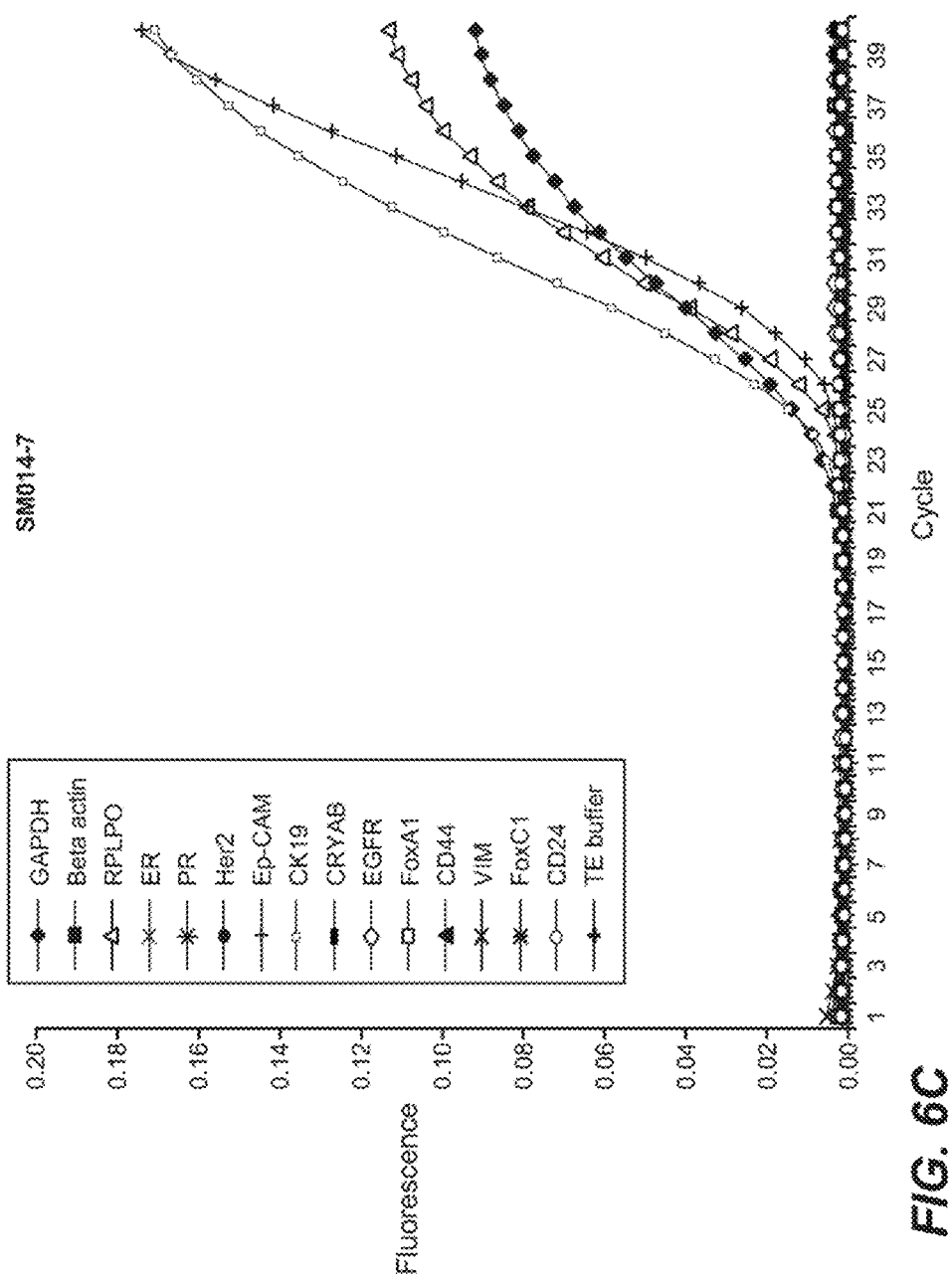
Figure 6D:
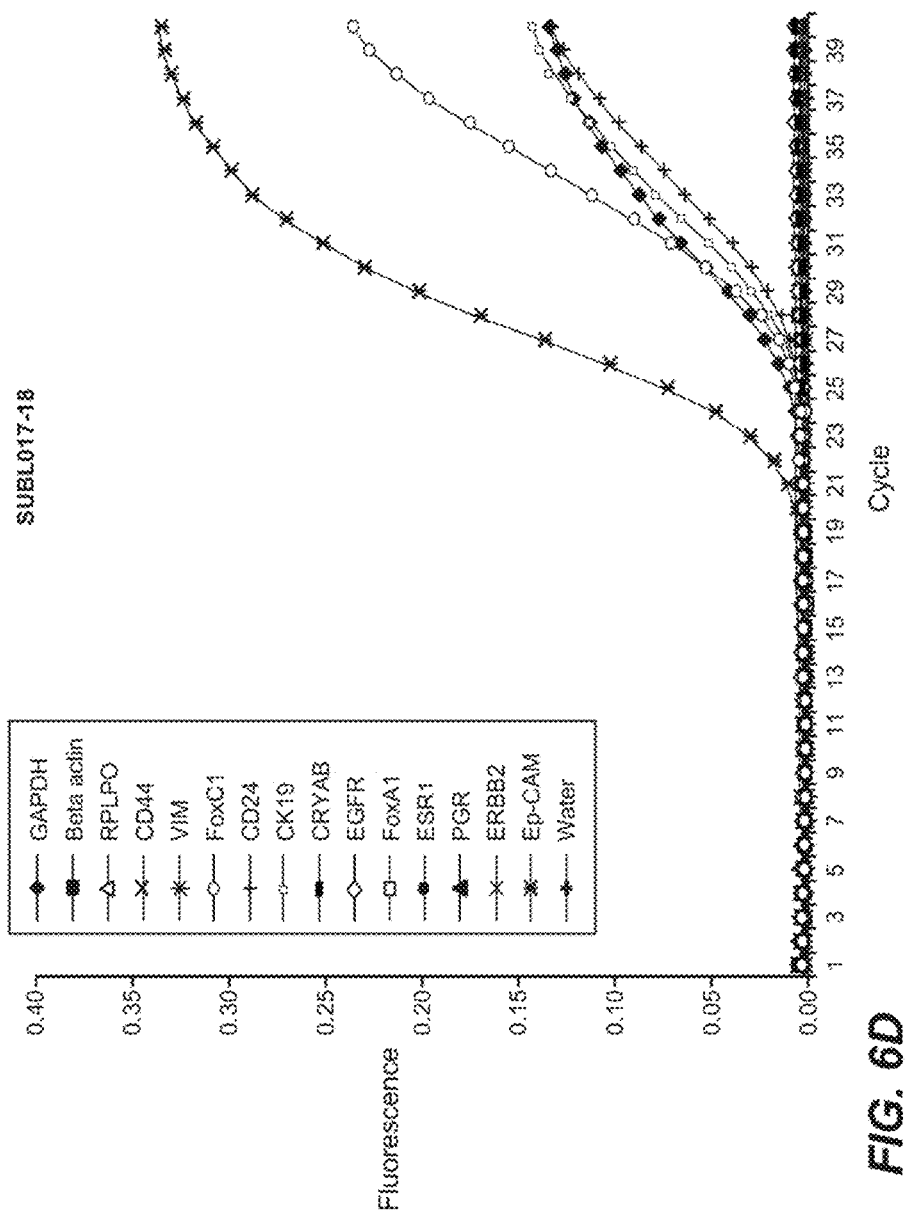
Figure 6E:
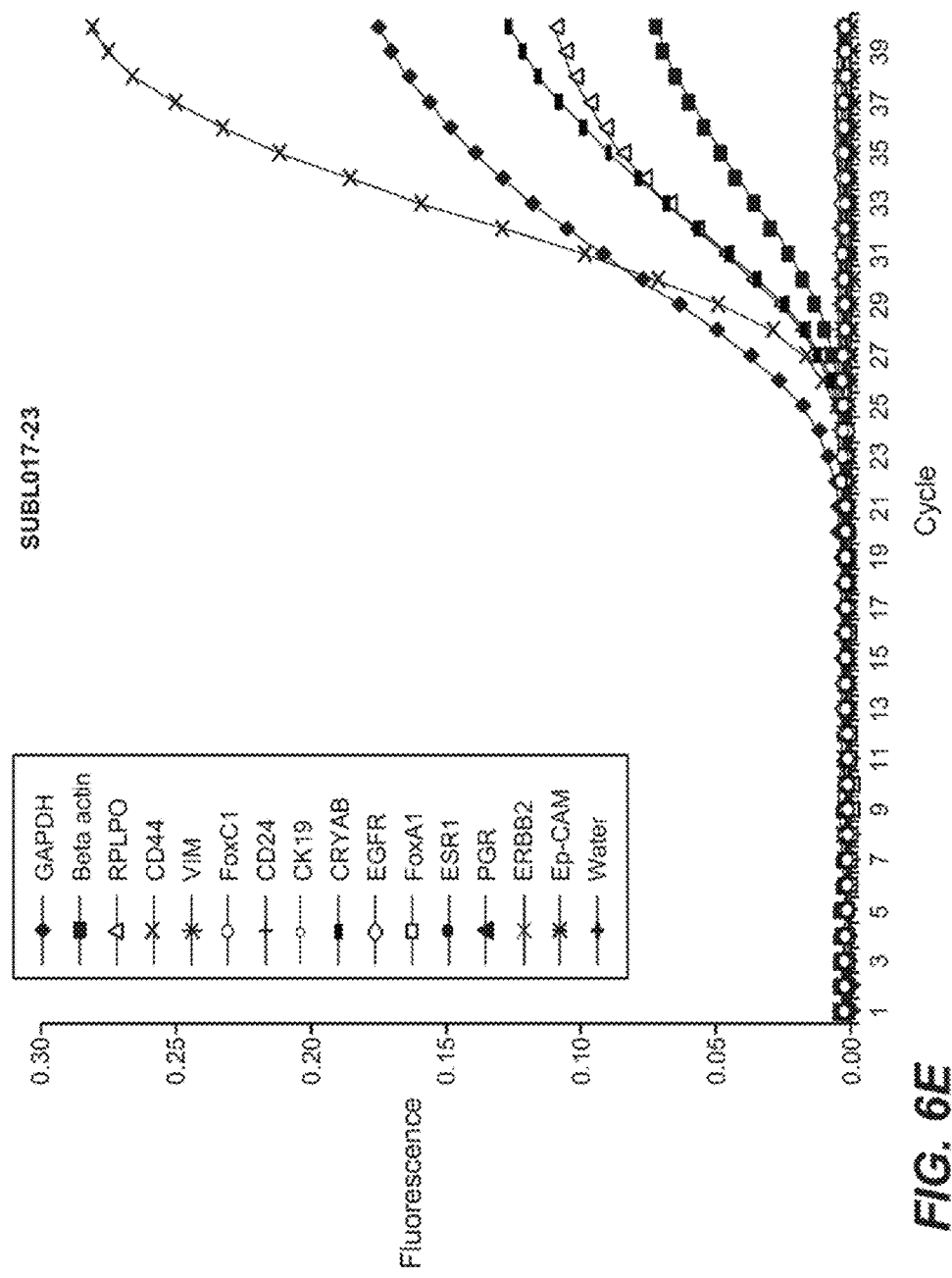

Referring now to FIG. 3A-F, there is shown a device operating in principle as the device in FIG. 1. The illustrated device is made up of three NdFeB magnetic rods. The rods are covered with a removable plastic sleeve that is designed to fit tightly over the rods (FIG. 3A). For cell capture, the rods are engaged into the plastic sleeves and then moved through a blood sample treated with Dynabead® superparamagnetic, monosized polymer particles (FIG. 3B). The rod/sleeve assembly is then rinsed in PBS several times then moved (FIG. 3C) into a fresh well where the cell containing rods are immersed (FIG. 3D). The cell-bearing rods are moved to another container for receiving the cells (FIG. 3E), then magnets are removed from the sleeves and a magnet is placed under the sleeves to facilitate removal of labeled cells from the now nonmagnetic sleeves (FIG. 3F). Attachment and removal of labeled cells can be seen at the bottom of FIG. 3F.

Three containers 304 each receive a single magnetic member. The three magnets are constructed in a magnet array 308, where each magnetic rod can be removably enclosed within a sleeve 306 which is between the magnetic member and the sample and contacts the sample. As shown in FIG. 3B, the sleeved magnets are swirled through the sample, and magnetically responsive cells adhere to the magnets (through the sleeves), as shown at 312. Although the cells are shown as being concentrated near the distal tip of the rod, the cell attachment will vary depending on the design of the magnet (See FIG. 8). Once the cells have attached to the plastic sleeve, the assembly is removed from the container containing the cells to be captured, as shown at FIG. 3C. As shown at FIG. 3D, the assembly is next moved into a wash container having a buffer 317 for removing any contaminating cells which may have nonspecifically bound to the sleeve. This step may be repeated as needed. Then, as shown in FIG. 3E, the assembly is moved to another solution 318 into which the cells may be released and captured. As shown in FIG. 3F, the magnets 306 are removed from the sleeves 306, and release of the cells is assisted by magnets 320 on the bottom of the wells, causing the cells bearing magnetically responsive labels to be drawn to an area 322 adjacent the magnets 320.

In order to obtain a magnet design that has extremely high capture ability in the design utilized, a series of experiments were conducted, as illustrated in FIG. 8. Different magnet configurations are shown at FIG. 8A through FIG. 8F, showing a single rod in each figure with variations in axial segmentation and diameters below the magnet support. In order to test different magnet configurations, a mixture was prepared with ~10,000 MCF7 cells in 2 ml of DMEM which was treated with 80 µl of EpCAM for 15 minutes, 80 µl of nanoparticles for 15 minutes, and 15 minutes in robosep magnet. Supernatant was removed and labeled cells were resuspended in 1 ml DMEM. Count (7.5 cells/µl). 10 µl of cells was added to 2.5 ml of DMEM into each of 12 wells of a 24 well plate. The cells were swept with the robot then the procedure was to spin down plate at 800 rpm for 5 minutes and then count cells in the wells. Then the designs in FIG. 8 A-F were tested as follows:

a) Two wells got no magnets—51, 32
b) Two wells got nonmagnetized 5.1 mm cylinder—13, 7
c) Two wells got 3 mm (⅛ inch) cylinders—1, 2
d) Two wells got 1.5 mm (1/16 inch) cylinders—9, 22
e) Two wells got 3/16" ring magnets wrapped in parafilm—0, 0
f) Two wells got 3/16" ring magnets—1, 0.

The use of a single long magnet, with a longitudinal dipole (FIG. 8D), was found here to give superior results.

In order to demonstrate the ability of the present device to separate tumor cells from blood, a known number of MCF7 cells stably transfected with pAcGFP1-N1 from Clontech were added to 9 ml of normal donor blood (GFP labeling was done for easier epithelial cell identification). 10 ml of CEL-Lection Epithelial Enrich Dynabeads were added and incubated for 30 minutes at room temp with constant mixing. The device was then utilized to isolate and purify the cells. Blood samples were collected from female patients with metastatic breast cancer in compliance with all regulations regarding Human Subjects. 9 ml of blood from each patient was collected, labeled with Dynabeads, isolated with the Device as above. Single CTCs were manually selected for multiplex real-time qRT-PCR. For qRT-PCR, the single cells were pre-amplified for 15 targets with qRT-PCR kit from Invitrogen. Each of the pre-amplified products was diluted and applied to qRT-PCR reactions for each individual target listed below. We used TaqMan primers and probes from Applied Biosystems. Human reference RNA and TE buffer were used as controls.

Referring now to FIGS. 7A and B, which is a drawing corresponding to an as constructed prototype, there is illustrated a support plate 106 which is attached to and holds three magnetic rods 106a, which extend downwardly through a sleeve array, and a sleeve holder which maintains the sleeves in a fixed position relative to withdrawal and insertion of the magnets. The axially or diametrically magnetized rods are attached to a 5-function/3 axis robot. The top view shows the approximate dimensions of the array in a six-rod prototype embodiment. Upon activation of the robot, the magnetic rod is inserted into a plastic sleeve and lowered into a liquid sample (e.g., human blood) that has been previously mixed with magnetic beads attached to antibodies specific for a target biomarker (e.g., cancer cells labeled with immunomagnetic beads). The robotic arm then sweeps the magnetic rod through the liquid to capture the magnetically labeled targets (e.g., cancer cells). The robotic arm lifts the magnetic rod and captured biologics and then moves in a linear direction to the next station, where it lowers into a washing solution. The rod agitates/sweeps within the wash solution, during which time contaminants fall off the magnetic rod. The wash solution may be drained and refilled multiple times to ensure complete removal of contaminants. The robot then moves the magnetic rod to a final release station. Here the magnetic rod is in, but can be lifted out of the plastic sleeve, which still remains in the release fluid. The robot shakes the release fluid and cells or biologics on the plastic sleeve fall into the release fluid for further analysis. Any of the capture, wash, release steps may be repeated for complete capture and purity.

IV. Fluid Flow Embodiment—Stationary Non-Adherent Sleeve

An alternative embodiment utilizes fluid flow, for example in a fluidic channel. For example, the non-adherent sleeves comprising the magnetic members extend into a fluidic channel. The various sample, wash, and release solutions are then flow past the non-adherent sleeves. The magnetic field across the non-adherent sleeves can be applied and removed in order to capture particles from, or release particles into the fluid.

As with the other embodiments described herein, controlling the velocity between the magnetic member and non-adhesive sleeve during capture is important in order to obtain the purities and capture efficiencies described herein. The same ranged of velocity and Reynolds number described above are relevant to this embodiment as well. As above, it is desired to have fluid flow rates around the magnetic member that are in the non-turbulent flow regime.

Figure 15:
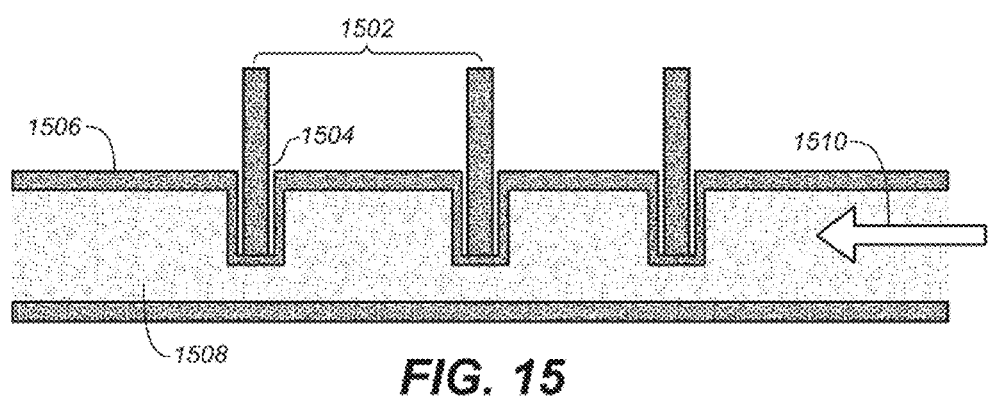
FIG. 15 is a schematic drawing showing an exemplary embodiment of the invention comprising a fluidic channel.

FIG. 15 shows an example of this embodiment. Here, magnetic members 1502 extend into a fluidic channel 1506 containing a liquid sample of cells 1508 within the channel, which can flow in a direction indicated by arrow 1510. The magnetic members 1502 are surrounded by a non-adherent sleeve 1504, which can be formed within the fluidic channel 1506, where the magnetic members would contact the solution 1508 due to their impingement into the channel, but for the sleeve 1504. The magnetic field from the magnetic member across the non-adherent sleeve can be applied and removed for capture and release. In some embodiments, the magnetic members are stationary throughout the process, and the magnetic member is magnetized and de-magnetized, for example using one or more electromagnets. In other embodiments, the magnetic member is inserted into the non-adherent sleeve to apply the magnetic field, then pulled out at least partially so as to substantially remove the field across the non-adherent sleeve. The embodiment in FIG. 15 shows 3 magnetic members, but any effective number of magnetic members can be used. In some cases one magnetic member can be used, in other cases numbers up to 10, 100 or more can be used.

Figure 16A:
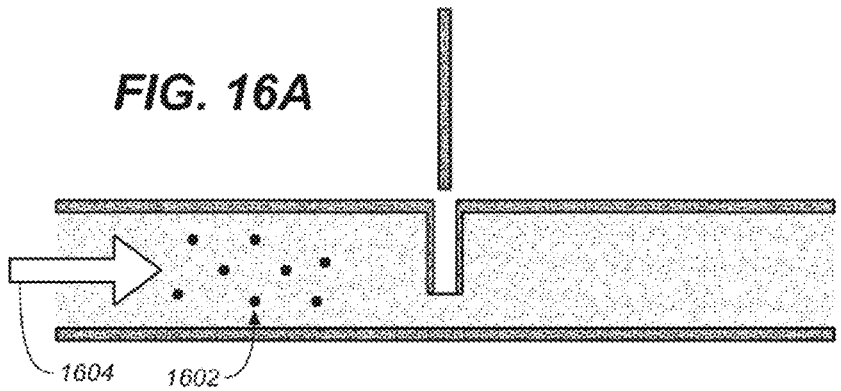
FIG. 16A-D is a schematic drawing showing an alternative exemplary embodiment of the invention comprising a fluidic channel and a magnetic member that can be inserted or removed from a hollow pillar; (A) shows cells prior to attachment; (B) shows cells attached to the magnetic, sleeved roof; (C) shows a wash step with cells attached; and (D) shows release.
Figure 16B:
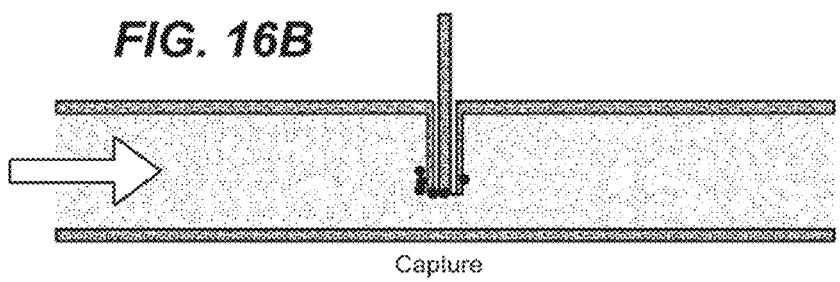
Figure 16C:
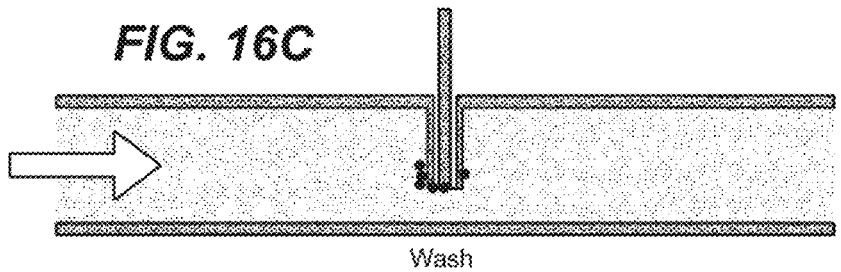
Figure 16D:
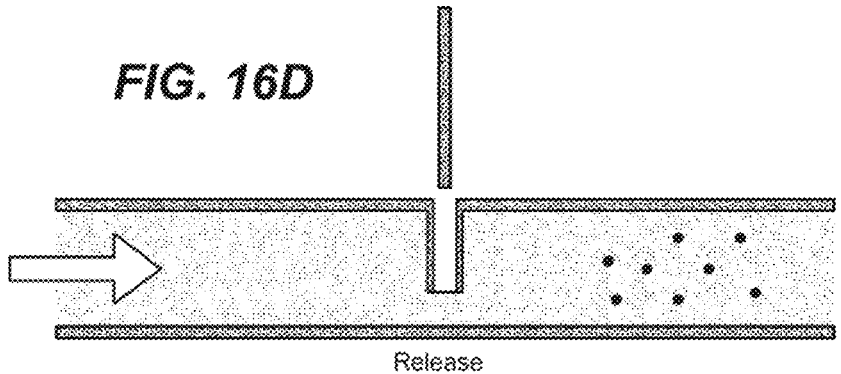
Figure 17A:
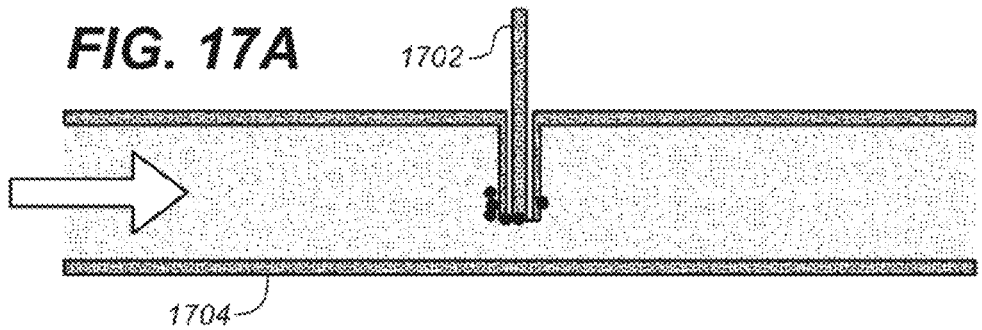
FIG. 17A-C is a schematic drawing illustrating assisted release with a high flow rate and assisted release with an external magnet in an embodiment comprising a fluidic channel; (A) shows wash step; (B) shows assisted release; and (C) shows assisted release with external magnet.

In some embodiments, the apparatus comprises a fluidic channel containing a hollow pillar or an array of hollow pillars, in which an external magnet engages or withdraws in each pillar (see FIG. 16(A) through (D)). By engaging magnets inside hollow pillars, magnetically labeled cells 1602 will be attracted and attached to pillars resulting in capture (FIG. 16B). By withdrawing the magnets from the pillars, the labeled cells will detach from the pillars and get released to the bulk solution in the channel (FIG. 16D). In some cases a wash step can also be used by passing wash solution while the magnetic member is engaged (FIG. 16C). To facilitate the target cell removal from the pillars, an external magnet can be placed under the fluidic channel and/or the fluidic flow can be adjusted (FIG. 17). In some embodiments, each channel can contain one or an array of hollow pillars (FIG. 16). Magnetized pillars can go freely travel inside and outside these pillars for capturing and releasing the targeted cells labeled with functionalized magnetic beads. When the magnetized pillar enters the hollow pillar in the fluidic channel, the labeled cells will attach to the pillar surface (FIG. 16B). After washing the fluidic channel with a wash buffer (FIG. 16C), the magnets will disengage from the hollow pillars to release the captured cells (FIG. 16D). In some cases, the released cells go through rounds of capture-wash-release to increase the purity of target cells. The fluid flows in the direction of arrow 1604, and it can be seen that the released cells flow downstream. The embodiments of FIG. 16-18 further contemplate additional fluid compartments to deliver and receive the fluid. The fluid may further be continuously circulated or washed back in forth in a reciprocal manner. This provides multiple sample contact and wash steps. The sample fluid may be contained in compressible chambers, for example, at either end of the illustrated tube for receiving and expelling fluid under control e.g. of mechanical plungers or rollers, which operate in a continuous manner or according to other preprogrammed sequences.

Figure 17B:
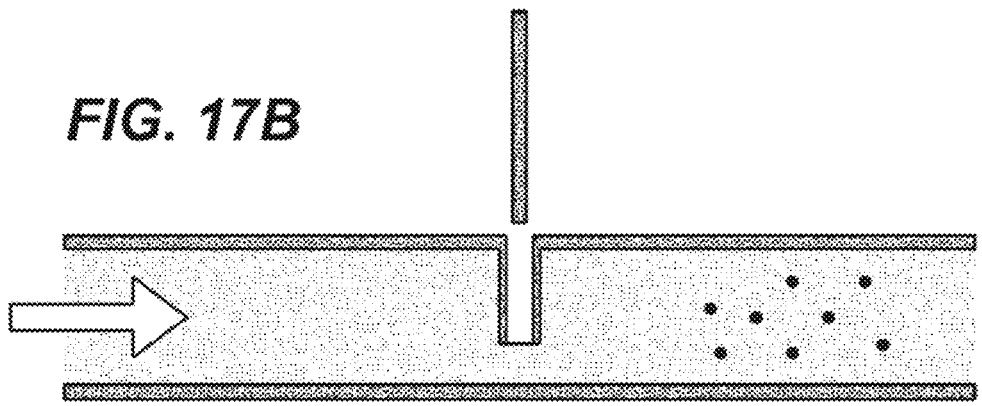
Figure 17C:
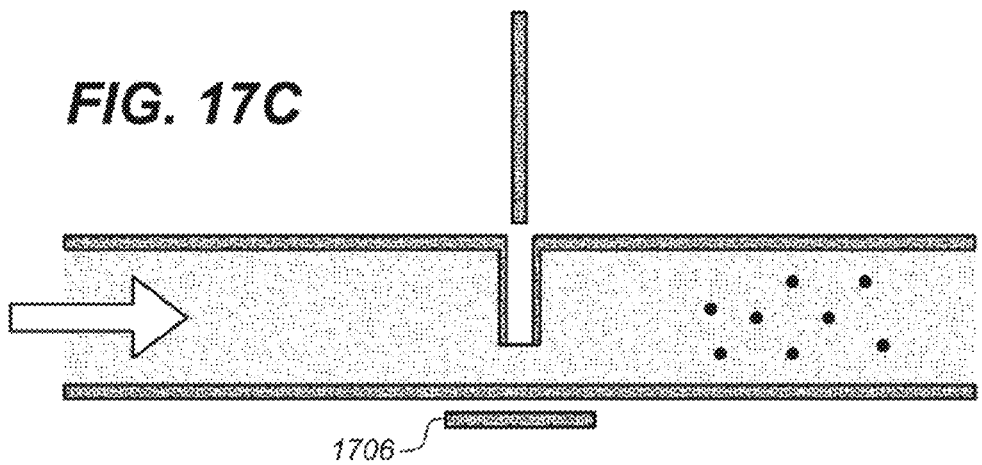

FIG. 17 shows the magnetic member 1702 in a fluid channel 1704 similar to similar to FIGS. 15 and 16. To assist the release of target cells, the flow rate of the fluid can be increased (FIG. 17B) or an external magnet 1706 can be placed underneath the fluidic channel (FIG. 17C) and underneath the magnetic member. This external magnet can be a permanent magnet which can be mechanically placed and removed from underneath the channel or it can be an electromagnet which can be turned on and off electrically.

In one alternative embodiment, shown in FIG. 18, the fluidic channel 1802 comprises a thin and elastic wall. When the magnet 1806 is pushed toward and into the fluidic channel, the fluidic wall will also deform and form a hollow pillar around the magnet, contacting the solution 1804.

V. Procedures

General Procedures and Robot Control

As described in detail below, the present methods involve first obtaining a sample containing cells or other structures to be isolated (target cells), such as the isolation of tumor cells (which are rare, i.e., 1 in 100-10,000 blood cells in peripheral blood). The blood sample is exposed to a reagent which labels only the target cells. The antibodies are attached to a magnetically responsive particle, such as by biotinylating the antibody and binding it to a streptavidin-coated bead. A preferred reagent is an antibody that recognizes tumor cells. The tumor cells will be of a different phenotype than the blood cells, such as epithelial cells, as are a typical breast cancer cell type. Other tumors may be of endothelial or connective origin and may be distinguished on that basis. Other labels may be based on tumor or cell subtype, such as markers for stem cells, or certain tumor phenotypes, such as EGF+ or Her2+, etc. The labels are attached to a magnetic particle and thoroughly mixed in the blood sample. Then the magnetic members, encased in inert nonmagnetic sleeves which permit the magnetic force to pass through, and, further, do not absorb or adhere to the blood cells or target cells, are contacted with the blood sample. The sleeved members are thoroughly exposed to the blood sample so as to not destroy cells, but come into close contact with any rare cells present.

In some cases, when running the capture protocol, the magnets are approximately 1-2 mm from the bottom of the plate in the container holding the blood sample. The sleeves coating the magnetic members are made, for example, of PVC are fitted very tightly to the magnets. The thickness of plastic sleeves are in the range of 0.001-0.01" (25 micron-254 micron). During the capture phase (see FIGS. 1A and 3B), a robotic arm attached to an actuator capable of movement in three directions (xyz actuator) sweeps through each sample container in a predefined, reproducible pattern. A robotic arm moves at 2 mm/second, it makes 12 loops, and each loop has a radius offset of 1 mm from the prior loop. Next, as shown in FIG. 1B and FIGS. 3C and 3D, the magnetic members are moved into a different solution for washing. This is preferably accomplished by moving the robot, but the sample holder may also be moved. The arms are immersed in a completely different liquid to wash off non-target cells that have become entrained in the bead-decorated cells or non-target cells that have non-specifically bound to the inert sleeve that covers the magnets. For washing, the robotic arm preferably moves, e.g., at 2 mm/second, over a loop radius of 5 mm and goes for 30 seconds. Washing is preferably carried out several times by changing the solution in the second container. Next, after washing, the target cells, with magnetic beads attached, are released into a third container as a purified population. This is shown in FIGS. 1C and 1D and FIGS. 3E and 3F. The cells are typically placed into a capture buffer in a third container, which has magnets at the bottom to help draw the magnetic beads off of the inert sleeves. At this stage, the magnet is removed from the sleeve so that the beads are no longer drawn to the sleeves and will fall off. At release, there is no arm movement. The sleeve covered magnet enters the liquid, the magnets are withdrawn and there is a strong magnet (the exemplified magnet is a neodymium rod magnet, e.g., as made by K&J Magnetics, Jamison, Pa.) underneath the plate that pulls the cells/beads off the sleeves to the bottom of the plate.

As can be seen from the above description, the entire process can be automated by computer control, once the blood has been labeled by antibodies specific to the cells to be removed, preferably CTLs.

Exemplary Procedure for Obtaining Rare Cells from Human Blood

As an exemplary protocol for obtaining rare cells from human whole blood, blood was collected in 10 ml EDTA vials (BD#366643). About 9 ml per each vial was actually obtained. Blood is then taken to the lab and the blood is split into three (3) new vials and each is brought up to 6 ml total with PBS pH7.2. Next 3.4 ul of Dynabeads, Cellection Epithelial Enrich (4.5 um diameter superparamagnetic polystyrene beads coated with monoclonal mouse IgG1 antibody Ber-EP4 [aka EpCAM]) are added to each sample. The samples are then mixed for 30 minutes at room temperature, while being rotated (10 rotations/minute). Samples are then placed into wells of a 6-well plate (Falcon 353502) and the tubes are rinsed with PBS to bring each sample up to 10 ml. The robot is then run as follows:

Two capture cycles, two wash cycles, one release cycle. The plate containing the released cells in then placed in the capture position and one round of capture is run. This recapture is how we reduce/avoid contamination by blood cells.

The samples are then washed twice (that is repeating steps shown in FIGS. 3C and 3D a multiple number of times) and then released into 500 ul tubes containing 360 ul of media (300 ul DMEM with 10% fetal bovine serum, 30 ul of DNase1, 30 ul of 25 mM magnesium chloride). This removes some of the beads, but mostly it just keeps beads from sticking together, which minimizes clumps so that the cells are easier to see.

Samples are then incubated for 10 minutes at room temperature and then the samples are transferred to a 6-well plate, where cells are hand selected (picked up using a micropipet). Each cell is collected in a volume of 2 ul and with 0.2 ul of RNase inhibitor (Superase IN, from Ambion, product #2694) added. Samples a then frozen on dry ice until the qRT-PCR is run.

TABLE 2

Examples of MCF7 cells spiked into normal donor blood, labeled with Dynabeads and captured using the Device.

| Cells Added | Cells Isolated |
| --- | --- |
| 41 | 8 |
| 50 | 10 |
| 40 | 8 |
| 24 | 13 |
| 16 | 7 |
| 19 | 5 |

Isolation of Breast Cancer Tumor Cells from Patient Blood and Analysis of Those Cells by rt-PCR Two patient samples are described. From the first patient (ID# SM014), one vial of blood was obtained. From this patient, 10 potential cells, were isolated, but only one of which had RNA of good enough quality to get data from the qRT-PCR. For the second patient, (ID#SUBL017), three vials of blood were received, and isolated 26 potential cells were isolated, of which 25 showed RNA.

Cells have since been isolated from 4 additional patients (82 potential cells) and from the blood of mice that were growing tumors derived from a human breast cancer cell line (MDA-MD-231). From the mice, 16 cell samples were subjected to qRT-PCR analysis and several hundred more cells were grown in culture.

Pre-Amplification for Multiple Targets

1. Samples were pre-amplified with the CellsDirect™ q RT-PCR kit (Invitrogen, catalog Number 11754-100). For Multiplex qRT-PCR, each assay employed a TaqMan assay from Applied Biosystems. The 20× assays for the targets were diluted in TE buffer to make 1× Assay Mix and used in the pre-amplification step.

The sample RT-Pre-Amp Master Mix was prepared by combining the following steps and components:

| Component | Volume* (µL) |
| --- | --- |
| CellsDirect 2X Reaction Mix | 5.0 |
| 1x Assay Mix | 0.5 |
| RT/Taq Enzyme | 1 |
| Cells in TE buffer | 3.5 |
| Total | 10 |

Note:
If the cells are to be stored after sorting or, if the RNase activity is suspect, add 0.1 µL of Ambion's SUPERase-In 2. Perform Thermocycling.
   a. Reverses transcribe the RNA to cDNA at 50° C. for 15 minutes.
   b. Inactivate the RT enzyme and start the Taq by bringing the sample to 95° C. for 2 minutes.
   c. Preamplify the cDNA by denaturing for 18 cycles at 95° C. for 15 seconds each, and annealing at 60° C. for 4 minutes.
   d. Dilute the resulting cDNA product 1:2 with water or TE buffer.

Application of the Preamplified Sample on Fluidigm Biomark™ 48.48 Dynamic Array Chip This was done for multiple qRT-PCR reactions based on the manufacture instructions. This chip is commercially available and is described further on the Fluidigm web site. It carries out TaqMan® PCR assays in a matrix of channels and valves on a microfluidic chip. 48 samples and 48 assays can be loaded into the inlets of the chip's input frame. This permitted analysis of single cells, which contain picogram quantities of RNA, insufficient for reproducible microarray analysis. The chip uses integrated fluidic circuits and pressure-controlled nanovalves to perform highly sensitive parallel qRT-PCR assays based on standard 5'-nuclease probe (TaqMan) chemistry and primer-probe design rules. The rows of these chips are loaded with the reagents (primer pairs plus TaqMan® probe mixtures, for instance) and the columns with cDNA samples generated from cellular RNA and other PCR components that are prepared off chip. The contents of the rows and columns are then mixed with each other automatically in the designed reaction chambers of the chip (10 nl each) without cross-contamination. Therefore the primers and samples can be tested in a combinatoric manner: systematically combined into 2,304 parallel reactions. Performing the same set of reactions by hand or with a robot would require orders of magnitude more reagents and pipetting steps, each of which could introduce the possibility of mistake or cross-contamination. Moreover, the quantity of costly reagents used is much lower than with standard qRT-PCR.

Single cell analysis may be conducted in a number of alternative ways. For example, one could carry out a smaller set of PCR or other amplification reactions; one could culture the single cell to obtain a larger RNA mass; and one could test the single cell with enzymatic or immunological reagents.
Results of qRT-PCR from Tumor Cells Isolated According to the Present Methods The results, obtained from patient samples, and using qRT-PCR described above, are shown in Table 3 below, and in FIG. 6A-E. Table 3 shows relative expression (in percentage) of 15 genes from multiplex real-time qRT-PCR experiments comparing 0.1 ng of human reference RNA (set to 100% expression) to a single MCF7 cultured cell, and a representative sample of isolated circulating tumor cells (CTCs) captured from the blood of two cancer patients (25 single CTCs were individually analyzed in the second patient). Both patients have high-grade infiltrating ductal carcinomas with metastases.

The primary tumor of patient SM014 was ER−/PR−/HER2+. Bone metastases progressed on trastuzumab, and a biopsied bone metastasis was ER−/PR−/HER2−, which matches the expression profile of the CTC SM014 cell 7. Patient SUBL017 had a primary left breast cancer that was ER−/PR+/HER2−, then several years later developed bilateral supraclavicular and mediastinal adenopathy. A right SCLN biopsy was ER+/PR−/HER2−. Two CTCs from this patient, who now has bone metastases, are ER−/PR−/HER2−. All cells were positive for CK19, but showed a wide range of expression levels for the other genes tested.
Measurement of Expression Profiles from CTCs Extracted by a MagSweeper from Eleven Women with Metastatic Breast Cancer plastic composed of polyvinyl chloride (PVC). As described previously, with the magnetic rods engaged inside the plastic sleeve, the labeled cells are attracted to the plastic sleeve; disengaging the rod from its sleeve removes the strong magnetic field gradient and facilitates easy removal of labeled cells. PVC was selected for its lack of nonspecific blood cell binding from among 21 sleeve materials tested.

Magnets used in the MagSweeper were purchased from K&J Magnetics, Inc. (Jamison, Pa.). The sleeved rods were robotically driven to sweep through wells containing blood samples (one rod per well) in a pattern of overlapping concentric circular loops that covered the entire well area. The sleeved magnetic rods sweep through the sample in overlapping concentric circles at 2 mm per second, capturing labeled cells and free magnetic beads, as well as some contaminating blood cells. The sweep velocity was selected for i) cell capture efficiency; ii) application of sufficient shear force to detach adsorbed non-magnetically labeled cells (wash step FIG. 3D); and iii) prevention of damage to the fragile CTCs. It was found experimentally that an optimal circular velocity was around 2 mm/second. After cell capture, the sleeved rods with attached cells move to a new well containing phosphate-buffered saline (PBS). The cells were circularly swept through the wash buffer solution to remove unlabeled blood cells which may be adsorbed to the rods. Finally, the rods and cells were moved to a third wash well containing fresh PBS. The cells were released into the PBS by withdrawing the rods from the sleeves and applying an external magnetic field under the well. Magnetically-labeled cells easily migrate off the plastic sleeve toward the bottom of the well, releasing unlabeled blood cells that may have been trapped between labeled cells and excess magnetic beads. After re-engaging the rods into their plastic sleeves, the labeled cells are then re-captured with many fewer entrapped contaminating blood cells. Sequential rounds of capture-wash-release-recapture significantly improve purity and eliminate all blood cell contamination.

TABLE 3

| Target | 0.1 ng RNA % | MCF7 single cell % | SM014-7 % | SUBL017-18 % | SUBL017-23 % |
|---|---|---|---|---|---|
| GAPDH | 100 | 3.28 | 0.06 | 0.06 | 0.17 |
| Beta Actin | 100 | 21.92 | N/A | N/A | 0.24 |
| Big ribosome protein (RPLPO) | 100 | 21.76 | 0.29 | N/A | 0.9 |
| CRYAB | 100 | N/A | N/A | N/A | N/A |
| EGFR | 100 | N/A | N/A | N/A | N/A |
| FOXA1 | 100 | 271.31 | N/A | N/A | N/A |
| CD44 | 100 | 10.73 | N/A | N/A | 0.61 |
| ESR1 (ER) | 100 | 606.29 | N/A | N/A | N/A |
| PGR (PR) | 100 | 207.05 | N/A | N/A | N/A |
| Vimentin (VIM) | 100 | N/A | N/A | 0.95 | N/A |
| ERBB2 (HER2) | 100 | 72.7 | N/A | N/A | N/A |
| EpCAM | 100 | 14.97 | 3.35 | N/A | N/A |
| FOXC1 | 100 | 8.42 | N/A | 8.36 | N/A |
| CD24 | 100 | 26.79 | N/A | 2.11 | N/A |
| CK19 | 100 | 772.75 | 143.4 | 22.07 | 19.75 |
| TE Buffer | N/A | N/A | N/A | N/A | N/A |

N/A = not amplified.

MagSweeper Parameters

The device used in this example has been described above. More particularly, it utilized powerful neodymium magnetic rods with rounded bottoms. The rods were 6 mm in diameter (50 mm$^2$ capturing area) and a magnetic flux density of 0.5 Tesla at the rod end. The magnetic rods are attached to an actuator to sweep through a blood sample and extract immunomagnetically-labeled tumor cells. During capture, the rods are covered in a detachable, ultra-thin (~25 micron) inert Samples loaded into 6-well plates were placed into the capture position of the MagSweeper. The magnetic rods engaged inside their plastic sleeves were programmed to sweep through the immunomagnetically-labeled blood sample at 2 mm/sec in 13 concentric loops, each loop offset by 1 mm. The capturing was immediately repeated. The sleeved magnetic rods then moved to a wash station where they entered and swept through 10 ml of PBS for 30 seconds and then washed again in 10 ml of fresh PBS. The rods then entered a fresh 6-well plate containing PBS at the release station. The rods were then disengaged from their sleeves. This release plate was then moved to the capturing position and the capture-wash-release protocol was repeated at least one additional time using a fresh sleeve.

Procedure for Labeling and Single Cell Analysis

To capture CTCs, the CTC cell membrane was labeled with 4.5 µm paramagnetic beads (Dynabeads) functionalized with anti-EpCAM antibodies. Large magnetic beads permit isolation of cells with only one magnetic bead attached, and reduce the need for high EpCAM antigen expression by the CTCs. Cells may only have one bead attached, or may have multiple beads attached.

The MagSweeper platform allows visual verification of CTCs released into solution; these CTCs, free from contaminating blood cells, were individually extracted by pipette aspiration, thereby permitting single cell analysis. While another technology, cell sorting, can also produce pure single cells, many cells are adsorbed in the tubing, thus requiring an input of hundreds of CTCs, making current sorting technologies impractical for single cell CTC analysis for most cancer patients.

CTCs were visually identified and photographed using an Axio Observer A1 inverted microscope (Carl Zeiss MicroImaging, Göttingen, Germany). Single cells were manually aspirated using a Pipetman P2 (Gilson, Inc, Middleton, Wis.) under visual guidance. Cells were collected in 1 µl volume and added to 0.2 µl of SUPERase-In™ RNAse inhibitor (Applied Biosystems/Ambion, Austin, Tex.) and frozen on dry ice. Samples were stored at minus 80° C. until processed.

These microscopic observations demonstrated that the present method and device produced a pure composition of CTCs, with zero contaminating blood cells such as white blood cells, red blood cells, platelets or the like. In the present methods, using a clinically realistic human blood sample of about 9 ml, a composition comprising at least 10 CTCs can be obtained, representing a new composition of essentially pure (at least 90% pure, preferably 95% pure and often 100% pure) human CTCs obtained, as implied by the definition of CTCs, from human peripheral blood. This composition was seen as free of extrinsic cells by microscopic examination.

The performance of the MagSweeper was tested by measuring capture efficiency and cell purity by spiking 5-50 magnetically-labeled cells from MCF7 and SKBR3 human breast cancer cell lines into normal whole blood and processing the samples with the MagSweeper. In replicate experiments (n=9 for each cell line tested), it was found that the cell capture rate was 59%±27% for MCF7 cells and 66%±17% for SKBR3 cells. In all cases, cells were isolated with 100% purity after two rounds of capture-wash-release as determined by visual inspection (zero contaminating WBCs).

Pilot Studies Showing Viability and Gene Expression of Captured Cells

Figure 11A:
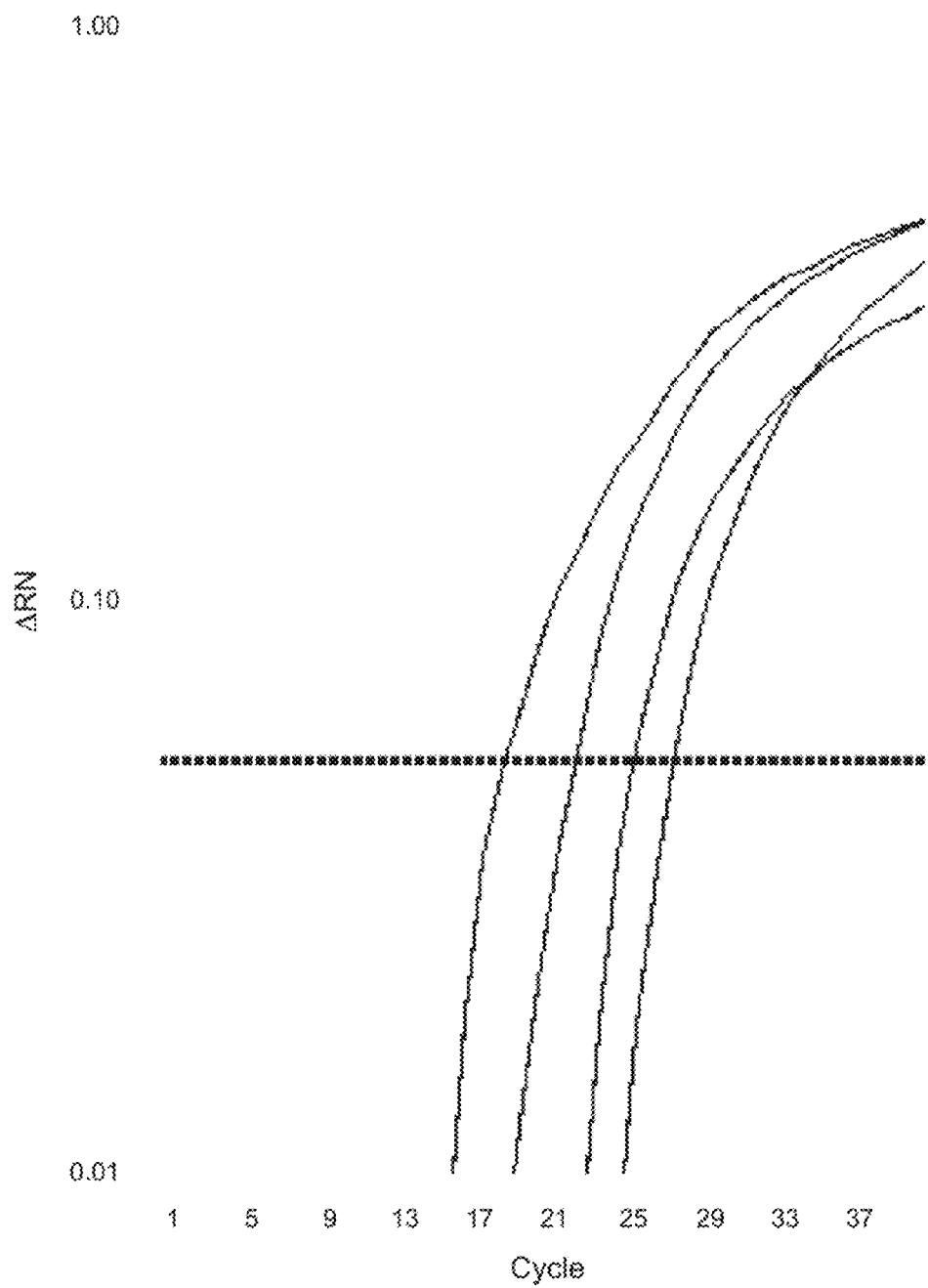
FIG. 11A-C is a series of three graphs showing amplification curves for CD45 and β-actin in four individual CTCs (11A), leukocytes (11B), and Reference RNA (11C). The four individual CTCs were isolated from two women with metastatic breast cancer, and 0.01 ng of human reference RNA was used in 11C.
Figure 11B:
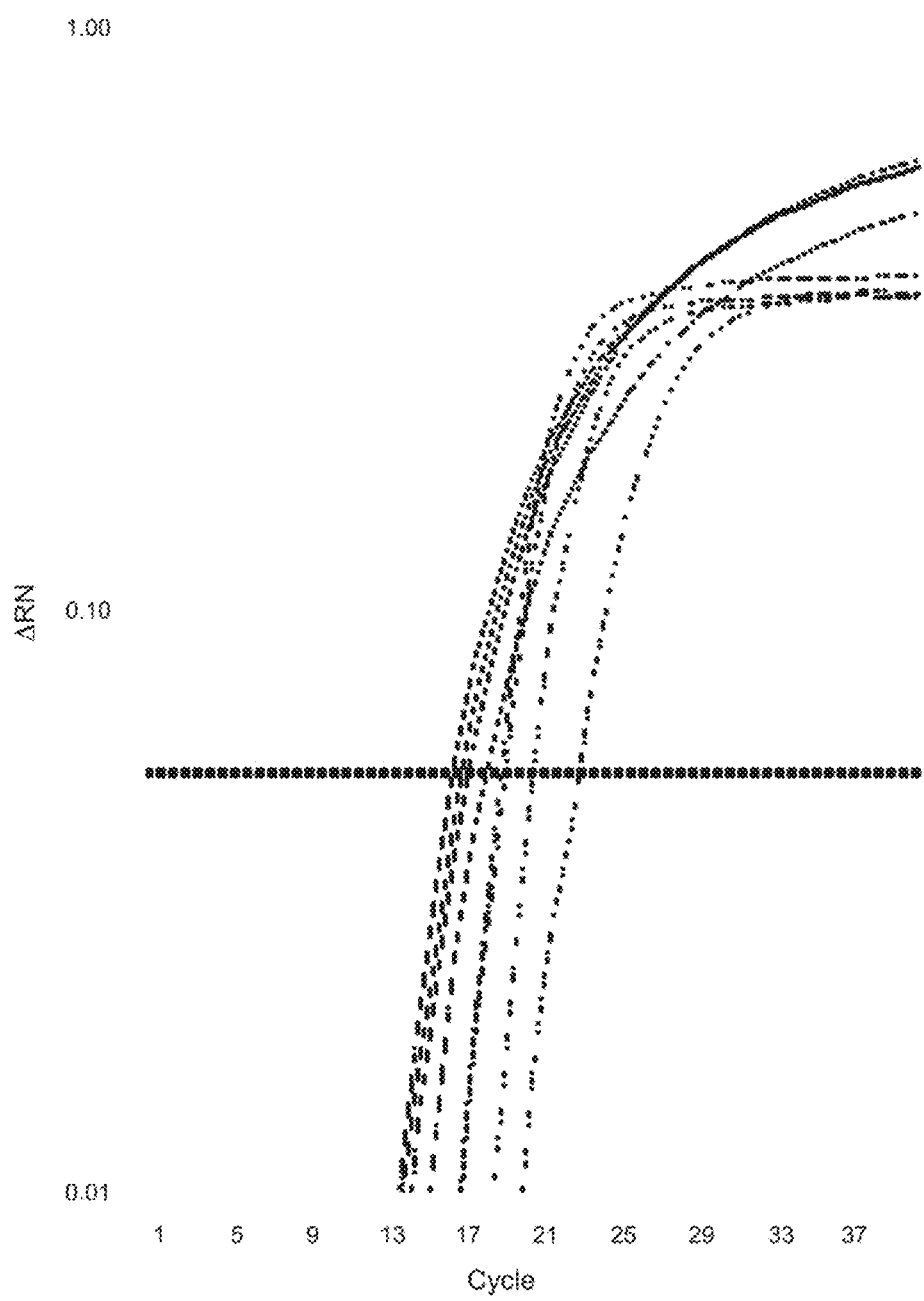
Figure 11C:
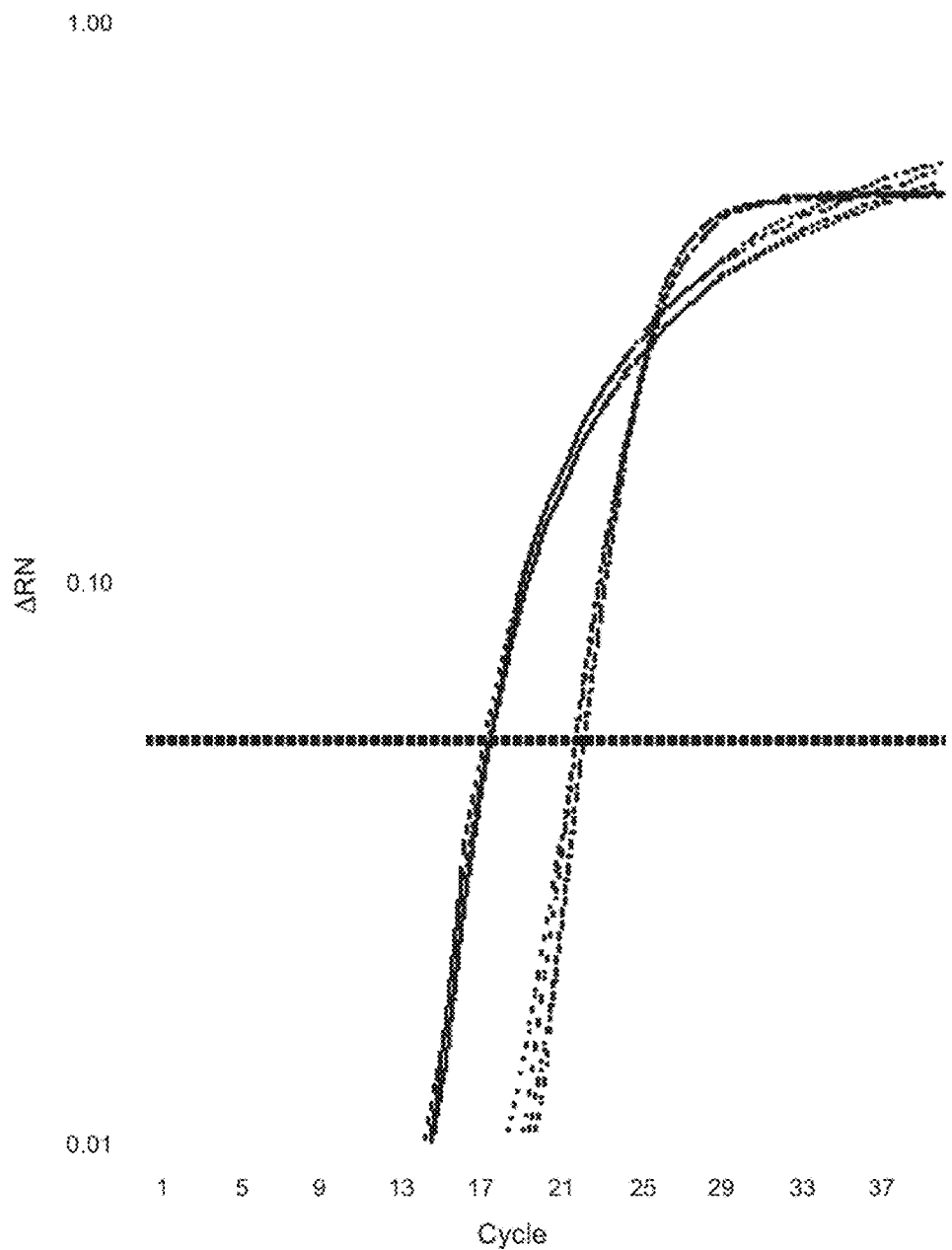
Figure 12:
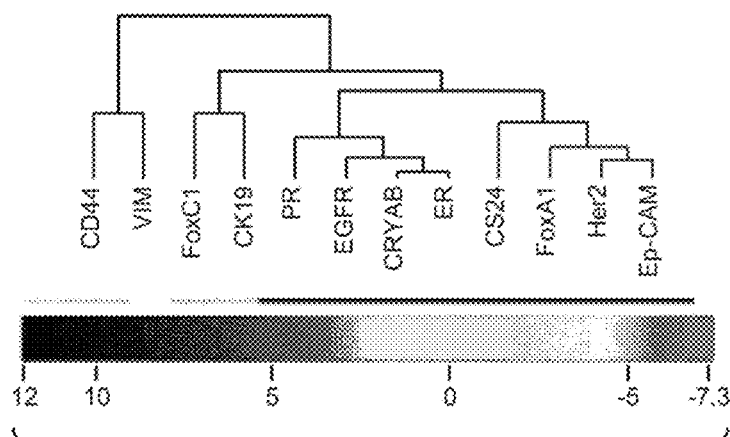
FIG. 12 is a cluster analysis of single CTCs normalized for expression of GAPDH showing different populations of CTCs, including a putative mesenchymal-like cancer stem cell. Scale bar represents Δ Ct; higher Δ Ct values indicate lower gene expression.

To study the ability of the MagSweeper to capture CTCs in a physiological setting, a model system was used to produce CTCs in mice. Orthotopic tumor xenografts in twenty immunocompromised (NOD-SCID) female mice were created by injecting their mammary fat pads with MDA-MB-231 human breast cancer cells. Fifty days post injection, the average tumor volume was 1.5 cm³ and macroscopic lung metastases were observed in all mice. Control mice injected with saline did not develop primary tumors or metastases. Mouse blood was labeled with immunomagnetic beads (against human EpCAM antigen) and processed with the MagSweeper. Greater than 100 CTCs were captured from the blood of each tumor-bearing mouse but no CTCs were captured from the blood of control mice. The CTCs isolated by the MagSweeper retained their ability to grow in culture, again confirming CTC viability. Single cell biomarker profiles of all captured CTCs matched single cells from the parental cell line used to generate the tumor xenografts. Similar to the in vitro experiments, these mouse experiments demonstrated that high quality CTCs could be captured in vivo without altering gene expression. Again, 100% purity of all extracted CTCs was visually confirmed. The results shown in FIG. 11 indicate the integrity of the RNA from the isolated CTCs.

Single Cell Analysis

To determine the effect of the present capture method on CTC gene expression profiles, single captured cells, which generally contain picogram quantities of RNA, were analyzed with high-throughput microfluidic chips that use integrated fluidic circuits and integrated micromechanical valves to perform highly sensitive parallel qRT-PCR assays (Fluidigm 48.48 Dynamic Array, described further in J. Liu, C. Hansen, Quake S. R. Anal. Chem. 75, 4718-4723 (2003) and S. L. Spurgeon, R. C. Jones, R. Ramakrishnan, PLoS ONE 3, e1662 (2008).)

Samples were pre-amplified with the CellsDirect qRT-PCR kit (Invitrogen, Carlsbad, Calif.). The 15 TaqMan expression assays (20×) (Applied Biosystems, Foster City, Calif.) were performed for the following genes, where the number in parentheses set forth sources of further information, in the form either of an Applied Biosystems catalog number (genes 1-3) or a gene symbol, Gene hCG2043341 Celera Annotation:

1. Human GAPD (GAPDH) Endogenous Control (4333764F);
2. Human ACTB (beta actin) Endogenous Control (4333762F);
3. Human RPLPO (large ribosome protein) Endogenous Control (4333761F);
4. ESR1 (ER, Hs00174860_m1);
5. PGR (PR, Hs00172183_m1);
6. ERBB2 (Her2, Hs00170433_m1);
7. VIM (Hs00185584_m1);
8. KRT19 (CK19, Hs00761767_s1);
9. TACSTD1 (Ep-CAM, Hs00158980_m1);
10. CD44 (Hs00153304_m1);
11. CD24 (Hs00273561_s1);
12. EGFR (Hs00193306_m1);
13. CRYAB (Hs00157107_m1);
14. FOXA1 (Hs00270129_m1);
15. FOXC1 (Hs00559473_s1).

These TaqMan gene expression assays (20×) were pooled together and diluted with TE buffer to yield 1×Assay mixture. The pre-amplification was done in 10 µl volume including 5.0 µl Cells Direct 2× Reaction Mix, 0.50 µl 1× pooled Assay Mixture, 1 µl Cell [or human reference RNA (Stratagene, La Jolla, Calif.)], 2.5 µl TE (pH 8.0), and 1 µl RT-Taq enzyme. The RT step was performed at 50° C. for 15 minutes, followed by 18 cycles of amplification (95° C. for 15 minutes and then 60° C. for 4 minutes). Pre-amplified cDNA were diluted 2 times in TE buffer and stored at −20° C.

CellsDirect™ (from Invitrogen Corp.) qRT-PCR kits deliver highly sensitive and specific, real-time qPCR results directly from cells, without the need for an RNA purification step when testing with less than 10,000 cells per reaction to as low as 1 cell. CellsDirect™ technology is designed for maximum sensitivity with small samples. By eliminating costly, time-consuming RNA purification procedures, it is especially valuable for high-throughput applications and is ideal for gene expression experiments. TaqMan Universal Master Mix (Applied Biosystems, Foster City, Calif., [TaqMan Universal Master Mix Reagents provide a PCR mix that may be used with any appropriately designed primer and probe to detect any DNA or cDNA sequence].) and 48.48 dynamic array chips, the NanoFlex™ 4-IFC Controller and the BioMark Real-Time PCR System (Fluidigm Corporation, South San Francisco, Calif.) were used for multiplex qRT-PCR. Arrays were performed following the standard Fluidigm protocol (Spurgeon et al., "High Throughput Gene Expression Measurement with Real Time PCR in a Microfluidic Dynamic Array," PLoS ONE 3(2): e1662. doi:10.1371 2008). The chip was first primed with Krytox in the NanoFlex™ 4-IFC Controller. Then, 5 μl sample mixtures containing 2.5 μl 2× TaqMan Universal Master Mix, 0.25 μl DA sample loading reagent (Fluidigm Corporation, South San Francisco, Calif.), and 2.25 μl preamplified cDNA were pipetted into the sample inlets. 5 μl assay mix containing 2.5 μl 20× gene expression assay mix (Applied Biosystems, Foster City, Calif.) and 2.5 μl DA Assay loading regent (Fluidigm Corporation, South San Francisco, Calif.) were pipetted into the assay inlets. The chip was then loaded and mixed in the NanoFlex™ 4-IFC Controller. qRT-PCR reactions of the chip were performed using the BioMark Real-Time PCR System. The cycling program consisted of 10 min at 95° C. followed by 40 cycles of 95° C. for 15 sec and 60° C. for 1 min.

Each Biomark chip can assay 48 samples for 48 gene targets. The results shown in Table 3 are representative Ct values based on measurements of 15 genes in triplicate using only human sequence specific primers, with water as a negative control. Table 3 below shows a numerical sample of data earlier presented as a heat map (not shown). The table indicates the profile of expression of three housekeeping genes (GAPDH, Beta Actin and PRLPO) and twelve genes associated with breast cancer in patients A through G. While the housekeeping gene levels did not vary from cell to cell, marked differences in gene expression were seen in the other genes measured, even from the same patient. Table 4 shows that the values also varied from patient to patient.

TABLE 4

|    | FOXA1 | CD44  | ER    | PR | VIM   | ERBB2 | EpCAM |
|----|-------|-------|-------|----|-------|-------|-------|
| A1 | 21.4  | 20.27 | 24.27 |    | 21.55 | 18.2  | 22.63 |
| A2 |       |       |       |    | 22.34 |       |       |

TABLE 4-continued

|    |       |       |       |    |       |       |       |
|----|-------|-------|-------|----|-------|-------|-------|
| B1 |       |       | 27.72 |    |       | 19.05 | 26.06 |
| B2 |       |       |       |    |       |       |       |
| B3 |       |       |       |    |       | 23.54 |       |
| C1 |       |       | 22.99 |    |       | 21.58 |       |
| D  |       |       | 23.16 |    |       |       |       |
| E1 |       |       | 25.94 |    |       | 24.22 |       |
| F1 |       |       |       |    |       | 20.75 | 25.13 |
| F2 |       |       |       |    |       |       |       |
| G1 |       |       |       |    |       | 23.19 |       |

|    | GAPDH | B-Actin | RPLPO | RPLPO | CRYAB | EGFR |
|----|-------|---------|-------|-------|-------|------|
| A1 | 14.75 | 15.95   | 18.46 | 18.39 | 17.12 | 23.7 |
| A2 | 19.58 | 21.03   | 24.67 | 24.1  |       |      |
| B1 | 19.1  | 21.91   | 23.15 | 23.51 |       |      |
| B2 |       | 22.62   | 25.59 | 26.74 |       |      |
| B3 | 20.92 | 18.47   | 23.41 | 22.38 |       |      |
| C1 | 19.88 | 18.89   | 23.4  | 23.66 |       |      |
| D  | 22.51 | 27.89   | 25.5  | 24.77 |       |      |
| E1 | 29.86 | 32.05   | 27.36 | 27.79 |       |      |
| F1 | 21.42 | 22.87   | 23.55 | 23.54 |       |      |
| F2 | 21.15 | 20.12   | 25.98 | 27.38 |       |      |
| G1 | 22.07 | 24.47   |       | 30.09 |       |      |

|    | FOXC1 | CD24  | CK19  |
|----|-------|-------|-------|
| A1 | 22.63 | 19.55 | 17.34 |
| A2 |       |       |       |
| B1 |       |       |       |
| B2 | 23.43 |       |       |
| B3 |       | 24.91 | 25.21 |
| C1 |       | 31.65 |       |
| D  |       |       | 23.05 |
| E1 |       |       |       |
| F1 | 24.41 |       | 19.5  |
| F2 | 24.14 | 26.39 | 22.29 |
| G1 |       |       |       |

TABLE 4A

Results from Patient A Only

|      | GAPDH | B-Actin | RPLPO | CRYAB | EGFR | FOXA1 | CD44  | ER    |
|------|-------|---------|-------|-------|------|-------|-------|-------|
| A1-1 | 14.75 | 15.95   | 18.46 | 17.12 | 23.7 | 21.4  | 20.27 | 24.27 |
| 2    | 14.81 | 16.8    | 18.33 |       |      | 21.49 | 22.97 |       |
| 3    | 14.42 | 16.67   | 17.8  |       |      | 23    | 21.13 |       |
| 4    | 14.53 | 15.25   | 17.88 |       |      | 21.71 | 20.4  |       |
| 5    | 16.66 | 18.77   | 19.85 | 23.15 |      |       |       |       |
| 6    | 17.93 | 19.09   | 22.54 |       |      |       |       |       |
| 7    | 18.09 | 19.15   | 22.04 |       |      | 25.76 |       |       |
| 8    | 13.83 | 16.38   | 17.97 |       |      | 20.84 | 20.13 |       |

|      | PR | VIM   | ERBB2 | EpCAM | FOXC1 | CD24  | CK19  | H2O |
|------|----|-------|-------|-------|-------|-------|-------|-----|
| A1-1 |    | 21.55 | 18.2  | 22.63 | 22.63 | 19.55 | 17.34 |     |
| 2    |    | 22.8  | 20.64 | 25.04 | 24.17 | 20.81 | 18.37 |     |
| 3    |    |       | 18.79 | 24.65 | 24.31 | 19.91 | 18.67 |     |
| 4    |    |       | 18.42 | 22.76 |       |       |       |     |
| 5    |    | 22.84 | 20.79 | 25.73 | 23.41 | 25.38 | 19.97 |     |
| 6    |    |       | 22.68 | 24.72 |       |       |       |     |
| 7    |    | 22.85 |       |       | 24.43 | 25.71 | 19.66 |     |
| 8    |    |       |       |       |       |       |       |     |

Tables 4 and 4A show gene expression data of 15 genes, where expression was performed on single CTCs isolated from seven patients, indicated by the seven letters A-G. Each of the 15 genes was measured in triplicate (data shown for one measurement) for each single CTC. Patients A, B and F had sequential blood draws, denoted as A1 and A2; B1, B2, and B3; F1 and F2. Table 3A shows separate cells from the same patient to illustrate variability among CTCs.

Gene expression profiles for single MCF7 cells spiked into blood and captured by the MagSweeper were compared with the parental cell line. There was no marked change in gene expression of the cells after labeling and capture. Moreover, at the single cell level, the cellular heterogeneity of the parent cell line was recapitulated in the single cells captured by the MagSweeper. This is a critical aspect for human CTC studies: if different populations of CTCs exist in a given cancer patient, CTC heterogeneity could only be observed at the single cell level.

Isolation of CTCs from Metastatic Breast Cancer Patients

The above in vitro and in vivo preclinical experiments showed that the present device provided gentle isolation and complete purification of CTCs without perturbing cell viability or gene expression. MagSweeper performance was then tested in clinical applications. With informed consent, blood samples were obtained from eleven women with metastatic breast cancer and five healthy volunteers (normal controls). Patients with known metastatic breast cancer or healthy normal controls were consented prior to sample collection in accordance with Stanford's Human Subjects Research Compliance Board and HIPAA regulations. Blood was collected in 10 mL BD Vacutainer plastic EDTA tubes (Becton Dickinson, Franklin Lakes, N.J.). Blood was collected by venipuncture or from implanted venous access ports or both. The first 3 cc from each blood draw was discarded to prevent contamination by skin epithelial cells from the needle puncture site. Then approximately 9 ml of blood was collected from each human subject and kept at room temperature. All blood samples were processed within 3 hours of collection. The blood was split into three tubes and diluted to 6 ml each with PBS and labeled with 3.4 µl of Dynabeads® at room temperature with constant mixing for 15 minutes. The samples were then placed in an EasySep Magnet (Stem Cell Technologies Vancouver, BC, Canada) for 2 minutes and then mixed for another 15 minutes. These samples were added to wells of a 6-well plate, brought up to 10 ml each with PBS, and then processed by the MagSweeper. The 4.5 µm beads were coated with the monoclonal BerEP4, which is specific for an epithelial cell surface epitope (EpCAM) and is further described in *J Clin Pathol.*, 1990 March; 43(3): 213-219. The beads were incubated for 30 min. at room temperature with constant mixing. The EasySep magnet was used in a premixing step to help attach the beads to the antibodies.

Figures 10A, 10B, 10C, 10D, 10E:
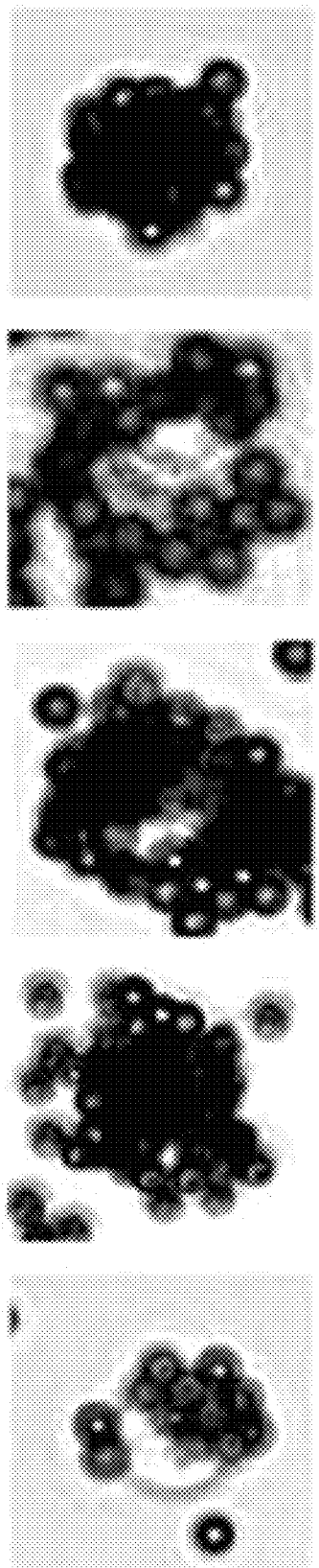
FIG. 10A-E are photomicrographs of CTCs from patients with metastatic breast cancer.

CTCs were extracted from all eleven (100%) cancer patients and none (0%) of the healthy controls. This is consistent with previous work that identified CTCs in 60-100% of patients with metastatic breast cancer and 0-1 CTCs in healthy controls. The 235 individual CTCs captured by the MagSweeper were each photographed then analyzed using high throughput microfluidic arrays to measure 15-gene expression profiles. For each single CTC, the expression of the following genes was profiled, as shown in FIG. 10: three housekeeping genes (GAPDH, β-Actin and RPLPO); two breast cancer endocrine biomarkers (estrogen receptor, ER, and progesterone receptor, PR); two receptor tyrosine kinase genes for which targeted therapy is available for breast cancer treatment (ERBB2/HER2 and EGFR); three genes previously identified by DNA microarray studies as being associated with luminal and basal subtypes of breast cancer (FOXA1, FOXC1, and CRYAB); two epithelial genes (CK19 and EpCAM); two genes for cancer stem cell identification (CD44 and CD24); and a mesenchymal gene (vimentin, VIM) implicated in epithelial-to-mesenchymal transition (EMT) and mesenchymal-to-epithelial transition (MET) and breast progenitor cells.

All eleven breast cancer patients were receiving chemotherapy at the time their blood samples were obtained. The MagSweeper used here captured CTCs with measurable expression in at least one housekeeping gene in the blood of ten (91%) of the metastatic breast cancer patients. We conservatively defined a CTC as having "robust gene expression" only if all three housekeeping genes were expressed; this was done to avoid analyzing CTCs with degraded RNA, as might be observed in CTCs undergoing apoptosis or cytotoxic degradation. Of the eleven patients, seven (64%) had at least one CTC with robust gene expression. 48 CTCs had robust gene expression. The other 187 CTCs expressed zero to two housekeeping genes. Consistent with our findings, morphologic and molecular studies have shown that fragmented or apoptosing CTCs are commonly observed in the blood of patients undergoing treatment for metastatic disease.

The profiles of standard breast cancer biomarkers (ER, PR, and HER2) for primary tumor, any available metastases, and CTCs for the seven patients with robust CTC gene expression data are compared in (Table 5). There was considerable discordance between primary tumors and CTCs. In particular, among patients who had ER-positive breast cancers excised years earlier and who now had multiple distant metastases, their CTCs almost exclusively showed an ER-negative phenotype. This could explain why endocrine therapies ultimately fail to control metastatic disease in patients with hormone receptor positive primary breast cancer. All patients had some CTCs with triple negative (ER negative/PR negative/HER2 negative) profiles, even though none originally had triple negative primary tumors. In particular, one patient (Patient B, samples B1, B2, B3) had a primary breast cancer that showed strong HER2 amplification, yet her metastatic disease continued to progress on trastuzumab, a humanized monoclonal antibody that targets the HER2 cell surface receptor. Unlike her primary cancer, only one of her CTCs expressed HER2 and almost all other of her CTCs were triple negative (16/19, 1/1 and 7/7, for samples B1, B2 and B3, respectively). The triple negative phenotype of the majority of her CTCs matched the triple negative phenotype of her biopsied vertebral metastasis, suggesting that CTC biomarker profiles may better reflect metastatic phenotypes than primary tumor profiles. It also may explain trastuzumab resistance in progressing metastatic disease. In contrast to Patient B, Patient A (sample A1) expressed HER2 in most of her CTCs. Following treatment with trastuzumab, her CTC count decreased from hundreds to five cells per 9 cc of blood (sample A2). Among the five CTCs isolated in sample A2, only one expressed all three housekeeping genes and this cell lacked HER2 expression.

TABLE 5

| Patient ID | Primary tumor(s) | Metastatic tumor | CTC profile (ER, PR, HER2) | Vimentin expression | Mesenchymal-like stem cells (MSC) | Partially differentiated epithelial (PDE) | Differentiated tumor epithelial (DTE) |
|---|---|---|---|---|---|---|---|
| A | ER−, PR−, HER2+ | N/A | Sample 1 (−, −, +) (5/8) (+, −, +) (1/8) (−, −, −) | 4/8 ----- 1/1 | 0/8 ----- 0/1 | 2/8 ----- 1/1 | 6/8 ----- 0/1 |

TABLE 5-continued

| Patient ID | Primary tumor(s) | Metastatic tumor | CTC profile (ER, PR, HER2) | Vimentin expression | Mesenchymal-like stem cells (MSC) | Partially differentiated epithelial (PDE) | Differentiated tumor epithelial (DTE) |
|---|---|---|---|---|---|---|---|
| B | ER+, PR+, HER2+ (left) ER-, PR-, HER2+ (right) | ER-, PR-, HER2- (bone metastasis) | (2/8) ----- Sample 2 (-, -, -) (1/1) Sample 1 (-, -, +) (1/19) (-, +, -) (1/19) (+, -, -) (1/19) (-, -, -) (16/19) ----- Sample 2 (-, -, -) (1/1) ----- Sample 3 (-, -, -) (7/7) | 18/19 ----- 0/1 ----- 3/7 | 7/19 ----- 0/1 ----- 0/7 | 8/19 ----- 1/1 ----- 4/7 | 3/19 ----- 0/1 ----- 0/7 |
| C | unknown | ER+, PR-, HER2- (bone metastasis) | (-, -, -) (3/3) | 1/3 | 0/3 | 3/3 | 0/3 |
| D | ER-, PR+, HER2- | ER+, PR-, HER2- (lymph node metastasis) | (-, -, -) (5/5) | 0/5 | 0/5 | 2/5 | 0/5 |
| E | ER+, PR+, HER2 unk | N/A | (-, -, -) (1/1) | 1/1 | 1/1 | 0/1 | 0/1 |
| F | ER+, PR+, HER2 unk | ER+, PR-, HER2- (chest wall recurrence) | Sample 1 ( -, -, -) (1/1) --- Sample 2 (-, -, -) (1/1) | 1/1 ----- 0/1 | 0/1 ----- 0/1 | 1/1 ----- 1/1 | 0/1 ----- 0/1 |
| G | ER+, PR+, HER2- | N/A | (-, -, -) (1/1) | 1/1 | 0/1 | 1/1 | 0/1 |

Table 5 above shows the biomarker profiles for seven patients with metastatic breast cancer who had at least one CTC with robust gene expression (expression of all three housekeeping genes). Patients A, B and F had sequential blood draws over a four month period. Standard breast biomarker profiles (ER, PR, HER2) are shown for primary tumor, metastases when available, and CTCs. For standard biomarker profiles and each CTC phenotype (MSCs, PDEs, and DTEs), the numerator is the number of CTCs of that phenotype and the denominator is the total number of CTCs isolated from each sample. Data is shown for only CTCs with robust gene expression. Vimentin was the most commonly observed gene expressed by CTCs. Differentiated tumor epithelial cells (DTEs) were defined as CTCs that expressed ER, PR, HER2, or EGFR and at least one other breast epithelial gene: FOXA1, FOXC1, CRYAB, EpCAM, or CK19. Partially differentiated epithelial cells (PDEs) were defined by lack of expression of ER, PR, HER2, or EGFR but still expressed at least one epithelial marker. We also denoted CTCs to be PDEs if they expressed vimentin alone or CD24 because of where they clustered, although further characterization is necessary. CTCs that co-expressed vimentin and CD44 were defined as mesenchymal-like cancer stem cells (MSCs).

Most CTC profiles were striking in their expression of vimentin and CD44. Vimentin, expressed by mesenchymal and breast progenitor cells, is associated with cell motility, invasion, high tumor grade, and metastasis). CTCs from six of the seven patients (86%) and 60% of all CTCs with robust gene expression strongly expressed vimentin. In addition, we found CD44-expressing CTCs in over 70% of patients and more than half of all CTCs with robust gene expression.

CD44 is a cell surface adhesion molecule that is expressed by putative breast cancer stem cells. Among cells with degraded profiles (expressing 0-2 housekeeping genes), CK19 was the most commonly expressed gene (36%-62%), and vimentin and CD44 were only expressed in 12-27% and 0-27%, respectively. This suggests that more epithelial-like cells may be more susceptible to degradation in the blood stream of patients undergoing chemotherapy than the more robust vimentin-expressing cells.

In the in vitro experiments, single captured cells recapitulated the heterogeneity of the parental cells. It was thus expected that any variation observed in the clinical samples would similarly reflect distinct cell populations within metastases. When analyzing the isolated CTCs from patients with metastatic breast cancer, it was found that they displayed a spectrum of gene expression, ranging from more differentiated tumor epithelial cells (DTEs) to partially differentiated epithelial cells (PDEs) to mesenchymal-like cancer stem cells (MSCs). DTEs expressed ER, PR, HER2 or EGFR and at least one other breast epithelial marker such as FOXA1, FOXC1, CRYAB, EpCAM, or CK19. PDEs lacked expression of ER, PR, HER2 or EGFR, but still expressed at least one epithelial marker. We also denoted cells to be PDEs if they expressed vimentin alone or CD24, although they will require further characterization in a larger series. Finally, we discovered an important class of CTCs that co-express vimentin and CD44 without other markers; these cells appear to represent a class of mesenchymal-like cancer stem cells (MSC) or breast progenitor cells. These particular CTCs may correspond to the basal B phenotypes described in breast cancer cell lines by Neve et al. (R. M. Neve et al., *Cancer Cell*, 10, 515-527 (2006)) and breast progenitor cells identified in primary human breast tumors by Korshing et al. (E. Korsching et al., *J. Pathol.*, 206, 451-457 (2005). In two of the three patients with serial blood analyses, CTC populations varied over time, showing a decreasing proportion of DTEs among robustly expressing CTCs. The third patient had only PDEs. We thus propose that PDEs and MSCs are more chemoresistant than DTEs, and the presence of these less differentiated CTCs represents a hallmark of progressive metastatic disease. The inherent variation of gene expression of individual CTCs in patients undergoing treatment for widespread metastatic breast cancer suggests that pooling CTCs for genetic analysis would obscure specific populations and that single cell analysis is needed to achieve a complete picture of metastatic biology. In these results 25% of the human CTCs with robust gene expression have a mesenchymal stem cell-like phenotype, which may require specific therapeutic targeting (R. S. Finn et al., Breast Cancer Res. Treat. 105, 319-326 (2007)). Phenotyping individual CTCs in metastatic cancer may lead to more personalized therapy.

Additional Cell Studies

50 HLA-A2 positive cells were spiked as target cells into a solution containing different amounts of HLA-A2 negative cells. The target cells (HLA-A2) were labeled with 4.5 μm magnetic beads functionalized with an anti-HLA-A2 antibody. The capture rate and purity of the targeted cells isolated by MagSweeper after two rounds of capture-wash-release was found to be approximately 60%, independent to the number of background cells. The purity of isolated HLA-A2 cells was 100% until the background cells are in excess of $2\times10^5$ and is 89%±2% when the number of background cells is $2\times10^6$. In addition, this data indicates the enrichment of target cells by $2.5\times10^5$-fold when the background cells are as high as $2\times10^7$.

After visual inspection of the captured cells under fluorescent microscopy, we found that the majority of contaminant cells were attached to magnetic beads. This indicates that the purity is limited by the antibody specificity and reagent quality.

In another experiment, 50 stained cancer cells from the human breast cancer cell line MCF7 were spiked into 1 ml of stained peripheral blood drawn from healthy human volunteers. For ease of detection, the target MCF7 cells and background blood cells were stained with SNARF-1 (Invitrogen, CA) and CFDA SE (Invitrogen, CA) fluorescent dyes, respectively, according to the manufacturer's recommendation. The MCF7 cells were labeled with 4.5 μm paramagnetic beads functionalized with antibodies against the epithelial cell adhesion molecule (EpCAM) which is expressed on the cell membrane of epithelial cells, but not on leukocytes or red blood cells. The 4.5 μm magnetic beads permitted isolation of target epithelial cells even with only one bead attached to the cells, which makes the procedure suitable for isolating CTCs with moderate to low EpCAM expression.

The capturing efficiency of MCF7 cells by MagS weeper was found to be to be 66%±10% with the purity of 23%±5%. However, it was found that if the separation and labeling process was carried out at 4° C., the purity can be increased to 91%±6%.

To assess whether the MagSweeper protocol perturbs the gene expression profile of the CTCs during the isolation process, the genome wide transcriptome expression profile of MCF7 cells was studied using microarray analysis. The expression profiling of 20,000 MCF7 cells grown in culture media, was compared with similar number of MCF7 cells incubated for thirty minutes with anti-EpCAM magnetic beads before and after MagSweeper isolation. Coefficients of variation of gene expression between cultured cells and after MagSweeper isolation were comparable, suggesting little evidence of increased variation due to isolation. Moreover, gene expression fold changes between cultured cells and MagSweeper were analyzed. 42% of probe sets have changes less than 10%, another 35% have changes 10-25%, and 17% additional between 25-50%. Statistical analysis of gene expression between the culture cells and MagSweeper reveals that none of the changes are significant at 5% false discovery rate (FDR), indicating that the MagSweeper isolation protocol does not induce any significant perturbation in the gene expression profile of the cells during the isolation process.

Further Manipulation of Isolated Rare Cells
Automated Single Cell Retrieval

Figure 13:
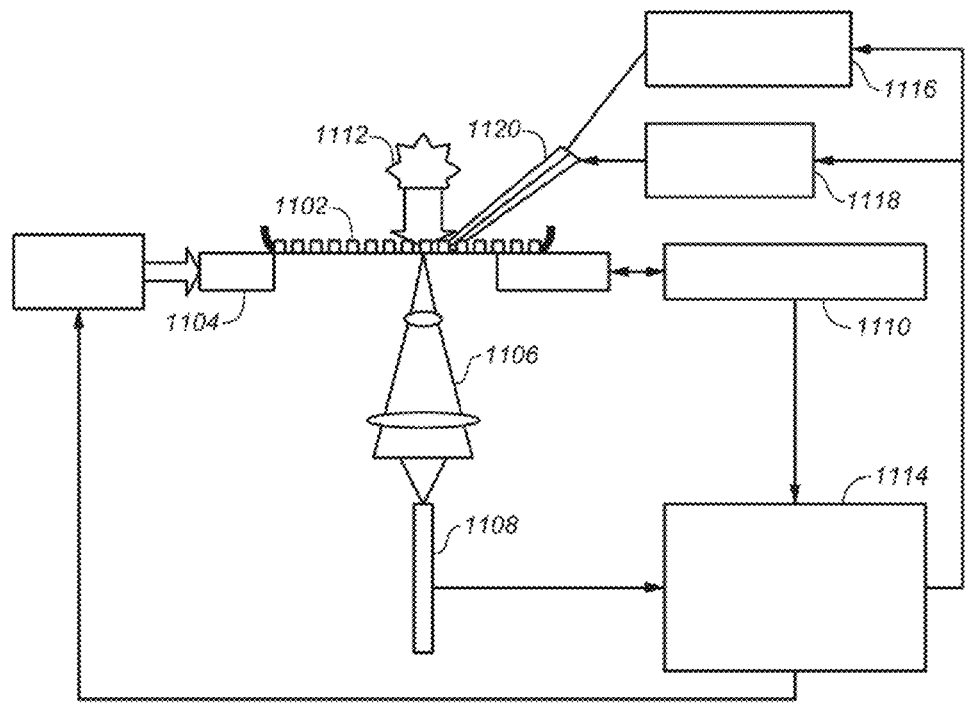
FIG. 13 is a schematic drawing of an automated cell extraction system, where clusters of cells may be manipulated to yield individual cells.

The method for obtaining an essentially pure composition containing may comprise a post-processing sample preparation step that will automate single cell identification, extraction, and deposition. This may be done by automated aspiration and magnetic microextraction, where a single isolated cell is deposited into a collection tube containing 1-2 microliters of fluid in preparation for multiplex molecular analysis. Referring now to FIG. 13, there is shown a schematic illustration of an exemplary fully automated cell extraction system, where one may obtain a single viable cell from the cluster of bead-coated cells obtained from the MagSweeper. In this device, a sample containing targets 1102, i.e., cell clusters or cells obtained from the collection well of the present separation device, are placed on a computer controlled mechanically driven stage 1104, which is used to hold the cells. An inverted microscope 1106 images the cells and its view is transmitted to a linear CCD image sensor 1108 which can detect cells and their shapes and other visual characteristics. An interferometer 1110 is also optically connected to the cells to obtain information about the light striking cells from the illumination source 1112. A control computer 1114 receives data from the image sensor 1108 and the interferometer 1110. The computer 1114 also controls an actuator 1116, through a mechanical positioned 1118. The actuator 1118 may be connected an automated pipette or microextractor 1120 or a magnetic device, as described below. The computer uses image recognition software to and information received from the interferometer and the CCD image sensor. In operation, the sample containing the targets is continuously scanned through a ribbon of illumination. A linear charge-coupled device (CCD) then acquires the image line by line. The image is then assembled into a two-dimensional image in the control computer. The control computer is programmed to identify each target, as described below. Using stage position information from the interferometer, and line and height information from the CCD, the computer, in response, moves the microextractor tip into position. The target (individual cell) may then be extracted. The control computer will then actuate the mechanical positioner and the microextractor will be moved to the collection tube (not shown) where the target is released. This process will be repeated for each target in the sample.

Automated Pipetting

One method to obtain a single cell from a cell population employs a cell manipulator system such as the Eppendorf TransferMan NK 2™ can serve as an initial system. However, the TransferMan employs a manually operated joystick. A fully automated system may be custom engineered. In one embodiment, the operator would click a cursor on each target in a live image; the combined co-ordinates of the microscope stage and the cursor would then be fed into a computer that would direct the pipette tip to the target. The operator would electronically actuate aspiration of the target into the pipette.

The pipette would then be moved to a collection tube where the target cell would be dispensed. To create a custom system, one may set up an off-the-shelf micromanipulator system such as the Eppendorf TransferMan NK2. This system is attached to the Zeiss Axiovert inverted microscope in our laboratory. A motorized stage system is used to position the samples using operator-assisted visual feedback. Different electronic pipette systems are attached to the micromanipulator for testing. Suitable candidates include handheld instruments such as a Hamilton Gastight digital syringe hand-held instrument that can be set for repetitive aspiration and dispensing, modified for external actuation. The syringes are programmed for extraction and release of a preset volume. Following aspiration of the CTC by either of these electronic pipettes, the pipette can be moved under joystick control for release into a collection tube. For manual aspiration, we originally used a small pipette tip (150 micron internal diameter). However, the sharp rim contributed to cell rupture by giving rise to large local stresses that caused shearing of the target, so we switched to a larger diameter tip (0.5-10 µl micropipette tip, 400 micron internal diameter). If cell rupture due pipette shearing creates a problem in the automated pipetting system, one variant of our pipette design would be to mount a flat perforated cap across the orifice that would provide a cushion. A perforated flat disk silicon end cap can be attached to the end of a glass pipette tip having an end opening of 0.25-0.5 mm, with the disk having 3-5 small perforations.

As an alternative to pipetting a single cell, one may use a magnetic probe which can be micromanipulated to attach to a single cell. The rationale for using a localized magnetic field for CTC extraction is to extract the target without excess beads or solution, and to perform extraction with potentially less cell rupture than achieved by aspiration. A wire made of a soft magnetic material (e.g., pure iron which can be obtained commercially and may be subsequently annealed) to facilitate CTC release (soft magnets can be easily demagnetized). To avoid picking up excess beads along the length of the wire, the wire will be encapsulated by a nonmagnetic material, except at the tip. With this configuration, the magnetic force on a target should fall off rapidly. A simple numerical calculation indicates that it should fall off more than 10-fold within a 1-tip radius distance from the tip surface. The force generated on a target is given by. The force generated on a target is given by $$F = VKH\frac{\partial H}{\partial x}$$

where V is the volume of the target, K its magnetic susceptibility and x is distance.

For soft iron, K can exceed 1000 and the maximum field at the surface can exceed 1 T (Tesla) but a value of 0.2 T might be a more practical maximum. The volume of the target can range from $10^{-15}$ to $10^{-14}$ m$^3$. Operation of the magnetic microextractor involves bringing the tip into close proximity (e.g., less than 100 microns) and then energizing the solenoid by switching on the current. As before, the microextractor is then be moved under joystick control to the collection tube. The current will be switched off for target release. If the target does not release, one may cyclically reverse the magnetic field with decreasing amplitude. An external magnetic field of larger gradient can also be applied to assist target release, similar to the methods already in use in the last step of the MagSweeper operation.

Further Details of Construction of the Magnetic Member

FIG. 9 illustrates the effect of the magnetic field on the cells. In this embodiment a sleeve 902 tightly fits over the magnetic rod along at least a portion of the side of the rod 904, and tightly at the tip. (The spacing is exaggerated for purpose of illustration.) Cells without sufficient magnetic labeling 906 inside the boundary layer 908 are only affected in a lateral direction. Cells with beads 910 sufficient to be within the magnetic force of the rod are drawn to the rod. Thus it is important that the magnetic member used, with sleeve, contain a sharp magnetic gradient to strongly bind the labeled beads which are in close proximity to the rod. The relationship is shown in the plot of B$^2$ versus direction z. A steep magnetic gradient will produce a high strength field near the magnet surface, in this case the tip. The inserted graph in FIG. 9 illustrates the decay of magnetic flux density B$^2$ along the z axis (away from the rod). Beyond about 6 mm from the tip, it was found by modeling that there was very little magnetic force, due to the sharp magnetic gradient.

The present methods may further comprise target recognition technologies for CTC identification without user input. Further description of cell image recognition software may be found in Karacali et al. "Automated recognition of cell phenotypes in histology images based on membrane- and nuclei-targeting biomarkers," *BMC Medical Imaging* 7:7 (2007), found online at www-biomedcentral.com/1471-2342/7/7. As described there, open access systems operated by internet web servers, such as EAMUS™, have recently been developed for extracting quantitative parameters from immunohistochemically stained tissue slides and tissue microarrays. Several commercial software packages have also been developed for cytometric analysis of histological slides and tissue microarrays such as the Tissue Microarray Analysis Software (TMAx) by Beecher Instruments (Beecher Instruments, Inc., 686 Progress Way, Sun Prairie, Wis. 53590, USA), the Extended Slide Wizard by Tripath Imaging (Tripath Imaging, Inc., 780 Plantation Drive, Burlington, N.C. 27215, USA), the Discovery Image Analyser by Becton-Dickinson (Becton-Dickinson Biosciences, Postbus 757, 2400 AT Alphen aan den Rijn, The Netherlands). These systems can be trained to identify isolated CTCs with attached beads and antibodies.

Figure 14:
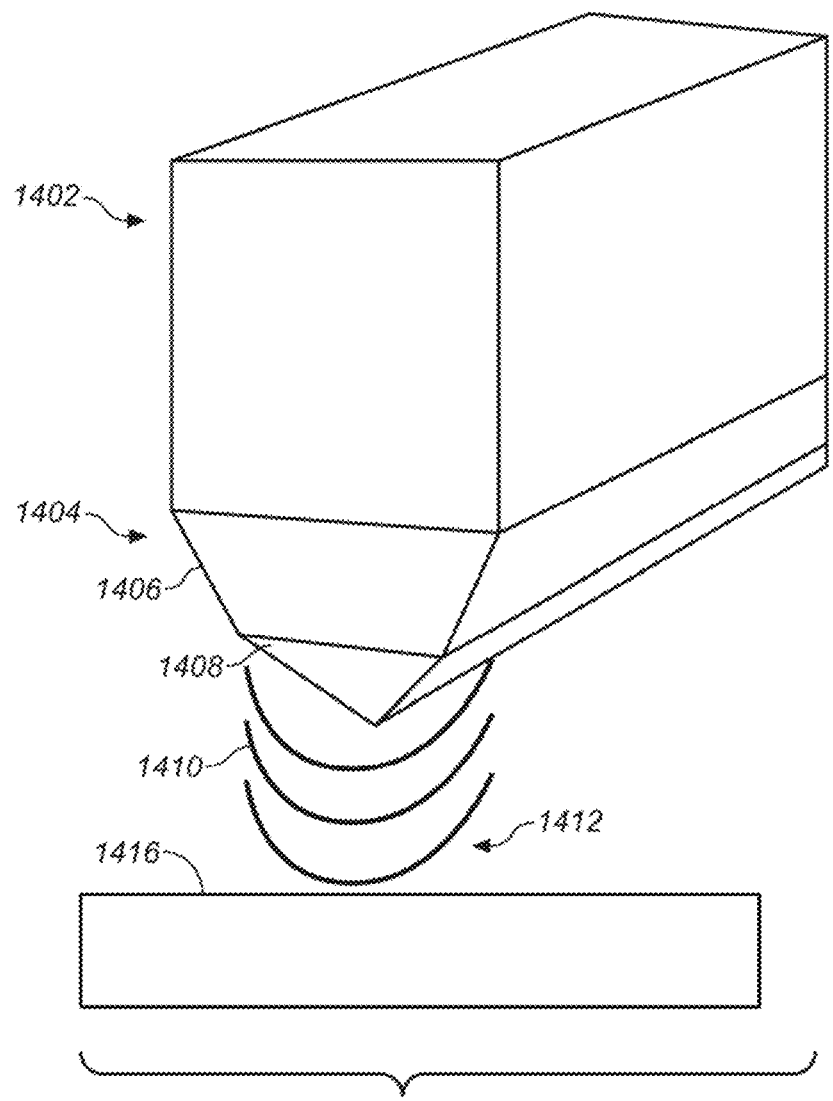
FIG. 14 is a schematic drawing showing an arrangement of a magnet designed to have a large gradient of magnetic field.

Further illustration of magnetic parameters and a possible magnetic member configuration is set forth in FIG. 14. As shown there, one may use a magnet 1402, which need not be a rod, but may be extended in width transverse to the polar direction. It may be swept through the pool laterally. The magnet 1402 comprises at one pole a tapered region 1404 which may be hemispheric, or, alternatively, as shown, comprise a compound linear narrowing, having region of first narrowing 1406 and a distal region of increased narrowing 1408, ending in a sharp tip or a tip having a small radius of curvature at a pole, e.g., the South pole. The magnetic field, as illustrated by magnetic lines of force at 1410, is close to the non-magnetic floor of the container 1416. The illustrated configuration improves the magnetic gradient over a simple blunt end or hemispherical end of a magnet. This configuration can be applied to the tips of rods, to multiple magnets, and magnets with opposing poles can be arrayed so that the gradients are steeper.

Culture of an Isolated Cell

In addition to conducting genetic analyses on isolated individual cells, the present device and methods may be used to capture viable cells that can be grown in culture. Models for testing viability of captured cells were developed by generating tumor xenografts from both human breast cancer cell lines (MDA-MB-231) and primary tumors excised from breast cancer patients and orthotopically implanted into the mammary fat pads of immunocompromised female mice (NOD-SCID). MDA-MB-231 cancer cells formed mammary fat pad tumors and macroscopic lung metastases in forty mice. Mouse blood was taken and hundreds of CTCs were captured using human-specific EpCAM-labeled magnetic beads. These CTCs were placed into culture media and incubated. The CTCs attached to the culture dishes and rapidly proliferated. Control mice injected with saline did not develop primary tumors or metastases, and their blood contained no CTCs. Also, three tumor xenografts were generated from primary human breast cancers. Tumor tissue was excised from female patients and implanted into mouse mammary fat pads. Human CTCs were isolated from mouse blood of all three xenograft models and CTCs from one of the models was maintained in culture. To our knowledge, this is the first demonstration of isolation of viable human CTCs from primary human tumor xenografts. These methods pave the way for culturing patient-specific CTCs that may be used for drug testing, drug discovery, or other studies.

The foregoing shows that the present device is able to isolate viable and pure circulating tumor cells from whole blood for genetic analysis. The device and present methods may also be applied to capture of fetal cells from maternal blood. Capture of spiked cells and tumor cells show no contaminating blood cells, and we are working on methods to improve capture rates, which currently average 25%. Here, we compare multiplex qRT-PCR data of single CTCs isolated from two patients with metastatic breast cancer with the phenotype of primary tumors and metastases. In-patient SM014, although her primary tumor was ER−/PR−/HER2+, the CTC was ER−/PR−/HER2−, which matched the phenotype of her bone metastatic disease that progressed on trastuzumab. In-patient SUBL017, the primary tumor was ER−/PR+/HER2− and an intervening supraclavicular LN metastasis was ER+/PR−/HER−. The CTCs we captured and analyzed from this patient, now with progressing bone metastases of unknown receptor status, display an ER−/PR−/HER2− phenotype. We have also found that gene expression of CTCs from the same patient vary. Our data indicate that single CTC gene expression may be highly variable and may reflect the heterogeneity of cells from single or multiple metastatic lesions.

The use of a robot allows the device to be programmed to utilize multiple samples, such as in a 6 well plate. The robot is programmable to vary capture and release configurations for optimizing capture efficiency and sample purity. Robot works with all commercially available immunomagnetic particles. Modifications can be made to the robot, such as allowing the magnetic rods with plastic sleeve to move to their next station (capture, wash, release station) in a circular (by putting the wells on a conveyor belt-type apparatus), rather than the linear rod-arm advancement as is currently configured. We may also add an orthogonal arm for manual or robotic sliding of an additional magnetic plate under the final release station to facilitate cell release from the plastic sleeve.

The present device may, in certain aspects, be characterized as comprising, firstly, magnetic rods that sweep through blood or other solution. These rods are actual magnets (axial or diametric) rather than metals magnetized by an external magnet. Secondly, it comprises removable plastic sleeves over magnets to facilitate multiple release cycles to assure high capture efficiency and high purity (no contaminating cells—other devices have a 100-1000:1 ratio of contaminating cells to captured cells). Thirdly, it comprises an actuator for sweeping the magnets and for carrying out a sweeping or shaking step at the end of release cycle to assure release of captured cells into appropriate solution. Fourthly, it uses plastic (for a sleeve over the magnet) that has lowest non-specific binding of contaminating cells. Fifthly, it has the ability to capture rare cells at very low input numbers. For example, cancer blood samples may have 0-10 cells per 7.5 cc tube.

In the present method, one may obtain a composition having cells covered with numerous beads, and which contain a significant number (at least 25%) of target cells. Target cells may be picked by hand through a microscope and a micropipette, and the DNA, RNA or other material extracted, or the cell may be cultured.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Each and every patent or publication which is cited for further information is intended to be and hereby is incorporated by reference to the same extent as if each was specifically and individually incorporated by reference, to the fullest extent permitted by law.

REFERENCES

1. B. Naume, E. Borgen, K. Beiske, T. K. Herstad, G. Ravnas, A. Renolen, S. Trachsel, K. Thrane-Steen, S. Funderud, and G. Kvalheim. "Immunomagnetic techniques for the enrichment and detection of isolated breast carcinoma cells in bone marrow and peripheral blood," *Journal of Hematotherapy*, 1997, Vol. 6(2), pp. 103-14.
2. E. Racila, D. Euhus, A. J. Weiss, C. Rao, J. McConnell, L. W. Terstappen, and J. W. Uhr, "Detection and characterization of carcinoma cells in the blood," *Proceedings in the National Academy of Sciences USA*, 1998, Vol. 95(8), pp. 4589-94.
3. E. H. Romond, et al., "Trastuzumab plus Adjuvant Chemotherapy for Operable HER2-Positive Breast Cancer", *New England Journal of Medicine*. Vol. 353, pp. 1673-84, 2005
4. M. J. Piccart-Gebhart, et al. "Trastuzumab after Adjuvant Chemotherapy in HER2-Positive Breast Cancer," *New England Journal of Medicine*, 2005, Vol. 353, pp. 1659-72.
5. Y. Tamaki, Y. Miyoshi, and S. Noguchi, "Adjuvant hormonal therapy," *Breast Cancer*, 2002, Vol. 9(3), pp. 185-9.
6. E. Dikicioglu, S. Barutca, N. Meydan, I. Meteoglu, "Biological characteristics of breast cancer at the primary tumour and the involved lymph nodes," *International Journal of Clinical Practice*, 2005, Vol. 59(9), pp. 1039-44.
7. Y. Gong, D. J. Booser, N. Sneige, "Comparison of HER-2 status determined by fluorescence in situ hybridization in primary and metastatic breast carcinoma," *Cancer*, 2005, Vol. 103(9), pp. 1763-9.
8. J Zidan, I Dashkovsky, C Stayerman, W Basher, C Cozacov and A Hadary, "Comparison of HER− of 2 overexpression in primary breast cancer and metastatic sites and its effect on biological targeting therapy metastatic disease," *British Journal of Cancer*, 2005, Vol. 93, pp. 552-556.
9. E. F. Solomayer, Sven Becker, G. Pergola-Becker, R. Bachmann, B. Krämer, U. Vogel, H. Neubauer, D. Wallwiener, J. Huober and T. Fehm, "Comparison of HER2 status between primary tumor and disseminated tumor cells in primary breast cancer patients", *Breast Cancer Research and Treatment*, 2006.

What is claimed is:

1. A device for capture and isolation of target cells from a mixed cell population wherein the target cells are labeled with magnetically responsive material to form labeled target cells, comprising:
   (a) a container for holding the labeled target cells;
   (b) a magnetic member having a tip end and another end connected to an actuator;
   (c) a sleeve between the magnetic member and the mixed cell population to prevent direct contact of cells with the magnetic member, said sleeve being nonmagnetic and nonadherent to cells in the mixed cell population;
   (d) said sleeve being separable from the magnetic member by the actuator, which actuator causes movement between the magnetic member and the sleeve, whereby the magnetic member is moved more or less into the sleeve; and
   (e) said actuator being constructed and arranged for causing in the device (i) relative orbital stirring movement between the magnetic member and the mixed cell population to contact the magnetic member with a majority of cells in the mixed cell population, and (ii) movement of the magnetic member into and out of the container to retrieve target cells from the mixed cell population.

2. The device of claim 1 wherein the magnetic member is a rod having a diameter of at least 4 mm to produce a high magnetic field strength and having a tapered tip for producing a high magnetic gradient.

3. The device of claim 1 where the magnetic member has a tapered tip.

4. The device of claim 1 wherein the magnetic member possesses a field strength at the tip of at least 0.5 Tesla.

5. The device of claim 4 where the magnetic member is a rare earth magnet.

6. The device of claim 4 where the magnetic member has a pull strength of at least 70 pounds.

7. The device of claim 4 where the magnetic member has a surface field strength of 0.2 to 1 Tesla.

8. The device of claim 1 where the magnetic member comprises neodymium, iron and boron.

9. The device of claim 1 where the sleeve consists essentially of a material selected from the group consisting of vinyl polymer, paramagnetic metal, ceramic material, and polyHEMA.

10. The device of claim 1 where the magnetic member consists essentially of neodymium, iron and boron alloy.

11. The device of claim 1 further comprising one or more containers for holding the sample, for holding a wash solution and for holding target cells after isolation from the mixed cell population.

12. The device of claim 11 where there are separate containers for holding sample, wash solution and target cells.

13. The device of claim 11 where the containers comprise a material which is non-adherent to target cells.

14. A device for capture and isolation of target cells in a sample having a mixed cell population of target cells and contaminant cells, wherein the target cells are labeled with magnetically responsive material to form labeled target cells, comprising:
   (a) a container for holding the sample;
   (b) a magnetic member having a tip;
   (c) a sleeve between the magnetic member and the mixed cell population to prevent direct contact of cells with the magnetic member, said sleeve being nonmagnetic and nonadherent to cells in the mixed cell population;
   (d) said sleeve being separable from the magnetic member by an actuator that causes movement between the magnetic member and the sleeve whereby the magnetic member is moved more or less into the sleeve; and
   (e) said actuator being constructed and arranged for causing (i) relative stifling movement applied in concentric circles in the container between the magnetic member and the mixed cell population to contact the magnetic member with a majority of cells in the mixed cell population, and (ii) movement of the magnetic member into and out of the container to retrieve target cells from the mixed cell population.

15. The device of claim 14 further comprising a container which comprises a portion having a magnet opposite the magnetic member, for attracting isolated labeled target cells from the magnetic member in forming an isolated population.

16. The device of claim 14 wherein the container defines an open pool for holding the sample.

17. The device of claim 14 comprising only one magnetic member in one container.

18. The device of claim 14 comprising multiple magnetic members controlled by a single actuator.

19. The device of claim 14 further comprising a probe for extracting a single target cell from a collection of target cells isolated after removal of contaminant cells.

20. The device of claim 19 comprising a computer programmed with image recognition software and controlling the probe.

21. The device of claim 14 further comprising a magnet for removing target cells from the sleeve.

* * * * *

UNITED STATES PATENT AND TRADEMARK OFFICE
CERTIFICATE OF CORRECTION

PATENT NO.      : 9,267,943 B2                                  Page 1 of 1
APPLICATION NO. : 13/284482
DATED           : February 23, 2016
INVENTOR(S)     : Davis et al.

It is certified that error appears in the above-identified patent and that said Letters Patent is hereby corrected as shown below:

IN THE CLAIMS:

Column 50, line 23 (Claim 14, line 17) delete "stifling" and add "stirring".

Signed and Sealed this
Nineteenth Day of July, 2016

Michelle K. Lee
*Director of the United States Patent and Trademark Office*